United States Patent
Smith et al.

(10) Patent No.: US 10,329,619 B2
(45) Date of Patent: *Jun. 25, 2019

(54) METHODS AND MATERIALS FOR DETECTING GENETIC OR EPIGENETIC ELEMENTS

(71) Applicant: Cascade Biosystems, Inc., Colfax, WI (US)

(72) Inventors: Kenneth D. Smith, Colfax, WI (US); Nina Yazvenko, Vancouver, WA (US); Mariya Smit, Vancouver, WA (US)

(73) Assignee: Cascade Biosystems, Inc., Colfax, WI (US)

( * ) Notice: Subject to any disclaimer, the term of this patent is extended or adjusted under 35 U.S.C. 154(b) by 55 days.

This patent is subject to a terminal disclaimer.

(21) Appl. No.: 15/604,112

(22) Filed: May 24, 2017

(65) Prior Publication Data

US 2017/0268060 A1 Sep. 21, 2017

Related U.S. Application Data

(63) Continuation of application No. 14/841,282, filed on Aug. 31, 2015, now Pat. No. 9,689,037, which is a continuation of application No. 14/046,389, filed on Oct. 4, 2013, now Pat. No. 9,150,921, which is a continuation of application No. 13/027,887, filed on Feb. 15, 2011, now Pat. No. 8,551,701.

(60) Provisional application No. 61/304,793, filed on Feb. 15, 2010.

(51) Int. Cl.
*C12Q 1/6883* (2018.01)
*C12Q 1/683* (2018.01)
*C12Q 1/6876* (2018.01)

(52) U.S. Cl.
CPC ........... *C12Q 1/6883* (2013.01); *C12Q 1/683* (2013.01); *C12Q 1/6876* (2013.01); *C12Q 2600/154* (2013.01); *C12Q 2600/156* (2013.01)

(58) Field of Classification Search
CPC ............................ C12Q 1/6883; C12Q 1/6876
See application file for complete search history.

(56) References Cited

U.S. PATENT DOCUMENTS

| | | |
|---|---|---|
| 4,699,876 A | 10/1987 | Libeskind |
| 4,775,619 A | 10/1988 | Urdea |
| 5,102,784 A | 4/1992 | George, Jr. |
| 5,403,711 A | 4/1995 | Walder et al. |
| 5,679,510 A | 10/1997 | Ray et al. |
| 5,795,718 A | 8/1998 | Eisenbeis |
| 5,858,665 A | 1/1999 | Hepp et al. |
| 6,110,677 A | 8/2000 | Western et al. |
| 6,114,117 A | 9/2000 | Hepp et al. |
| 6,156,953 A | 12/2000 | Preuss et al. |
| 6,492,120 B1 | 12/2002 | Galvan et al. |
| 6,825,010 B2 | 11/2004 | Spier et al. |
| 7,524,629 B2 | 4/2009 | Olek et al. |
| 8,278,048 B2 | 10/2012 | Smith et al. |
| 8,470,533 B2 | 6/2013 | Smith et al. |
| 8,551,701 B2 | 10/2013 | Smith et al. |
| 8,597,886 B2 | 12/2013 | Smith et al. |
| 8,623,616 B2 | 1/2014 | Smith et al. |
| 8,632,974 B2 | 1/2014 | Smith et al. |
| 8,865,407 B2 | 10/2014 | Smith et al. |
| 9,150,921 B2 | 10/2015 | Smith et al. |
| 9,150,932 B2 | 10/2015 | Smith et al. |
| 9,150,935 B2 | 10/2015 | Smith et al. |
| 9,399,802 B2 | 7/2016 | Smith et al. |
| 9,428,814 B2 | 8/2016 | Smith et al. |
| 9,677,120 B2 | 6/2017 | Smith et al. |
| 9,689,037 B2 | 6/2017 | Smith et al. |
| 2002/0015951 A1 | 2/2002 | Bader et al. |
| 2002/0123620 A1 | 9/2002 | Danenberg |
| 2003/0124594 A1 | 7/2003 | Church et al. |
| 2003/0235837 A1 | 12/2003 | Keim et al. |
| 2004/0023207 A1 | 2/2004 | Polansky |
| 2005/0003390 A1 | 1/2005 | Axenovich et al. |
| 2006/0172325 A1 | 8/2006 | Brownstein et al. |
| 2006/0240431 A1 | 10/2006 | Fu |
| 2007/0231800 A1 | 10/2007 | Roberts et al. |

(Continued)

FOREIGN PATENT DOCUMENTS

| CN | 1236395 | 11/1999 |
|---|---|---|
| WO | WO 1998/004738 | 2/1998 |

(Continued)

OTHER PUBLICATIONS

Albretsen et al., "Applications of magnetic beads with covalently attached oligonucleotides in hybridization: isolation and detection of specific measles virus mRNA from a crude cell lysate," Anal. Biochem., 1990, 189(1):40-50.

Beaucage et al., "Deoxynucleoside phosphoramidites—a new class of key intermediates for deoxypolynucleotide synthesis," Tet. Let., 1981, 22(20):1859-1862.

Bekkaoui et al., "Cycling probe technology with RNase H attached to an oligonucleotide," BioTechniques, Feb. 1996, 20:240-248.

Black, Microbiology. Principles and Applications, Third Edition, 1996, pp. 144-148.

Chan et al., "Quantitative Analysis of Circulating Methylated DNA as a Biomarker for Hepatocellular Carcinoma," Clin. Chem., Jul. 24, 2008, 54:1664-1672.

(Continued)

*Primary Examiner* — Narayan K Bhat
(74) *Attorney, Agent, or Firm* — Fish & Richardson P.C.

(57) ABSTRACT

This document provides methods and materials for detecting genetic and/or epigenetic elements. For example, methods and materials for detecting the presence or absence of target nucleic acid containing a genetic or epigenetic element, methods and materials for detecting the amount of target nucleic acid containing a genetic or epigenetic element within a sample, kits for detecting the presence or absence of target nucleic acid containing a genetic or epigenetic element, kits for detecting the amount of target nucleic acid containing a genetic or epigenetic element present within a sample, and methods for making such kits are provided.

20 Claims, 17 Drawing Sheets

Specification includes a Sequence Listing.

(56) References Cited

U.S. PATENT DOCUMENTS

2008/0021205 A1 1/2008 Blau et al.
2009/0263809 A1 10/2009 Roberton et al.

FOREIGN PATENT DOCUMENTS

| WO | WO 1998/004739 | 2/1998 |
|---|---|---|
| WO | WO 1998/019168 | 5/1998 |
| WO | WO 2002/059359 | 8/2002 |
| WO | WO 2004/101788 | 11/2004 |
| WO | WO 2004/108897 | 12/2004 |
| WO | WO 2010/019414 | 2/2010 |

OTHER PUBLICATIONS

Di Gioia et al., "Quantitative evaluation of RASSF1A methylation in the non-lesional, regenerative and neoplastic liver," BMC Cancer, 2006, 6:89, 12 pages.
Dill et al., "Immunoassays based on electrochemical detection using microelectrode arrays," Biosensors and Bioelectronics, 2004, 20:736-742.
Fischer et al., "Prognostic significance of RASSF1A promoter methylation on survival of non-small cell lung cancer patients treated with gemcitabine," Lung Cancer, 2007, 56:115-123.
Froehler et al., "Synthesis of DNA via deoxynucleoside H-phosphonate intermediates," Nucl. Acid Res., 1986, 14:5399-5407.
Gaffney et al., "Large-scale oligonucleotides synthesis by the H-Phosphonate method," Tet. Let., 1988, 29:2619-2622.
Garegg et al., "Nucleoside H-phosphonates III. Chemical synthesis of oligodeoxyribonucleotides by the hydrogenphosphonate approach," Tet. Let., 1986, 27:4051-4054.
Garegg et al., "Nucleoside H-phosphonates IV. Automated solid phase synthesis of oligoribonucleotides by the hydrogenphosphonate approach," Tet. Let., 27:4055-4058 (1986).
GenBank® Accession No. AJ536123; GenBank® GI No. 40643613, Nov. 14, 2006, 3 pages.
GenBank® Accession No. AJ536131; GenBank® GI No. 40643629, Nov. 14, 2006, 3 pages.
GenBank® Accession No. AJ536135; GenBank® GI No. 40643637, Nov. 14, 2006, 4 pages.
GenBank® Accession No. BA000007 GenBank® GI No. 47118301, Jan. 18, 2008, p. 1 of 157.
GenBank® Accession No. CP000052; GenBank® GI No. 761681535 Mar. 2010, 4 pages.
GenBank® Accession No. NC_002952 GenBank® GI No. 49482253, Jan. 22, 2012, p. 1 of 109.
GenBank® Accession No. NC_000962; GenBank® GI No. 5711668119 Jan. 2012, 2 pages.
GenBank® Accession No. NC_001803; GenBank® GI No. 9629367, Nov. 22, 2009, 8 pages.
GenBank® Accession No. NC_002016; GenBank® GI No. 8486122, Jul. 16, 2008, 2 pages.
GenBank® Accession No. NC_002695; GenBank® GI No. 15829254 at 1267936-1268205, Jan. 25, 2012, p. 1 of 178.
GenBank® Accession No. NC_002946; GenBank® GI No. 59800473, Jan. 20, 2012, p. 1 of 285 pages.
GenBank® Accession No. NC_003198; GenBank® GI No. 16758993, Jan. 20, 2012, 1 page.
GenBank® Accession No. NC_003210; GenBank® GI No. 16802048, Jan. 20, 2012, 1 page.
GenBank® Accession No. NC_003266; GenBank® GI No. 51527264, May 6, 2009, p. 1 of 21 pages.
GenBank® Accession No. NC_003485; GenBank® GI No. 19745201, Jan. 20, 2012, p. 1 of 350.
GenBank® Accession No. NC_003912; GenBank® GI No. 57236892, Aug. 1, 2011, p. 1 of 337.
GenBank® Accession No. NC_004603; GenBank® GI No. 28896774, Jan. 20, 2012, p. 1 of 441.
GenBank® Accession No. NC_007607; GenBank® GI No. 82524407, Apr. 1, 2010, p. 1 of 92.
GenBank® Accession No. NC_008533; GenBank® GI No. 116515308, Jan. 26, 2012, p. 1 of 383.
GenBank® Accession No. NC_010741; GenBank® GI No. 189025236, May 2, 2011, p. 1 of 174.
GenBank® Accession No. NC_013450; GenBank® GI No. 269201690, Feb. 14, 2012, p. 1 of 404.
GenBank® Accession No. NM_020469; GenBank® GI No. 58331215, Apr. 12, 2012, 4 pages.
GenBank® Accession No. X01712.1; GenBank® GI No. 59898, Apr. 18, 2005, 2 pages.
Guerini et al., "Rapid enrichment strategy for isolation of Listeria from bovine hide, carcass, and meat samples," J. Food Prot., 2007, 70(1):53-57.
He et al., "Selective and homogeneous fluorescent Dna detection by target-induced strand displacement using cationic conjugated polyelectrolytes," Anal. Chem., 2008, 80(6):2239-2243.
Jin et al., "Multiplexed bead-based mesofluidic system for detection of food-borne pathogenic bacteria," Appl. Environ. Microbiol., 2009, 75:6647-6654.
Kanagawa, "Bias and artifacts in multitemplate polymerase chain reactions (PCR)," J Biosci Bioeng., 2003, 96(4):317-323.
Kiesling et al., "Sequence specific detection of DNA using nicking endonuclease signal amplification (NESA)," Nucl Acid Res, 2007 35(18):e117.
Liu et al., "Electrochemical detection of hepatitis C virus based on site-specific DNA cleavage of BamHI endonuclease," Chem Commun (Camb), Apr. 7, 2009, (13):1635-1637.
Maruya et al., "Differential methylation status of tumor-associated genes in head and neck squamous carcinoma: incidence and potential implications," Clin. Cancer Res., 2004, 10:3825-3830.
McClelland et al., Effect of site-specific modification on restriction endonucleases and DNA modification methyltransferases, Nucleic Acids Res., 1994, 22:3640-3659.
Nam et al., "Evaluation of universal pre-enrichment broth for isolation of *Salmonella spp., Escherichia coli* O157:H7, and Listeria monocytogenes from daily farm environmental samples," Foodborne Pathog. Dis., 2004, 1(1):37-44.
O'Mahony and Papkovsky, "Rapid high throughput assessment of aerobic bacteria in complex samples by fluorescence-based oxygen respirometry," Applied and Environmental Microbiology, 2006, 72:1279-1287.
O'Mahony et al., "Analysis of total aerobic viable counts in samples of raw meat using fluorescence-based probe and oxygen consumption assay," Food Control, 2009, 20:129-135.
Pei, D. et. al., "Site-specific cleavage of duplex DNA by a semisynthetic nuclease via triple-helix formation," Proceedings of the National Academy of Sciences of the United States of America, vol. 87, No. 24, (1990), pp. 9858-9862.
Perelle et al., "A LightCycler real-time PCR hybridization probe assay for detecting food-borne thermophilic Campylobacter," Mol. Cell. Probes, 2004, 18:321-327.
Polz and Cavanaugh, "Bias in Template-to-Product Ratios in Multitemplate PCR," Applied and Environmental Microbiology, 1998, 64(10):3724-3730.
Rykova et al., "Methylation-Based Analysis of Circulating DNA for Breast Tumor Screening," Ann. N.Y. Acad. Sci., 2008, 1137:232-235.
Schrank et al., "Influence of enrichment media and application of a PCR based method to detect *Salmonella* in poultry industry products and clinical samples," Vet. Micro., 2001, 82:45-53.
Sipos et al., "Effect of primer mismatch, annealing temperature and PCR cycle number on 16S rRNA gene-targeting bacterial community analysis," FEMS Microbiol Ecol., 2007, 60(2):341-350.
Sud'ina et al., "Affinity Modification of the Restriction Endonuclease SsoII by 2'—Aldehyde-Containing Double Stranded DNAs," Biochemistry (Moscow), vol. 70, No. 8, 2005, pp. 941-947.
Sunami et al., "Analysis of methylated circulating DNA in cancer patients' blood," Methods Mol. Biol., 2009, 507:349-356.
Szyf, "Targeting DNA methylation in cancer," Ageing Res. Rev., 2003, 2(3):299-328.
Urdea, "Synthesis and characterization of branched DNA (BDNA) for the direct and quantitative detection of CMV, HBV, HCV, and HIV," Clinical Chemistry, 1993, 39(4):725-726.

(56) References Cited

OTHER PUBLICATIONS

Wang et al., "Human thiopurine S-methyltransferase pharmacogenetics: Variant allozyme misfolding and aggresome formation," Proc. Natl. Acad. Sci. USA, 2005, 102(26):9394-9399, Published online before print Jun. 20, 2005.
Wang et al., "Identification of epigenetic aberrant promoter methylation of RASSF1A in serum DNA and its clinicopathological significance in lung cancer," Lung Cancer, 2007, 56:289-294.
Weisenberger et al., "DNA methylation analysis by digital bisulfate genomic sequencing and digital MethyLight," Nucl Acid Res., 2008, 36(14):4689-4698.
Widschwendter et al., "Epigenotyping in peripheral blood cell DNA and breast cancer risk: a proof of principle study," PLoS ONE, 2008, 3(7):e2656.
Yeo et al., "High frequency of promoter hypermethylation of RASSF1A in tumorous and nontumorous tissue of breast cancer," Pathology, 2005, 37:125-130.
Zhang et al., "Genetic diversity of intimin genes of attaching and effacing *Escherichia coli* strains," J. Clin. Microbiol., 2002, 40:4486-4492.
International Preliminary Report on Patentability for PCT/US2011/024908, dated Aug. 30, 2012, 11 pages.
International Preliminary Report on Patentability for PCT/US2011/024912, dated Aug. 30, 2012, 11 pages.
International Preliminary Report on Patentability for PCT/US2011/024913, dated Aug. 30, 2012, 11 pages.
International Preliminary Report on Patentability for PCT/US2011/024916, dated Aug. 30, 2012, 11 pages.
European Search Report for App. No. 09807076.6, dated Sep. 7, 2011, 5 pages.
International Preliminary Report on Patentability PCT/US2009/052716, dated Feb. 15, 2011, 5 pages.
International Search Report and Written Opinion of the International Searching Authority in PCT/US2009/052716, dated May 3, 2010, 7 pages.
International Search Report and Written Opinion of the International Searching Authority, PCT/US2011/024908, dated Apr. 15, 2011, 13 pages.
International Search Report and Written Opinion of the International Searching Authority, PCT/US2011/024912, dated Sep. 29, 2011, 18 pages.
International Search Report and Written Opinion of the International Searching Authority, PCT/US2011/024913, dated Apr. 15, 2011, 14 pages.
International Search Report and Written Opinion of the International Searching Authority, PCT/US2011/024916, dated Oct. 4, 2011, 15 pages.
Invitation to Pay Additional Fees and, Where Applicable, Protest Fee, PCT/US2009/052716, dated Mar. 8, 2010, 7 pages.
U.S. Appl. No. 12/535,017, Office Action, dated Feb. 24, 2012, 14 pages.
European Patent Application No. 09807076.6, Communication pursuant to Article 94(3) EPC, dated Mar. 21, 2012, 3 pages.
U.S. Appl. No. 13/027,887, Office Action, dated Apr. 24, 2012, 28 pages.
Examination Report in International Application No. 1666/CHENP/2011, dated Mar. 26, 2018, 6 pages (with English Translation).
U.S. Appl. No. 14/627,742, filed Feb. 20, 2015, U.S. Pat. No. 2015/0225769, dated Aug. 13, 2015, Smith et al.
U.S. Appl. No. 15/218,415, filed Jul. 25, 2016, U.S. Pat. No. 2016/0362727, dated Dec. 15, 2016, Smith et al.
U.S. Appl. No. 15/225,365, filed Aug. 1, 2016, U.S. Pat. No. 2016/0333395, dated Nov. 17, 2016, Smith et al.
U.S. Appl. No. 15/587,944, filed May 5, 2017, U.S. Pat. No. 2017/0240953, dated Aug. 24, 2017, Smith et al.

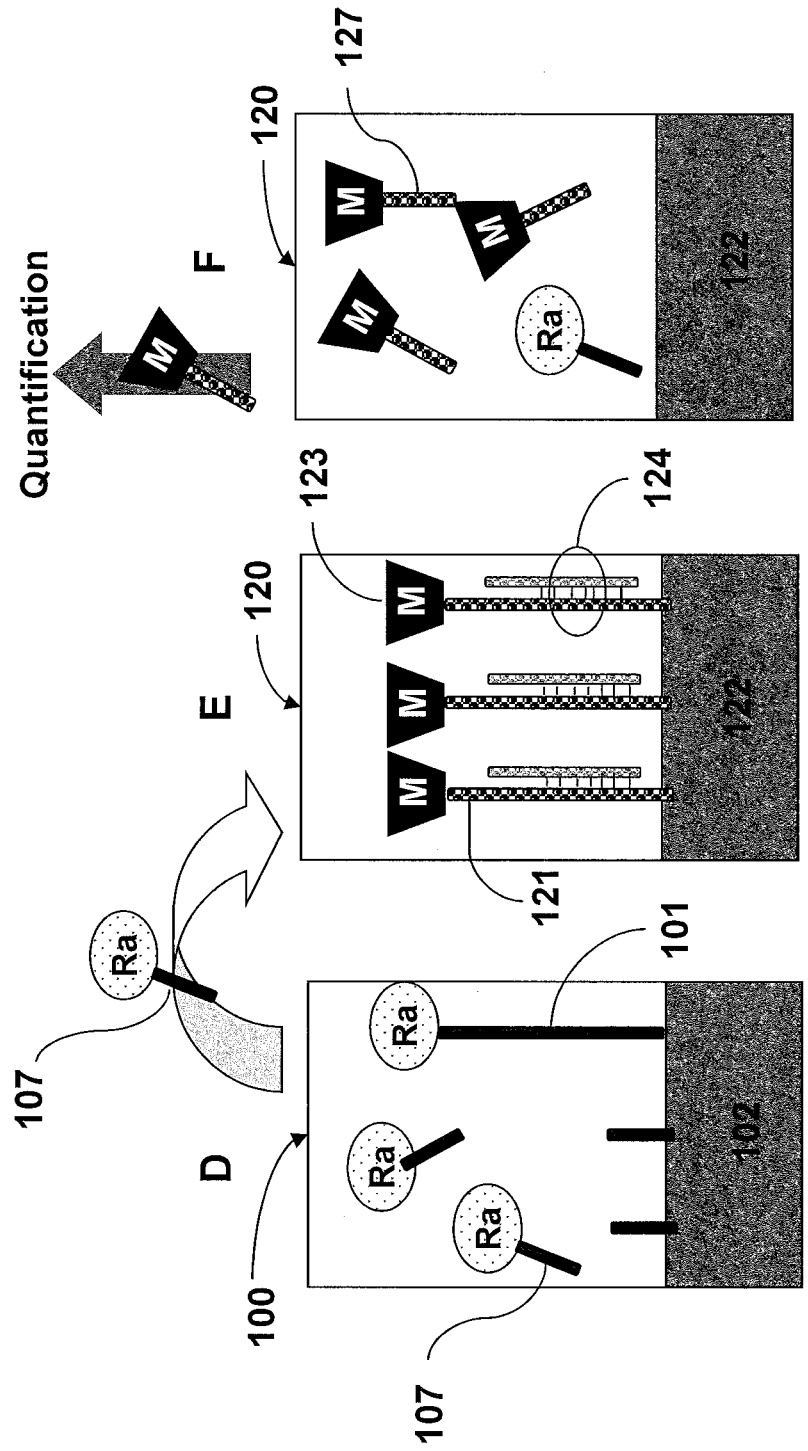
Figure 1 con't

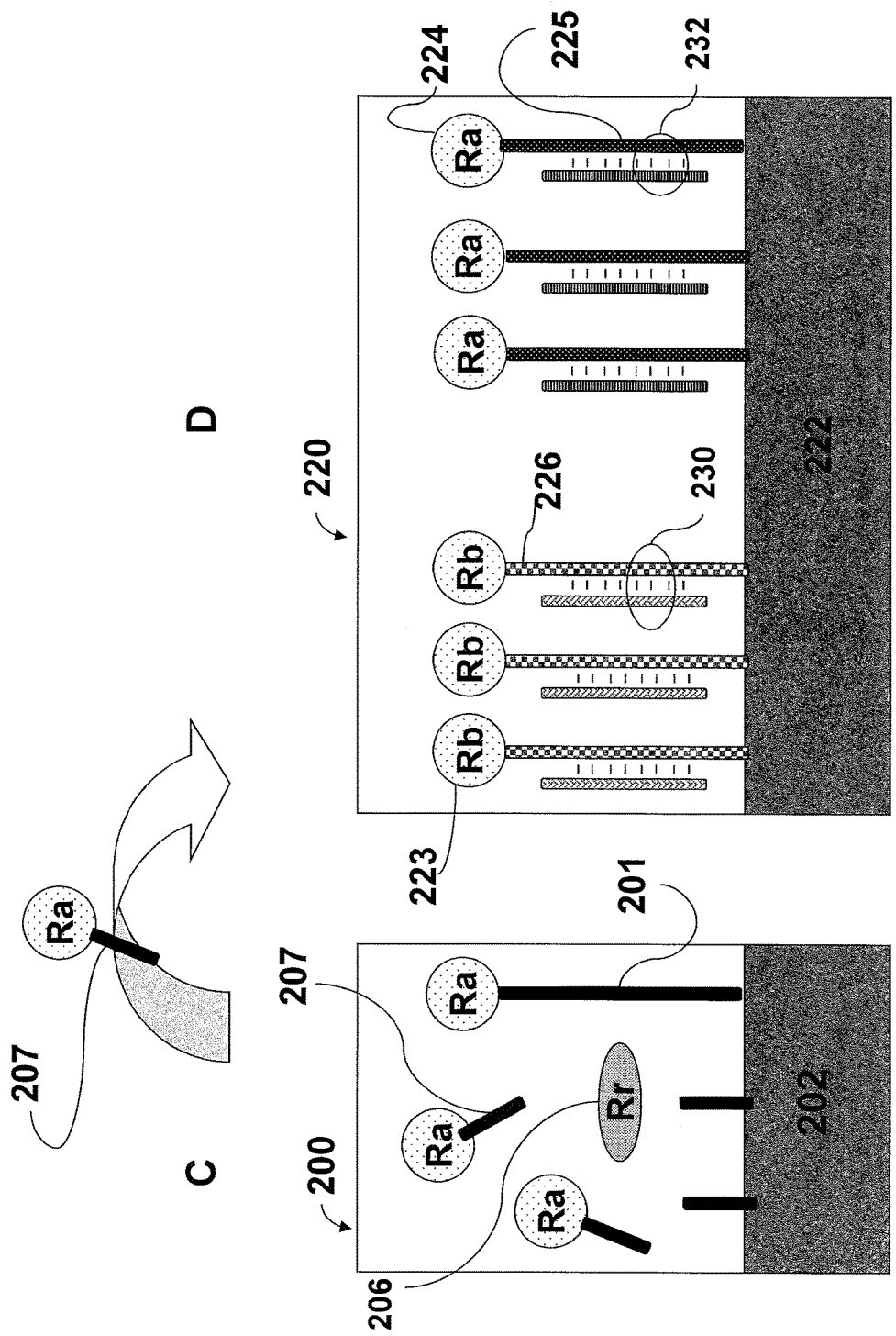
Figure 3 con't

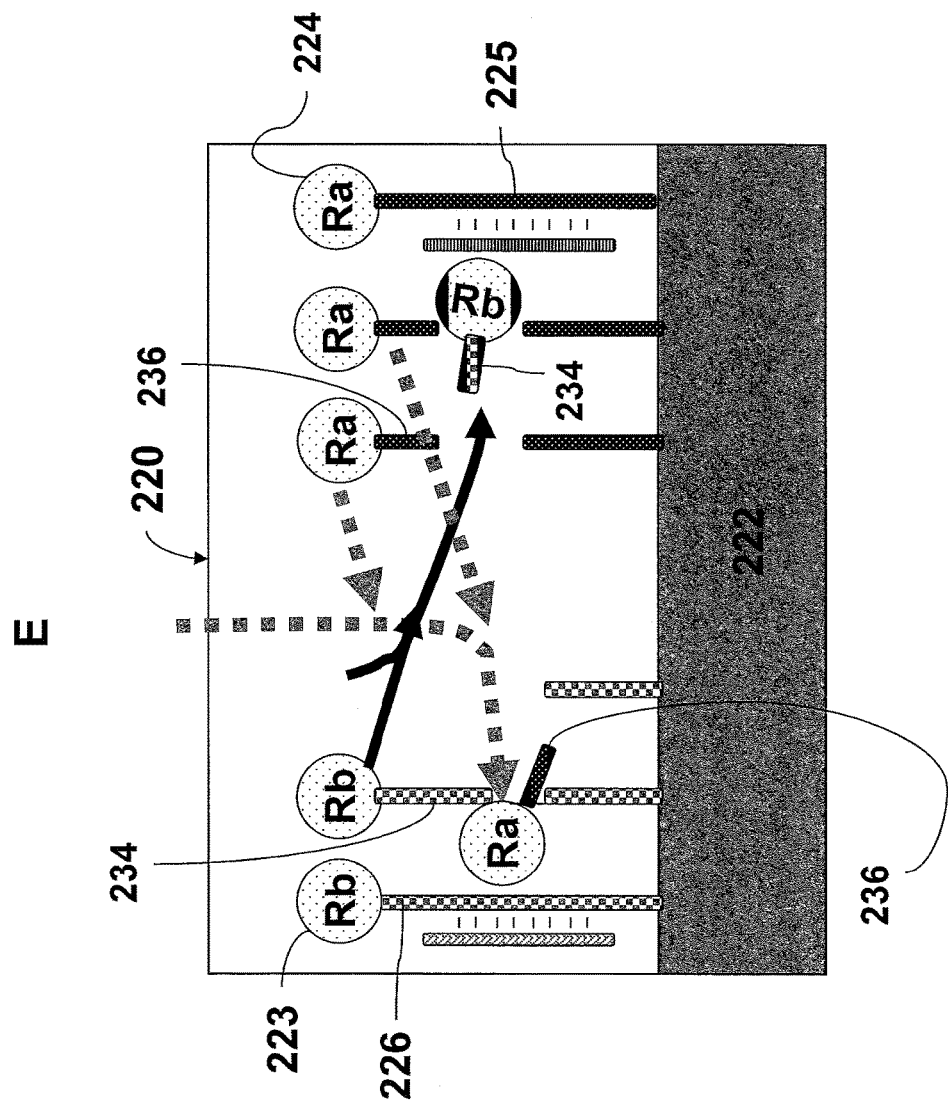
Figure 3 con't

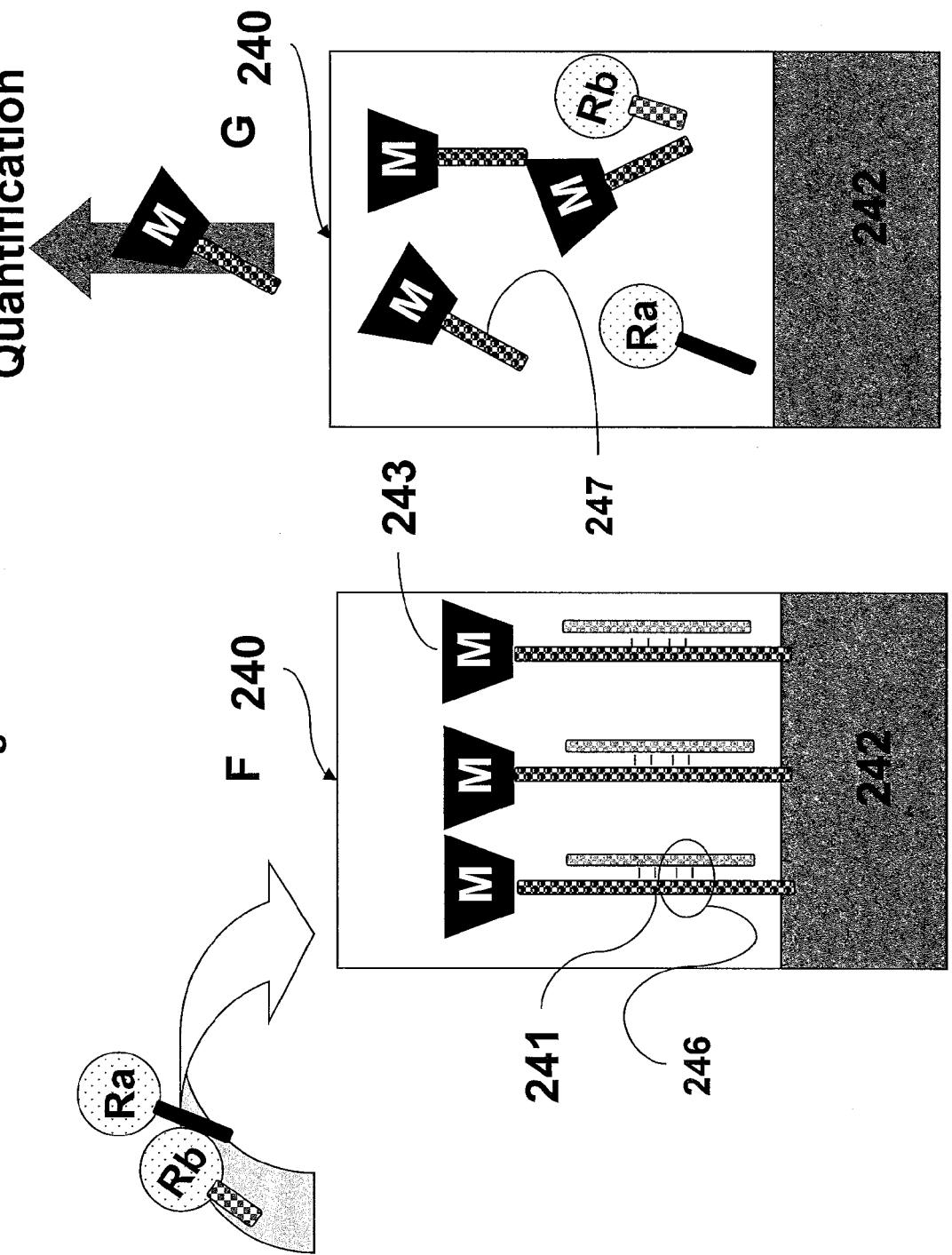
Figure 3 con't

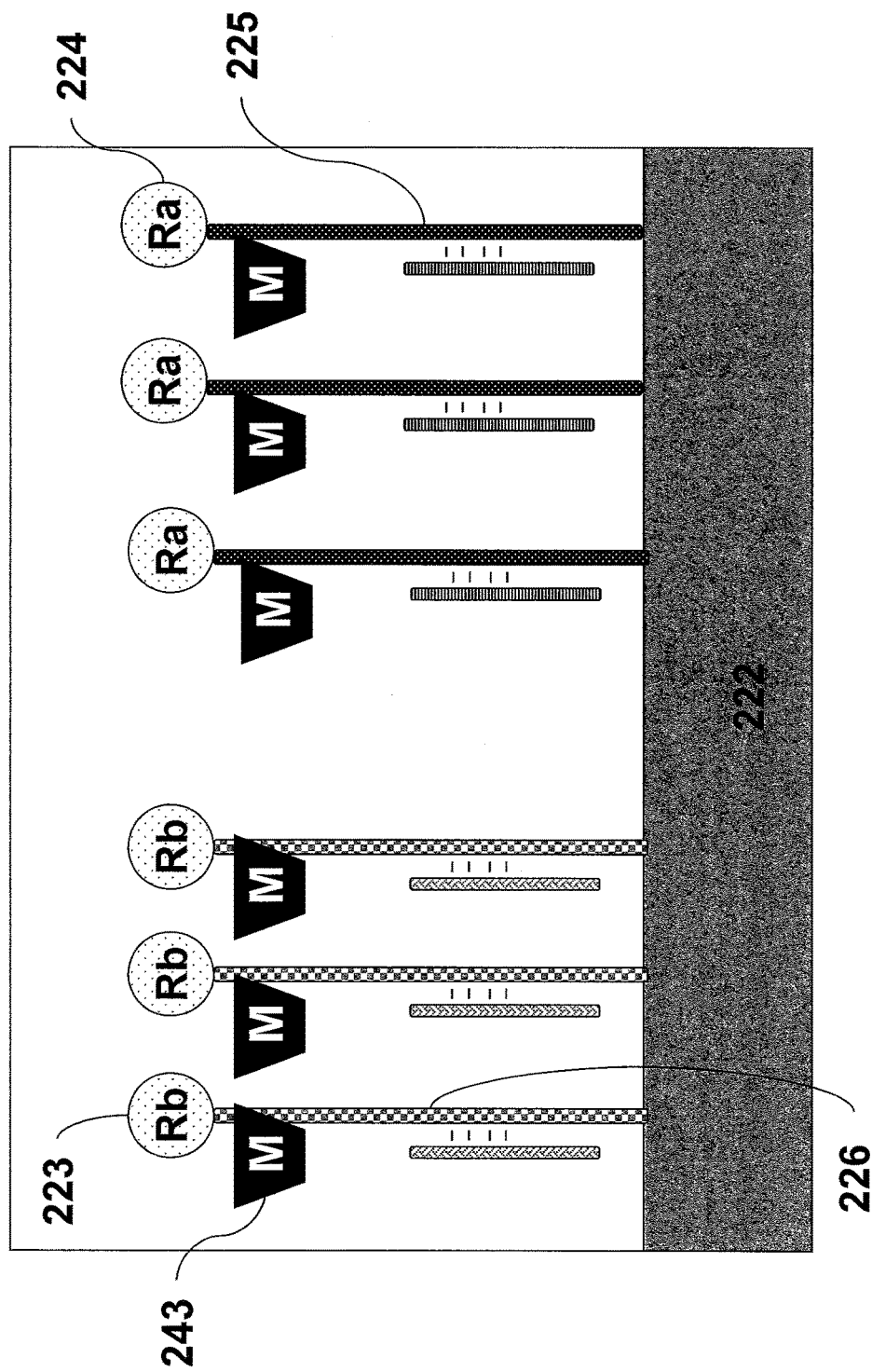

Figure 11

Recognition site | | | | | | | | | | | Cleavage site
G G A T G N N N N N N N N N/N N N
C C T A C N N N N N N N N N N/N N

METHODS AND MATERIALS FOR DETECTING GENETIC OR EPIGENETIC ELEMENTS

CROSS-REFERENCE TO RELATED APPLICATION

This application is a continuation of U.S. application Ser. No. 14/841,282, filed Aug. 31, 2015 (now U.S. Pat. No. 9,689,037), which is a continuation of U.S. application Ser. No. 14/046,389, filed Oct. 4, 2013 (now U.S. Pat. No. 9,150,921), which is a continuation of U.S. application Ser. No. 13/027,887, filed Feb. 15, 2011 (now U.S. Pat. No. 8,551,701), which claims the benefit of priority of U.S. Provisional Application Ser. No. 61/304,793, filed Feb. 15, 2010. The disclosure of the prior application is considered part of (and is incorporated by reference in) the disclosure of this application.

BACKGROUND

1. Technical Field

This document relates to methods and materials involved in detecting genetic and/or epigenetic elements. For example, this document relates to methods and materials involved in using an enzymatic amplification cascade of restriction endonucleases to detect genetic and/or epigenetic elements present within an organism (e.g., a human).

2. Background

Many aspects of an organism's phenotype are controlled by the genotype of that organism. In other words, the genetic makeup of an organism can control the traits of that organism. Thus, the presence or absence of certain genetic elements such as single nucleotide polymorphisms (SNPs), sequence deletions, or sequence additions present within an organism's genome can provide important information about the organism's health and/or susceptibilities to certain diseases or disorders. Likewise, epigenetic elements such as methylated DNA can control or influence an organism's phenotype. Thus, the presence or absence of certain epigenetic elements such as methylated DNA present within an organism can provide important information about the organism's health and/or susceptibilities to certain diseases or disorders.

SUMMARY

This document provides methods and materials for detecting genetic and/or epigenetic elements. For example, this document relates to methods and materials involved in using an enzymatic amplification cascade of restriction endonucleases to detect genetic and/or epigenetic elements present within an organism (e.g., a human). Information about an organism's genotype can be important for understanding that organism's health and/or susceptibilities to certain diseases or disorders. For example, the presence of certain genetic elements in a human's genome (e.g., genetic markers such as single nucleotide polymorphisms (SNPs), sequence deletions, or sequence additions) can indicate that that particular human has an enzyme deficiency or is susceptible to developing a certain disease. Likewise, information about epigenetic elements that may influence the phenotype of an organism can be important for understanding that organism's health and/or susceptibilities to certain diseases or disorders. For example, the presence of certain epigenetic elements such as methylated DNA can indicate that a human has a particular type of cancer.

In some cases, this document provides methods and materials for detecting target nucleic acid that contains a genetic element or epigenetic element. For example, this document provides methods and materials for detecting the presence or absence of target nucleic acid (e.g., target nucleic acid containing a particular genetic element) in an organism's genome, methods and materials for detecting the presence or absence of target nucleic acid that contains an epigenetic element (e.g., methylated DNA) in a cell of an organism, kits for detecting the presence or absence of target nucleic acid (e.g., target nucleic acid containing a particular genetic element) in an organism's genome, kits for detecting the presence or absence of target nucleic acid that contains an epigenetic element (e.g., methylated DNA) in a cell of an organism, and methods for making such kits.

In general, the methods and materials provided herein can include performing an enzymatic amplification cascade of restriction endonucleases as described herein to detect target nucleic acid indicative of a genetic and/or epigenetic element in a manner that is rapid, inexpensive, sensitive, and specific. For example, a sample (e.g., a sample of genomic nucleic acid or a sample of nucleic acid from a cell or tissue) can be obtained from an organism (e.g., a human) and/or processed such that target nucleic acid, if present within the sample, is capable of hybridizing to probe nucleic acid of an enzymatic amplification cascade of restriction endonucleases described herein. In some cases, such an obtained and/or processed sample can be assessed for the presence, absence, or amount of target nucleic acid using an enzymatic amplification cascade of restriction endonucleases described herein without using a nucleic acid amplification technique (e.g., a PCR-based nucleic acid technique). Assessing samples (e.g., biological samples) for the presence, absence, or amount of target nucleic acid using an enzymatic amplification cascade of restriction endonucleases described herein without using a nucleic acid amplification technique can allow patients as well as medical, laboratory, or veterinarian personnel (e.g., clinicians, physicians, physician's assistants, laboratory technicians, research scientists, and veterinarians) to test organisms for possible genetic and/or epigenetic elements using a nucleic acid-based assay without the need for potentially expensive thermal cycling devices and potentially time consuming thermal cycling techniques. In addition, the methods and materials provided herein can allow patients as well as medical, laboratory, or veterinarian personnel to detect any type of genetic and/or epigenetic element suspected of being present within an organism (e.g., a mammal such as a human). For example, the methods and materials provided herein can be used to detect the presence or absence of a single nucleotide polymorphism within the genome of a human.

In general, one aspect of this document features a method for assessing an organism for a genetic or epigenetic element. The method comprises, or consists essentially of, (a) contacting a sample from the organism with a probe nucleic acid comprising an amplifying restriction endonuclease and a nucleotide sequence complementary to a sequence of a target nucleic acid containing the genetic or epigenetic element under conditions wherein, if the target nucleic acid is present in the sample, at least a portion of the target nucleic acid hybridizes to at least a portion of the probe nucleic acid to form a double-stranded portion of nucleic acid comprising a restriction endonuclease cut site, (b) contacting the double-stranded portion of nucleic acid with a recognition restriction endonuclease having the ability to cut the double-stranded portion of nucleic acid at the restriction endonuclease cut site under conditions wherein the recognition restriction endonuclease cleaves the double-stranded portion of nucleic acid at the restriction endonuclease cut site, thereby separating a portion of the probe nucleic acid comprising the amplifying restriction endonuclease from at least another portion of the probe nucleic acid, (c) contacting the portion of the probe nucleic acid comprising the amplifying restriction endonuclease with a reporter nucleic acid comprising a double-stranded portion of nucleic acid comprising a restriction endonuclease cut site of the amplifying restriction endonuclease under conditions wherein the amplifying restriction endonuclease cleaves the reporter nucleic acid at the restriction endonuclease cut site of the amplifying restriction endonuclease, thereby separating a portion of the reporter nucleic acid from at least another portion of the reporter nucleic acid, and (d) determining the presence or absence of the portion of the reporter nucleic acid, wherein the presence of the portion of the reporter nucleic acid indicates that the sample contains the target nucleic acid, thereby indicating that the organism contains the genetic or epigenetic element, and wherein the absence of the portion of the reporter nucleic acid indicates that the sample does not contain the target nucleic acid, thereby indicating that the organism does not contain the genetic or epigenetic element. The organism can be a human. The organism can be a mammal. The mammal can be selected from the group consisting of bovine, porcine, and equine species. The organism can be a plant. The plant can be selected from the group consisting of trees, flowers, shrubs, grains, grasses, and legumes. The method comprises assessing the organism for the genetic element. The genetic element can be an allelic variant known to exist in the species of the organism. The genetic element can be a single nucleotide polymorphism. The method can comprise assessing the organism for the epigenetic element. The epigenetic element can be a methylated DNA sequence. The sample can be selected from the group consisting of blood samples, hair samples, skin samples, throat swab samples, cheek swab samples, tissue samples, cellular samples, and tumor samples. Prior to step (a), the sample can be a sample that was processed to remove non-nucleic acid material from the sample, thereby increasing the concentration of nucleic acid, if present, within the sample. The sample can be a sample that was subjected to a nucleic acid extraction technique. Prior to step (a), the sample can be a sample that was subjected to a nucleic acid amplification technique to increase the concentration of one or more nucleic acids, if present, within the sample. The sample can be a sample that was subjected to a PCR-based technique designed to amplify the target nucleic acid. Prior to step (a), the method can comprise removing non-nucleic acid material from the sample, thereby increasing the concentration of nucleic acid, if present, within the sample. The removing can comprise performing a nucleic acid extraction technique. Prior to step (a), the method can comprise performing a nucleic acid amplification technique to increase the concentration of one or more nucleic acids, if present, within the sample. The nucleic acid amplification technique can comprise a PCR-based technique designed to amplify the target nucleic acid. Prior to step (a), the method can comprise removing non-nucleic acid material from the sample, thereby increasing the concentration of nucleic acid, if present, within the sample, and performing a nucleic acid amplification technique to increase the concentration of one or more nucleic acids, if present, within the sample. The probe nucleic acid can be single-stranded probe nucleic acid. The probe nucleic acid can be attached to a solid support. The probe nucleic acid can be directly attached to a solid support. The portion of the probe nucleic acid comprising the amplifying restriction endonuclease can be released from the solid support via the step (b). Step (a) and step (b) can be performed in the same compartment, or step (a), step (b), and step (c) can be performed in the same compartment, or step (a), step (b), step (c), and step (d) can be performed in the same compartment. Step (a) and step (b) can be performed in a first compartment, and step (c) can be performed in a second compartment. Step (a) and step (b) can be performed by adding the sample to a compartment comprising the probe nucleic acid and the recognition restriction endonuclease. The probe nucleic acid can comprise (i) a single-stranded portion comprising the nucleotide sequence complementary to the sequence of the target nucleic acid and (ii) a double-stranded portion. The probe nucleic acid can comprise a first nucleic acid strand comprising the nucleotide sequence complementary to the sequence of the target nucleic acid hybridized to a second nucleic acid strand comprising the amplifying restriction endonuclease. The first nucleic acid strand can be attached to a solid support. The first nucleic acid strand can be directly attached to a solid support. A portion of the second nucleic acid strand can hybridize with the first nucleic acid strand to form the double-stranded portion. The portion of the probe nucleic acid comprising the amplifying restriction endonuclease that is separated from the at least another portion of the probe nucleic acid in step (b) can comprise a portion of the first nucleic acid strand and all of the second strand. The portion of the probe nucleic acid comprising the amplifying restriction endonuclease that is separated from the at least another portion of the probe nucleic acid in step (b) can comprise at least a portion of the target nucleic acid.

In some cases, the method can comprise using a plurality of the probe nucleic acid in the step (a). The method can comprise using a plurality of the reporter nucleic acid in the step (c). The reporter nucleic acid in the step (c) can be in molar excess of the portion of the probe nucleic acid comprising the amplifying restriction endonuclease from the step (b). The number of molecules of the portion of the probe nucleic acid comprising the amplifying restriction endonuclease that is separated from the at least another portion of the probe nucleic acid in step (b) can be in an essentially linear relationship to the number of molecules of the target nucleic acid present in the sample. The reporter nucleic acid can be attached to a solid support. The reporter nucleic acid can be directly attached to a solid support. The reporter nucleic acid can comprise a single-stranded portion of nucleic acid. The reporter nucleic acid can comprise a label. The label can be a fluorescent label, a radioactive label, an enzyme label, or a redox label. The portion of the reporter nucleic acid that is separated from the at least another portion of the reporter nucleic acid can comprise the label. The reporter nucleic acid can comprise a first nucleic acid strand comprising the label hybridized to a second nucleic acid strand. The second nucleic acid strand can be attached to a solid support. The second nucleic acid strand can be directly attached to a solid support. A portion of the first nucleic acid strand can hybridize with the second nucleic acid strand to form the double-stranded portion of nucleic acid comprising the restriction endonuclease cut site of the amplifying restriction endonuclease. The reporter nucleic acid can comprise a third nucleic acid strand. The third nucleic acid strand can hybridize with the second nucleic acid strand to form the double-stranded portion of nucleic acid comprising the restriction endonuclease cut site of the amplifying restriction endonuclease. The reporter nucleic acid can be attached to a solid support, and the portion of the reporter nucleic acid that is separated from the at least another portion of the reporter nucleic acid and that comprises the label can be released from the solid support via the step (c). The determining step (d) can comprise detecting the label. The label can be a fluorescent label, and the determining step (d) comprises detecting the fluorescent label. The determining step (d) can comprise detecting the portion of the reporter nucleic acid separated from the at least another portion of the reporter nucleic acid using a capillary electrophoresis technique. The steps (a), (b), and (c) can be performed without nucleic acid amplification, or the steps (a), (b), (c), and (d) can be performed without nucleic acid amplification. The determining step can comprise determining the amount of the target nucleic acid present within the sample.

In another aspect, this document features a method for an organism for a genetic or epigenetic element. The method comprises, or consists essentially of, (a) contacting a sample from the mammal with a probe nucleic acid comprising an initial amplifying restriction endonuclease and a nucleotide sequence complementary to a sequence of a target nucleic acid containing the genetic or epigenetic element under conditions wherein, if the target nucleic acid is present in the sample, at least a portion of the target nucleic acid hybridizes to at least a portion of the probe nucleic acid to form a double-stranded portion of nucleic acid comprising a restriction endonuclease cut site, (b) contacting the double-stranded portion of nucleic acid with a recognition restriction endonuclease having the ability to cut the double-stranded portion of nucleic acid at the restriction endonuclease cut site under conditions wherein the recognition restriction endonuclease cleaves the double-stranded portion of nucleic acid at the restriction endonuclease cut site, thereby separating a portion of the probe nucleic acid comprising the initial amplifying restriction endonuclease from at least another portion of the probe nucleic acid, (c) contacting the portion of the probe nucleic acid comprising the initial amplifying restriction endonuclease with a first nucleic acid comprising a secondary amplifying restriction endonuclease and a double-stranded portion of nucleic acid comprising a restriction endonuclease cut site of the initial amplifying restriction endonuclease under conditions wherein the initial amplifying restriction endonuclease cleaves the first nucleic acid at the restriction endonuclease cut site of the initial amplifying restriction endonuclease, thereby separating a portion of the first nucleic acid comprising the secondary amplifying restriction endonuclease from at least another portion of the first nucleic acid, (d) contacting the portion of the first nucleic acid comprising the secondary amplifying restriction endonuclease with a second nucleic acid comprising the initial amplifying restriction endonuclease and a double-stranded portion of nucleic acid comprising a restriction endonuclease cut site of the secondary amplifying restriction endonuclease under conditions wherein the secondary amplifying restriction endonuclease cleaves the second nucleic acid at the restriction endonuclease cut site of the secondary amplifying restriction endonuclease, thereby separating a portion of the second nucleic acid comprising the initial amplifying restriction endonuclease from at least another portion of the second nucleic acid, (e) contacting the portion of the second nucleic acid comprising the initial amplifying restriction endonuclease with a reporter nucleic acid comprising a double-stranded portion of nucleic acid comprising a restriction endonuclease cut site of the initial amplifying restriction endonuclease under conditions wherein the initial amplifying restriction endonuclease cleaves the reporter nucleic acid at the restriction endonuclease cut site of the initial amplifying restriction endonuclease, thereby separating a portion of the reporter nucleic acid from at least another portion of the reporter nucleic acid, and (f) determining the presence or absence of the portion of the reporter nucleic acid, wherein the presence of the portion of the reporter nucleic acid indicates that the sample contains the target nucleic acid, thereby indicating that the organism contains the genetic or epigenetic element, and wherein the absence of the portion of the reporter nucleic acid indicates that the sample does not contain the target nucleic acid, thereby indicating that the organism does not contain the genetic or epigenetic element. The organism can be a human. The organism can be a mammal. The mammal can be selected from the group consisting of bovine, porcine, and equine species. The organism can be a plant. The plant can be selected from the group consisting of trees, flowers, shrubs, grains, grasses, and legumes. The method can comprise assessing the organism for the genetic element. The genetic element can be an allelic variant known to exist in the species of the organism. The genetic element can be a single nucleotide polymorphism. The method can comprise assessing the organism for the epigenetic element. The epigenetic element can be a methylated DNA sequence. The sample can be selected from the group consisting of blood samples, hair samples, skin samples, throat swab samples, cheek swab samples, tissue samples, cellular samples, and tumor samples. Prior to step (a), the sample can be a sample that was processed to remove non-nucleic acid material from the sample, thereby increasing the concentration of nucleic acid, if present, within the sample. The sample can be a sample that was subjected to a nucleic acid extraction technique. Prior to step (a), the sample can be a sample that was subjected to a nucleic acid amplification technique to increase the concentration of one or more nucleic acids, if present, within the sample. The sample can be a sample that was subjected to a PCR-based technique designed to amplify the target nucleic acid. Prior to step (a), the method can comprise removing non-nucleic acid material from the sample, thereby increasing the concentration of nucleic acid, if present, within the sample. The removing can comprise performing a nucleic acid extraction technique. Prior to step (a), the method can comprise performing a nucleic acid amplification technique to increase the concentration of one or more nucleic acids, if present, within the sample. The nucleic acid amplification technique can comprise a PCR-based technique designed to amplify the target nucleic acid. Prior to step (a), the method can comprise removing non-nucleic acid material from the sample, thereby increasing the concentration of nucleic acid, if present, within the sample, and performing a nucleic acid amplification technique to increase the concentration of one or more nucleic acids, if present, within the sample. The probe nucleic acid can be single-stranded probe nucleic acid. The probe nucleic acid can be attached to a solid support. The probe nucleic acid can be directly attached to a solid support. The portion of the probe nucleic acid comprising the initial amplifying restriction endonuclease can be released from the solid support via the step (b). Step (a) and step (b) can be performed in the same compartment, step (a), step (b), and step (c) can be performed in the same compartment, step (a), step (b), step (c), and step (d) can be performed in the same compartment, step (a), step (b), step (c), step (d), and step (e) can be performed in the same compartment, or step (a), step (b), step (c), step (d), step (e), and step (f) can be performed in the same compartment. Step (c) and step (d) can be performed in the same compartment. Step (a) and step (b) can be performed in a first compartment, and step (c) and step (d) can be performed in a second compartment. Step (a) and step (b) can be performed by adding the sample to a compartment comprising the probe nucleic acid and the recognition restriction endonuclease. Step (c) and step (d) can be performed by adding the portion of the probe nucleic acid comprising the initial amplifying restriction endonuclease to a compartment comprising the first nucleic acid and the second nucleic acid. The probe nucleic acid can comprise (i) a single-stranded portion comprising the nucleotide sequence complementary to the sequence of the target nucleic acid and (ii) a double-stranded portion. The probe nucleic acid can comprise a first nucleic acid strand comprising the nucleotide sequence complementary to the sequence of the target nucleic acid hybridized to a second nucleic acid strand comprising the initial amplifying restriction endonuclease. The first nucleic acid strand can be attached to a solid support. The first nucleic acid strand can be directly attached to a solid support. A portion of the second nucleic acid strand can hybridize with the first nucleic acid strand to form the double-stranded portion. The portion of the probe nucleic acid comprising the initial amplifying restriction endonuclease that is separated from the at least another portion of the probe nucleic acid in step (b) can comprise a portion of the first nucleic acid strand and all of the second strand. The portion of the probe nucleic acid comprising the initial amplifying restriction endonuclease that is separated from the at least another portion of the probe nucleic acid in step (b) can comprise at least a portion of the target nucleic acid.

In some cases, the method can comprise using a plurality of the probe nucleic acid in the step (a). The method can comprise using a plurality of the reporter nucleic acid in the step (e). The reporter nucleic acid in the step (e) can be in molar excess of the portion of the probe nucleic acid comprising the initial amplifying restriction endonuclease from the step (b). The number of molecules of the portion of the probe nucleic acid comprising the initial amplifying restriction endonuclease that is separated from the at least another portion of the probe nucleic acid in step (b) can be in an essentially linear relationship to the number of molecules of the target nucleic acid present in the sample. The first nucleic acid and the second nucleic acid can be attached to a solid support. The first nucleic acid and the second nucleic acid can be directly attached to a solid support. The first nucleic acid and the second nucleic acid can be attached to a solid support in the same compartment. The portion of the first nucleic acid comprising the secondary amplifying restriction endonuclease can be released from the solid support via the step (c). The portion of the second nucleic acid comprising the initial amplifying restriction endonuclease can be released from the solid support via the step (d). The first nucleic acid can comprise a first nucleic acid strand comprising the secondary amplifying restriction endonuclease hybridized to a second nucleic acid strand to form the double-stranded portion of nucleic acid comprising the restriction endonuclease cut site of the initial amplifying restriction endonuclease. The first nucleic acid strand can be attached to a solid support. The first nucleic acid strand can be directly attached to a solid support. The second nucleic acid strand can be attached to a solid support. The second nucleic acid strand can be directly attached to a solid support. The second nucleic acid can comprise a first nucleic acid strand comprising the initial amplifying restriction endonuclease hybridized to a second nucleic acid strand to form the double-stranded portion of nucleic acid comprising the restriction endonuclease cut site of the secondary amplifying restriction endonuclease. The first nucleic acid strand can be attached to a solid support. The first nucleic acid strand can be directly attached to a solid support. The second nucleic acid strand can be attached to a solid support. The second nucleic acid strand can be directly attached to a solid support. The reporter nucleic acid can be attached to a solid support. The reporter nucleic acid can be directly attached to a solid support. The reporter nucleic acid can comprise a single-stranded portion of nucleic acid. The reporter nucleic acid can comprise a label. The label can be a fluorescent label, a radioactive label, an enzyme label, or a redox label. The portion of the reporter nucleic acid that is separated from the at least another portion of the reporter nucleic acid can comprise the label. The reporter nucleic acid can comprise a first nucleic acid strand comprising the label hybridized to a second nucleic acid strand. The second nucleic acid strand can be attached to a solid support. The second nucleic acid strand can be directly attached to a solid support. A portion of the first nucleic acid strand can hybridize with the second nucleic acid strand to form the double-stranded portion of nucleic acid comprising the restriction endonuclease cut site of the initial amplifying restriction endonuclease. The reporter nucleic acid can comprise a third nucleic acid strand. The third nucleic acid strand can hybridize with the second nucleic acid strand to form the double-stranded portion of nucleic acid comprising the restriction endonuclease cut site of the initial amplifying restriction endonuclease. The reporter nucleic acid can be attached to a solid support, and the portion of the reporter nucleic acid that is separated from the at least another portion of the reporter nucleic acid and that comprises the label can be released from the solid support via the step (e). The determining step (f) can comprise detecting the label. The label can be a fluorescent label, and the determining step (f) can comprise detecting the fluorescent label. The determining step (f) can comprise detecting the portion of the reporter nucleic acid separated from the at least another portion of the reporter nucleic acid using a capillary electrophoresis technique. Steps (a), (b), (c), (d), and (e) can be performed without nucleic acid amplification, or steps (a), (b), (c), (d), (e), and (f) can be performed without nucleic acid amplification. The determining step can comprise determining the amount of the target nucleic acid present within the sample.

In another aspect, this document features a method for assessing an organism for a genetic or epigenetic element. The method comprises, or consists essentially of, (a) contacting a sample from the mammal with a probe nucleic acid comprising an initial amplifying restriction endonuclease and a nucleotide sequence complementary to a sequence of a target nucleic acid containing the genetic or epigenetic element under conditions wherein, if the target nucleic acid is present in the sample, at least a portion of the target nucleic acid hybridizes to at least a portion of the probe nucleic acid to form a double-stranded portion of nucleic acid comprising a restriction endonuclease cut site, (b) contacting the double-stranded portion of nucleic acid with a recognition restriction endonuclease having the ability to cut the double-stranded portion of nucleic acid at the restriction endonuclease cut site under conditions wherein the recognition restriction endonuclease cleaves the double-stranded portion of nucleic acid at the restriction endonuclease cut site, thereby separating a portion of the probe nucleic acid comprising the initial amplifying restriction endonuclease from at least another portion of the probe nucleic acid, (c) contacting the portion of the probe nucleic acid comprising the initial amplifying restriction endonuclease with a first reporter nucleic acid comprising a secondary amplifying restriction endonuclease and a double-stranded portion of nucleic acid comprising a restriction endonuclease cut site of the initial amplifying restriction endonuclease under conditions wherein the initial amplifying restriction endonuclease cleaves the first reporter nucleic acid at the restriction endonuclease cut site of the initial amplifying restriction endonuclease, thereby separating a portion of the first nucleic acid comprising the secondary amplifying restriction endonuclease from at least another portion of the first nucleic acid, (d) contacting the portion of the first reporter nucleic acid comprising the secondary amplifying restriction endonuclease with a second reporter nucleic acid comprising the initial amplifying restriction endonuclease and a double-stranded portion of nucleic acid comprising a restriction endonuclease cut site of the secondary amplifying restriction endonuclease under conditions wherein the initial amplifying restriction endonuclease cleaves the second nucleic acid at the restriction endonuclease cut site of the secondary amplifying restriction endonuclease, thereby separating a portion of the second nucleic acid comprising the initial amplifying restriction endonuclease from at least another portion of the second nucleic acid, and (e) determining the presence or absence of the portion of the first reporter nucleic acid, the second reporter nucleic acid, or both the first reporter nucleic acid and the second reporter nucleic acid, wherein the presence indicates that the sample contains the target nucleic acid, thereby indicating that the organism contains the genetic or epigenetic element, and wherein the absence indicates that the sample does not contain the target nucleic acid, thereby indicating that the organism does not contain the genetic or epigenetic element. The organism can be a human. The organism can be a mammal. The mammal can be selected from the group consisting of bovine, porcine, and equine species. The organism can be a plant. The plant can be selected from the group consisting of trees, flowers, shrubs, grains, grasses, and legumes. The method can comprise assessing the organism for the genetic element. The genetic element can be an allelic variant known to exist in the species of the organism. The genetic element can be a single nucleotide polymorphism. The method can comprise assessing the organism for the epigenetic element. The epigenetic element can be a methylated DNA sequence. The sample can be selected from the group consisting of blood samples, hair samples, skin samples, throat swab samples, cheek swab samples, tissue samples, cellular samples, and tumor samples. Prior to step (a), the sample can be a sample that was processed to remove non-nucleic acid material from the sample, thereby increasing the concentration of nucleic acid, if present, within the sample. The sample can be a sample that was subjected to a nucleic acid extraction technique. Prior to step (a), the sample can be a sample that was subjected to a nucleic acid amplification technique to increase the concentration of one or more nucleic acids, if present, within the sample. The sample can be a sample that was subjected to a PCR-based technique designed to amplify the target nucleic acid. Prior to step (a), the method can comprise removing non-nucleic acid material from the sample, thereby increasing the concentration of nucleic acid, if present, within the sample. The removing can comprise performing a nucleic acid extraction technique. Prior to step (a), the method can comprise performing a nucleic acid amplification technique to increase the concentration of one or more nucleic acids, if present, within the sample. The nucleic acid amplification technique can comprise a PCR-based technique designed to amplify the target nucleic acid. Prior to step (a), the method can comprise removing non-nucleic acid material from the sample, thereby increasing the concentration of nucleic acid, if present, within the sample, and performing a nucleic acid amplification technique to increase the concentration of one or more nucleic acids, if present, within the sample. The probe nucleic acid can be single-stranded probe nucleic acid. The probe nucleic acid can be attached to a solid support. The probe nucleic acid can be directly attached to a solid support. The portion of the probe nucleic acid comprising the initial amplifying restriction endonuclease can be released from the solid support via the step (b). Step (a) and step (b) can be performed in the same compartment, step (a), step (b), and step (c) can be performed in the same compartment, step (a), step (b), step (c), and step (d) can be performed in the same compartment, or step (a), step (b), step (c), step (d), and step (e) can be performed in the same compartment. Step (c) and step (d) can be performed in the same compartment. Step (a) and step (b) can be performed in a first compartment, and step (c) and step (d) can be performed in a second compartment. Step (a) and step (b) can be performed by adding the sample to a compartment comprising the probe nucleic acid and the recognition restriction endonuclease. Step (c) and step (d) can be performed by adding the portion of the probe nucleic acid comprising the initial amplifying restriction endonuclease to a compartment comprising the first reporter nucleic acid and the second reporter nucleic acid. The probe nucleic acid can comprise (i) a single-stranded portion comprising the nucleotide sequence complementary to the sequence of the target nucleic acid and (ii) a double-stranded portion. The probe nucleic acid can comprise a first nucleic acid strand comprising the nucleotide sequence complementary to the sequence of the target nucleic acid hybridized to a second nucleic acid strand comprising the initial amplifying restriction endonuclease. The first nucleic acid strand can be attached to a solid support. The first nucleic acid strand can be directly attached to a solid support. A portion of the second nucleic acid strand can hybridize with the first nucleic acid strand to form the double-stranded portion. The portion of the probe nucleic acid comprising the initial amplifying restriction endonuclease that is separated from the at least another portion of the probe nucleic acid in step (b) can comprise a portion of the first nucleic acid strand and all of the second strand. The portion of the probe nucleic acid comprising the initial amplifying restriction endonuclease that is separated from the at least another portion of the probe nucleic acid in step (b) can comprise at least a portion of the target nucleic acid.

In some cases, the method can comprise using a plurality of the probe nucleic acid in the step (a). The method can comprise using a plurality of the first reporter nucleic acid in the step (c). The first reporter nucleic acid in the step (c) can be in molar excess of the portion of the probe nucleic acid comprising the initial amplifying restriction endonuclease from the step (b). The method can comprise using a plurality of the second reporter nucleic acid in the step (d). The second reporter nucleic acid in the step (d) can be in molar excess of the portion of the probe nucleic acid comprising the initial amplifying restriction endonuclease from the step (b). The number of molecules of the portion of the probe nucleic acid comprising the initial amplifying restriction endonuclease that is separated from the at least another portion of the probe nucleic acid in step (b) can be in an essentially linear relationship to the number of molecules of the target nucleic acid present in the sample. The first reporter nucleic acid and the second reporter nucleic acid can be attached to a solid support. The first reporter nucleic acid and the second reporter nucleic acid can be directly attached to a solid support. The first reporter nucleic acid and the second reporter nucleic acid can be attached to a solid support in the same compartment. The portion of the first reporter nucleic acid comprising the secondary amplifying restriction endonuclease can be released from the solid support via the step (c). The portion of the second reporter nucleic acid comprising the initial amplifying restriction endonuclease can be released from the solid support via the step (d). The first reporter nucleic acid can comprise a label. The label can be a fluorescent label, a radioactive label, an enzyme label, or a redox label. The second reporter nucleic acid can comprise a label. The label can be a fluorescent label, a radioactive label, an enzyme label, or a redox label. The first reporter nucleic acid and the second reporter nucleic acid can comprise a label. The first reporter nucleic acid and the second reporter nucleic acid can comprise the same label. The label can be a fluorescent label, a radioactive label, an enzyme label, or a redox label. The first reporter nucleic acid can be attached to a solid support, the portion of the first reporter nucleic acid that is separated from the at least another portion of the first reporter nucleic acid can comprise a label, and the portion of the first reporter nucleic acid that is separated from the at least another portion of the first reporter nucleic acid and that comprises the label can be released from the solid support via the step (c). The first reporter nucleic acid can comprise a first nucleic acid strand comprising the secondary amplifying restriction endonuclease hybridized to a second nucleic acid strand to form the double-stranded portion of nucleic acid comprising the restriction endonuclease cut site of the initial amplifying restriction endonuclease. The first nucleic acid strand can be attached to a solid support. The first nucleic acid strand can be directly attached to a solid support. The second nucleic acid strand can be attached to a solid support. The second nucleic acid strand can be directly attached to a solid support. The first nucleic acid strand can comprise a label. The label can be a fluorescent label, a radioactive label, an enzyme label, or a redox label. The second nucleic acid strand can comprise a label. The label can be a fluorescent label, a radioactive label, an enzyme label, or a redox label. The second reporter nucleic acid can be attached to a solid support, the portion of the second reporter nucleic acid that is separated from the at least another portion of the second reporter nucleic acid can comprise a label, and the portion of the second reporter nucleic acid that is separated from the at least another portion of the second reporter nucleic acid and that comprises the label can be released from the solid support via the step (d). The second reporter nucleic acid can comprise a first nucleic acid strand comprising the initial amplifying restriction endonuclease hybridized to a second nucleic acid strand to form the double-stranded portion of nucleic acid comprising the restriction endonuclease cut site of the secondary amplifying restriction endonuclease. The first nucleic acid strand can be attached to a solid support. The first nucleic acid strand can be directly attached to a solid support. The second nucleic acid strand can be attached to a solid support. The second nucleic acid strand can be directly attached to a solid support. The first nucleic acid strand can comprise a label. The label can be a fluorescent label, a radioactive label, an enzyme label, or a redox label. The second nucleic acid strand can comprise a label. The label can be a fluorescent label, a radioactive label, an enzyme label, or a redox label. The portion of the first reporter nucleic acid separated from the at least another portion of the first reporter nucleic acid can comprise a fluorescent label, the portion of the second reporter nucleic acid separated from the at least another portion of the second reporter nucleic acid can comprise a fluorescent label, and the determining step (e) can comprise detecting the fluorescent label. The determining step (e) can comprise detecting the portion of the first reporter nucleic acid separated from the at least another portion of the first reporter nucleic acid using a capillary electrophoresis technique. The determining step (e) can comprise detecting the portion of the second reporter nucleic acid separated from the at least another portion of the second reporter nucleic acid using a capillary electrophoresis technique. Steps (a), (b), (c), and (d) can be performed without nucleic acid amplification, or steps (a), (b), (c), (d), and (e) can be performed without nucleic acid amplification. The determining step can comprise determining the amount of the target nucleic acid present within the sample.

In another aspect, this document features a kit for assessing an organism for a genetic or epigenetic element. The kit comprises, or consists essentially of, a probe nucleic acid comprising an amplifying restriction endonuclease and a nucleotide sequence complementary to a sequence of a target nucleic acid containing the genetic or epigenetic element, wherein at least a portion of the target nucleic acid is capable of hybridizing to at least a portion of the probe nucleic acid to form a double-stranded portion of nucleic acid comprising a restriction endonuclease cut site. The probe nucleic acid can be single-stranded probe nucleic acid. The kit can comprise a solid support, and the probe nucleic acid can be attached to the solid support. A portion of the probe nucleic acid comprising the amplifying restriction endonuclease can be releasable from the solid support via cleavage with a recognition restriction endonuclease having the ability to cleave at the restriction endonuclease cut site. The kit can further comprise the recognition restriction endonuclease. The probe nucleic acid can comprise (i) a single-stranded portion comprising the nucleotide sequence complementary to the sequence of the target nucleic acid and (ii) a double-stranded portion. The probe nucleic acid can comprise a first nucleic acid strand comprising the nucleotide sequence complementary to the sequence of the target nucleic acid hybridized to a second nucleic acid strand comprising the amplifying restriction endonuclease. The kit can further comprise a reporter nucleic acid comprising a double-stranded portion of nucleic acid comprising a restriction endonuclease cut site of the amplifying restriction endonuclease. The kit can comprise a solid support, and the reporter nucleic acid can be attached to the solid support. The reporter nucleic acid can be directly attached to the solid support. The reporter nucleic acid can comprise a single-stranded portion of nucleic acid. The reporter nucleic acid can comprise a label. The label can be a fluorescent label, a radioactive label, an enzyme label, or a redox label. A portion of the reporter nucleic acid comprising the label can be capable of being separated from at least another portion of the reporter nucleic acid via cleavage by the amplifying restriction endonuclease. The reporter nucleic acid can comprise a first nucleic acid strand comprising the label hybridized to a second nucleic acid strand. The kit can further comprise: (a) a first signal expansion nucleic acid comprising a secondary amplifying restriction endonuclease and a double-stranded section having a restriction endonuclease cut site for the amplifying restriction endonuclease, and (b) a second signal expansion nucleic acid comprising the amplifying restriction endonuclease and a double-stranded section having a restriction endonuclease cut site for the secondary amplifying restriction endonuclease. The probe nucleic acid can be lyophilized. All the ingredients of the kit can be lyophilized or dry.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references (e.g., GenBank® records) mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 4 is a schematic of an exemplary configuration of first signal expansion nucleic acid and second signal expansion nucleic acid that can be used with the methods and materials provided herein for detecting target nucleic acid. Such first signal expansion nucleic acid and second signal expansion nucleic acid can be used with or without reporter nucleic acid. When used without a separate reporter nucleic acid step, such signal expansion nucleic acid can be referred to as reporter nucleic acid.

FIG. 11 contains a double stranded section of DNA (SEQ ID NO:1) that contains the recognition site and cleavage site for a FokI restriction endonuclease.

DETAILED DESCRIPTION

Figure 1:
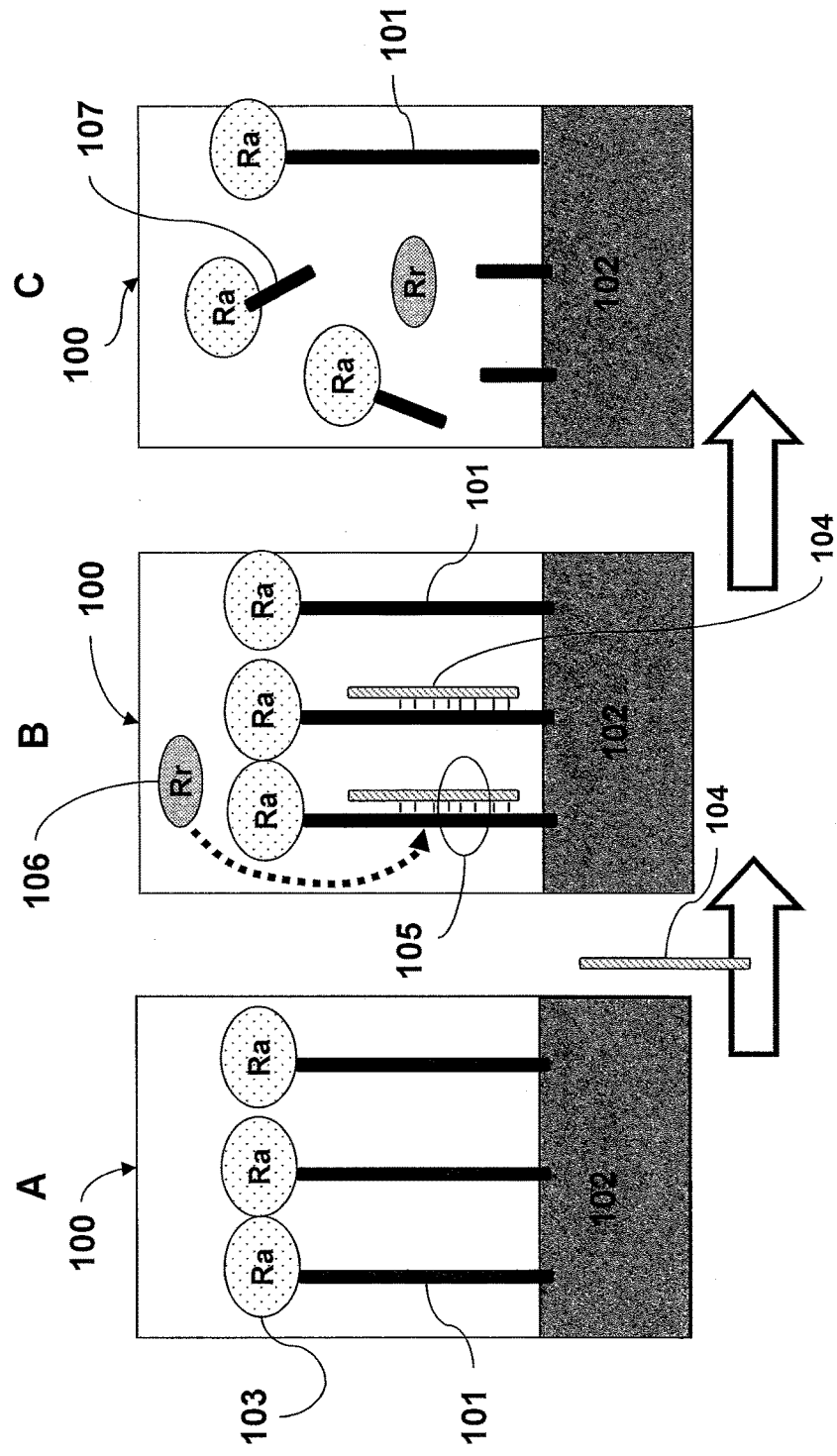
FIG. 1 is a schematic depicting an exemplary method for detecting target nucleic acid using probe nucleic acid, a recognition restriction endonuclease, and reporter nucleic acid.

This document provides methods and materials for detecting genetic and/or epigenetic elements. For example, this document relates to methods and materials involved in using an enzymatic amplification cascade of restriction endonucleases to detect genetic and/or epigenetic elements present within an organism (e.g., a human). In some cases, this document provides methods and materials for detecting target nucleic acid that contains a genetic element or epigenetic element. For example, this document provides methods and materials for detecting the presence or absence of target nucleic acid (e.g., target nucleic acid containing a particular genetic element) in an organism's genome, methods and materials for detecting the presence or absence of target nucleic acid that contains an epigenetic element (e.g., methylated DNA) in a cell of an organism, kits for detecting the presence or absence of target nucleic acid (e.g., target nucleic acid containing a particular genetic element) in an organism's genome, kits for detecting the presence or absence of target nucleic acid that contains an epigenetic element (e.g., methylated DNA) in a cell of an organism, and methods for making such kits.

Any type of organism (e.g., plant or animal) can be assessed using the methods and materials provided herein to determine whether or not the organism contains a genetic and/or epigenetic element. Examples of organisms that can be assessed using the methods and materials provided herein to determine whether or not the organism contains a genetic and/or epigenetic element include, without limitation, plants (e.g., trees, flowers, shrubs, grains, grasses, and legumes), mammals (e.g., humans, dogs, cats, cows, horses, pigs, sheep, goats, monkeys, buffalo, bears, whales, and dolphins), avian species (e.g., chickens, turkeys, ostrich, emus, cranes, and falcons), and non-mammalian animals (e.g., mollusks, frogs, lizards, snakes, and insects). For example, plant crops such as corn, soybeans, wheat, and rice can be assessed for the presence or absence of genetic elements such as possible introduced transgenes, transposable elements, or polymorphisms.

Any type of biological sample can be used with the methods and materials provided herein to assess an organism for a particular genetic or epigenetic element. For example, any type of biological sample that is obtained from an organism to be tested and that contains the organism's nucleic acid (e.g., potentially methylated nucleic acid or genomic DNA) can be used as described herein. Examples of samples that can be used as described herein include, without limitation, blood samples (e.g., 50 mL collection of a patient's blood), serum samples, hair samples, skin samples, tissue samples (e.g., tissue biopsy samples), bone marrow samples, tumor samples, amniotic fluid samples, throat or cheek swab samples (e.g., a buccal smear sample), and mouthwash samples. In some cases, a sample used herein can be a serum sample prepared from whole blood such that circulating DNA is present in the sample as described elsewhere (Sunami et al., *Methods Mol. Biol.*, 507:349-56 (2009)).

The methods and materials provided herein can be used to assess an organism for any type of genetic or epigenetic element. Examples of possible genetic elements that can be assessed using the methods and materials provided herein include, without limitation, wild-type or common standard allele sequences of an organism's species, mutant or uncommon allele sequences of an organism's species, sequence insertions, sequence deletions, sequence substitutions, polymorphisms, SNPs, or combinations thereof. Examples of possible epigenetic elements that can be assessed using the methods and materials provided herein include, without limitation, methylated DNA. In some cases, an organism can be assessed for one or more of the genetic or epigenetic elements listed in Table 1 using the methods and materials provided herein. When designing a method for detecting a genetic or epigenetic element listed in Table 1, a probe nucleic acid can be designed that is complementary to a portion of any of the indicated sequences from Table 1. For example, when designing a method for detecting a single nucleotide polymorphism (SNP) in the human thiopurine S-methyltransferase gene (Ensemble gene ID ENSG00000137364; Chromosome 6: 18,128,542-18,155,305 reverse strand), a probe nucleic acid can be designed that is complementary to a portion that includes positions 18143896-18143901 of the sequence. In some cases, one or more of the DNA methylation events described elsewhere (e.g., Szyf, *Ageing Res. Rev.*, 2(3):299-328 (2003); Di Gioia et al., *BMC Cancer*, 6:89 (2006); Maruya et al., *Clin. Cancer Res.*, 10:3825 (2004); Fischer et al., *Lung Cancer*, 56:115-123 (2007); Yeo et al., *Pathology*, 37:125-130 (2005); Allen Chan et al., *Clin. Chem.*, 10:1373 (2008); Wang et al., *Lung Cancer*, 56:289-294 (2007); and Widschwendter et al., *PLoS ONE*, 3(7):e2656 (2008)) can be detected using the methods and materials provided herein, for example, to provide information about conditions such as carcinogenesis or tumor metastasis.

TABLE 1

Types of genetic or epigenetic elements that can be detected.

| Organism | Genetic or Epigenetic Element | Possible Associated Condition |
| --- | --- | --- |
| Human | C825T polymorphism of the GNB3 | Glioblastoma |
| Human | RASSF2A | Cancers |
| Human | MGMT | Cancers |
| Human | Cyclins D1 and D2 (CCDN1 and CCDN2) | Cancers |
| Human | HOXA10 | Ovarian cancer |
| Human | thiopurine S-methyltransferase | Drug toxicity |
| Human | APP, PS1, and PS2 inheritance of the APOE4 allele confers increased risk for AD | Alzheimer's Disease |
| Human | MTCYB gene | Parkinson disease |
| Human | Congenital heart disease (CHD) | |
| Human | CHDS1, Chromosome: 16; Location: 16pter-p13, GeneID: 338334 | Coronary heart disease |
| Human | PARK7, Chromosome: 1; Location: 1p36.23, GeneID: 11315 | Parkinson disease |
| Human | BRCA1, BRCA2 | Breast cancer |
| Human | BCL2 | Cancers |
| Human | IL2 | Cancers |
| Human | CFTR | Cystic Fibrosis |
| Human | TSC2 | Tuberous sclerosis |
| Human | APP | Alzheimer's Disease |
| Human | NPPB | Cardiovascular disease |
| Human | LEP | Obesity |
| Human | OSM | Leukemia |
| Human | MCM6 | lactose intolerance |
| Horse | LAMA3 | skin blistering disease |
| Cow | DGAT1 | Milk Production |
| Dog | EPM2A | Epilepsy |

In one embodiment, a method for assessing an organism for a genetic or epigenetic element can include determining whether or not a biological sample obtained from the organism contains a target nucleic acid having the genetic or epigenetic element of interest. For example, a biological sample (e.g., a blood sample to be tested) can be placed in contact with probe nucleic acid. The probe nucleic acid can be designed to have a single-stranded portion with a nucleotide sequence that is complementary to at least a portion of the target nucleic acid to be detected. In this case, target nucleic acid present within the sample can hybridize with the complementary sequence of this single-stranded portion of the probe nucleic acid to form a double-stranded section with one strand being target nucleic acid and the other strand being probe nucleic acid. In addition, the single-stranded portion of the probe nucleic acid having the nucleotide sequence that is complementary to at least a portion of the target nucleic acid to be detected can be designed such that hybridization with the target nucleic acid creates a restriction endonuclease cut site. Thus, target nucleic acid present within the sample can hybridize with the complementary sequence of the single-stranded portion of the probe nucleic acid to form a double-stranded section that creates a cut site for a restriction endonuclease. This cut site created by the hybridization of target nucleic acid to probe nucleic acid can be referred to as a recognition restriction endonuclease cut site. In addition, a restriction endonuclease that cleaves nucleic acid at such a recognition restriction endonuclease cut site can be referred to as a recognition restriction endonuclease.

The probe nucleic acid also can be designed to contain a restriction endonuclease. This restriction endonuclease, which can be a component of the probe nucleic acid, can be referred to as an amplifying restriction endonuclease. An amplifying restriction endonuclease is typically a different restriction endonuclease than the restriction endonuclease that is used as a recognition restriction endonuclease. For example, when an EcoRI restriction endonuclease is used as a recognition restriction endonuclease, a restriction endonuclease other than an EcoRI restriction endonuclease (e.g., a Hind III restriction endonuclease) is used as an amplifying restriction endonuclease. Thus, in general, probe nucleic acid is designed to contain an amplifying restriction endonuclease and to have a nucleotide sequence such that the target nucleic acid can hybridize to the probe nucleic acid and create a recognition restriction endonuclease cut site for a recognition restriction endonuclease. In some cases, the probe nucleic acid can be attached to a solid support (e.g., a well of a microtiter plate). For example, the probe nucleic acid can be attached to a solid support such that cleavage at the recognition restriction endonuclease cut site via the recognition restriction endonuclease releases a portion of the probe nucleic acid that contains the amplifying restriction endonuclease.

After contacting the sample (e.g., a biological sample) that may or may not contain target nucleic acid with the probe nucleic acid that is attached to a solid support, the target nucleic acid, if present in the sample, can hybridize to the probe nucleic acid and create the recognition restriction endonuclease cut site. At this point, the recognition restriction endonuclease, whether added to the reaction or already present in the reaction, can cleave the probe nucleic acid at the recognition restriction endonuclease cut sites that are formed by the hybridization of target nucleic acid to the probe nucleic acid, thereby releasing the portion of the probe nucleic acid that contains the amplifying restriction endonuclease from the solid support. The number of amplifying restriction endonuclease-containing portions of the probe nucleic acid that are released from the solid support can be in an essentially linear relationship (e.g., essentially a one-for-one relationship) with the number of target nucleic acid molecules that hybridize with the probe nucleic acid to form the recognition restriction endonuclease cut site.

The portions of the probe nucleic acid containing the amplifying restriction endonuclease that were released from the solid support can be collected and placed in contact with reporter nucleic acid. For example, the released portions of the probe nucleic acid, if present, can be transferred from one well of a microtiter plate (e.g., a 96-well plate) that contained the probe nucleic acid to another well of a microtiter plate that contains the reporter nucleic acid. The reporter nucleic acid can be designed to have a double-stranded portion with a restriction endonuclease cut site for the amplifying restriction endonuclease of the probe nucleic acid. This restriction endonuclease cut site for the amplifying restriction endonuclease can be referred to as an amplifying restriction endonuclease cut site. If portions of the probe nucleic acid containing the amplifying restriction endonuclease are present and placed in contact with the reporter nucleic acid, then the reporter nucleic acid can be cleaved at the amplifying restriction endonuclease cut site by the amplifying restriction endonuclease. Since the amplifying restriction endonucleases of the released portions of the probe nucleic acid are free to carry out repeated cleavage events, the number of reporter nucleic acid molecules that are cleaved can greatly exceed the number of amplifying restriction endonucleases present in the reaction. For example, the number of cleaved reporter nucleic acid molecules can greatly exceed (e.g., exponentially exceed) the number of amplifying restriction endonucleases present in the reaction and therefore can greatly exceed (e.g., exponentially exceed) the number of target nucleic acid molecules that were present in the sample contacted with the probe nucleic acid. Such a greatly expanded relationship (e.g., an exponential relationship) can allow very small amounts of target nucleic acid present in the sample to be readily detected.

After the released portions of the probe nucleic acid, if present, are contacted with the reporter nucleic acid, the presence or absence of cleaved reporter nucleic acid can be determined. The presence of cleaved reporter nucleic acid can indicate that the sample contained the target nucleic acid, thereby indicating that the sample contained the target genetic or epigenetic element for which the sample is being tested, while the absence of cleaved reporter nucleic acid can indicate that the sample lacked the target nucleic acid, thereby indicating that the sample lacked the target genetic or epigenetic element for which the sample is being tested. In some cases, the amount of cleaved reporter nucleic acid can be determined. In such cases, the amount of cleaved reporter nucleic acid can indicate the amount of target nucleic acid present in the sample, which can indicated the relative amount of the genetic or epigenetic element present in the organism being tested. A standard curve using known amounts of target nucleic acid can be used to aid in the determination of the amount of target nucleic acid present within a sample. For example, genomic DNA from known heterozygous and/or homozygous (e.g., homozygous for a particular genetic element being tested for) organisms can be included in an assay to determine whether a genomic DNA sample from an organism being tested contains zero, one, or two copies of a particular target nucleic acid for which the organism is being tested based on the amount of cleaved reporter nucleic acid.

In some cases, the reporter nucleic acid can contain a label to aid in the detection of cleaved reporter nucleic acid. For example, reporter nucleic acid can contain a fluorescent label and a quencher such that cleaved reporter nucleic acid provides a fluorescent signal and uncleaved reporter nucleic acid does not provide a fluorescent signal. In some cases, the reporter nucleic acid can contain a label (e.g., a colorimetric label, a fluorescent label or an enzyme (e.g., a redox enzyme) such as horse radish peroxidase) and can be attached to a solid support (e.g., a well of a microtiter plate). For example, the reporter nucleic acid can be attached to a solid support such that cleavage at the amplifying restriction endonuclease cut site by the amplifying restriction endonuclease releases a portion of the reporter nucleic acid that contains the label. The resulting reaction mixture can be collected and assessed for the presence, absence, or amount of released portions of the reporter nucleic acid using the label. For example, the released portions of the reporter nucleic acid, if present, can be transferred from one well of a microtiter plate (e.g., a 96-well plate) that contained the reporter nucleic acid to another well of a microtiter plate, where the transferred material can be assessed for a signal from the label.

One example of a method of detecting target nucleic acid that includes using probe nucleic acid and reporter nucleic acid is set forth in FIG. 1. With reference to FIG. 1, first reaction chamber 100 (e.g., a microtiter plate well) can contain probe nucleic acid 101. Probe nucleic acid 101 can be attached (e.g., immobilized) to solid support 102 and can include amplifying restriction endonuclease 103 (Ra). Probe nucleic acid 101 can be attached to solid support 102 such that amplifying restriction endonuclease 103 is released from solid support 102 upon cleavage of a nucleic acid component of probe nucleic acid 101. Probe nucleic acid 101 can have a single-stranded section having a nucleotide sequence that is complementary to at least a portion of target nucleic acid 104. Probe nucleic acid 101 can be contacted with a sample that may or may not contain target nucleic acid 104. If target nucleic acid 104 is present, at least a portion of target nucleic acid 104 and probe nucleic acid 101 can hybridize to form a double-stranded section of nucleic acid. Such a double-stranded section can contain at least one recognition restriction endonuclease cut site 105. Addition of recognition restriction endonuclease 106 (Rr) to first reaction chamber 100 can result in the cleave of probe nucleic acid 101 at recognition restriction endonuclease cut site 105 formed by one strand of probe nucleic acid and one strand of target nucleic acid, thereby releasing portion 107 of probe nucleic acid 101 from solid support 102. Portion 107 can include amplifying restriction endonuclease 103.

The reaction product from first reaction chamber 100 containing released portion 107, if target nucleic acid 104 was present, can be transferred (e.g., manually or automatically) to second reaction chamber 120. Second reaction chamber 120 can contain reporter nucleic acid 121. Reporter nucleic acid 121 can be attached (e.g., immobilized) to solid support 122 and can include marker (e.g., a label) 123 (M). Reporter nucleic acid 121 can be attached to solid support 122 such that marker 123 is released from solid support 122 upon cleavage of a nucleic acid component of reporter nucleic acid 121. Reporter nucleic acid 121 can have at least one double-stranded portion that contains at least one amplifying restriction endonuclease cut site 124. Addition of the reaction product from first reaction chamber 100 to second reaction chamber 120 can result in the cleavage of reporter nucleic acid 121 at amplifying restriction endonuclease cut site 124 if the reaction product contains portion 107. Such cleavage of reporter nucleic acid 121 can result in the release of portion 127 from solid support 122. Portion 127 can include marker 123.

The reaction product from second reaction chamber 120 can be assessed to determine the presence, absence, or amount of portion 127. The presence of portion 127 can indicate that the sample contained target nucleic acid 104, while the absence of portion 127 can indicate that the sample lacked target nucleic acid 104. In some cases, the amount of portion 127 can be determined. In such cases, the amount of portion 127 can indicate the amount of target nucleic acid 104 present in the sample. The presence, absence, or amount of portion 127 can be determined using marker 123, and portion 127 having marker 123 can be distinguished from uncleaved reporter nucleic acid 121 having marker 123 since, in this example, portion 127 is released from solid support 122, while uncleaved reporter nucleic acid 121 remains attached to solid support 122. For example, in some cases, the reaction product from second reaction chamber 120 can be transferred to third reaction chamber where the presence or absence of portion 127 via marker 123 is assessed. If portion 127 is present, the amount of portion 127 present can be quantified.

Figure 2:
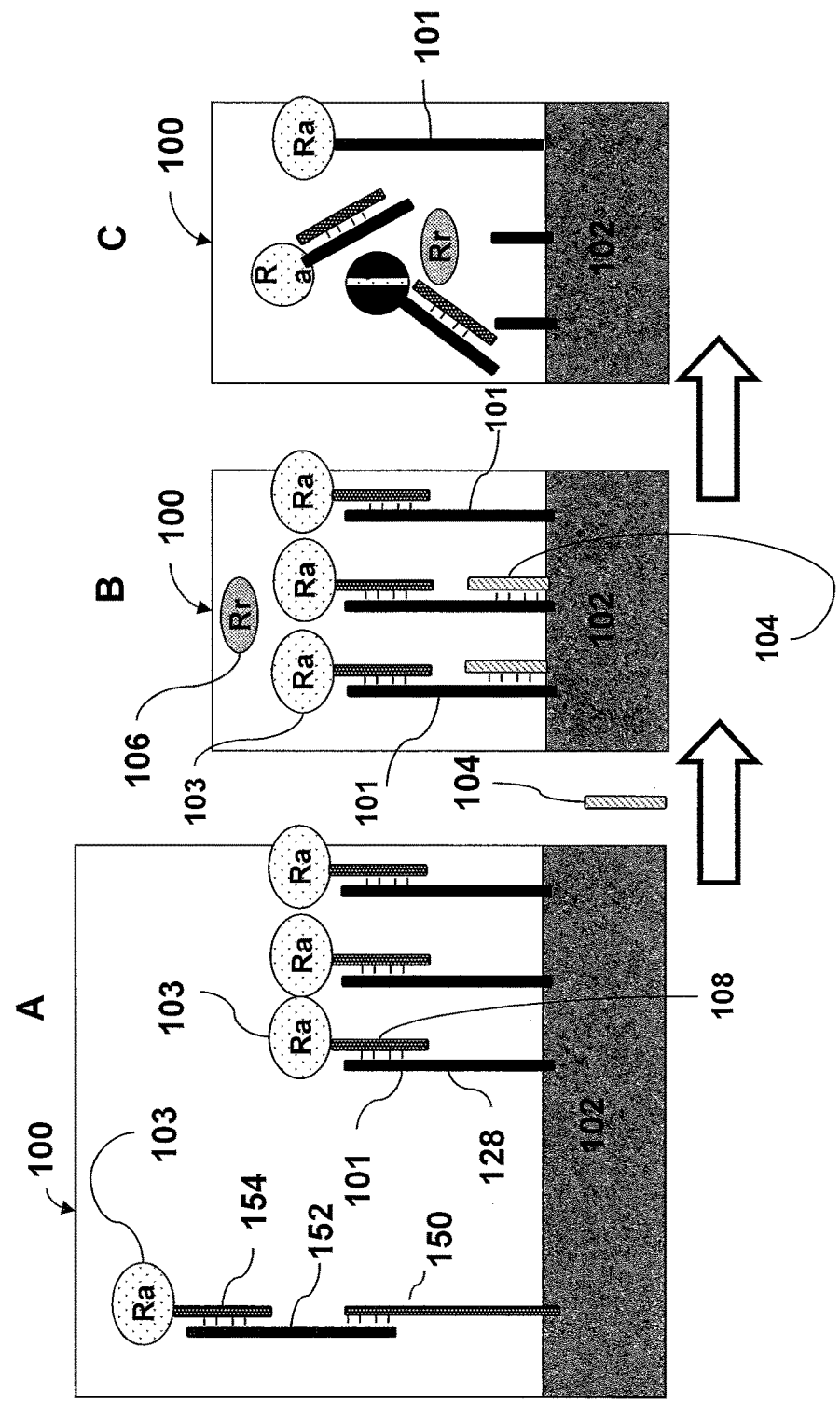
FIG. 2 is a schematic of an exemplary configuration of probe nucleic acid that can be used with the methods and materials provided herein for detecting target nucleic acid.

Probe nucleic acid 101 and reporter nucleic acid 121 can have various configurations. For example, with reference to FIG. 1, probe nucleic acid 101 can be designed to have a single nucleic acid strand such that the entire nucleic acid component of probe nucleic acid 101 is single-stranded prior to contact with target nucleic acid 104. In another example, with reference to FIG. 2, probe nucleic acid 101 can be designed to have first strand 128 and second strand 108. First strand 128 can be attached to solid support 102 and can be designed to have a single-stranded section having a nucleotide sequence that is complementary to at least a portion of target nucleic acid 104. Second strand 108 can include amplifying restriction endonuclease 103 and can have a single-stranded section having a nucleotide sequence that can hybridize to first strand 128. In some cases, first strand 128 and second strand 108 can be synthesized or obtained separately and then mixed together to form probe nucleic acid 101. For example, first strand 128 can be synthesized, biotinylated, and attached to a streptavidin-coated solid support. After synthesizing the nucleic acid component of second strand 108 and attaching amplifying restriction endonuclease 103 to the synthesized nucleic acid component, second strand 108 can be incubated with first strand 128 to form nucleic acid probe 101. In some cases, probe nucleic acid 101 can contain more than two strands. For example, probe nucleic acid can include first strand 150, second strand 152, and third strand 154. In this case, first strand 150 can be attached to solid support 102, second strand 152 can be hybridized to first strand 150 and can include a single-stranded section having a nucleotide sequence that is complementary to at least a portion of target nucleic acid 104, and third strand 154 can be hybridized to second strand 152 and can be attached to amplifying restriction endonuclease 103. Similar one, two, three, or more strand configurations can be used to make reporter nucleic acid.

In another embodiment, a method for detecting target nucleic acid can include contacting a sample (e.g., a biological sample to be tested) with probe nucleic acid. The probe nucleic acid can be designed to have a single-stranded portion with a nucleotide sequence that is complementary to at least a portion of the target nucleic acid to be detected. In this case, target nucleic acid present within the sample can hybridize with the complementary sequence of this single-stranded portion of the probe nucleic acid to form a double-stranded section with one strand being target nucleic acid and the other strand being probe nucleic acid. In addition, the single-stranded portion of the probe nucleic acid having the nucleotide sequence that is complementary to at least a portion of the target nucleic acid to be detected can be designed such that hybridization with the target nucleic acid creates a recognition restriction endonuclease cut site. Thus, target nucleic acid present within the sample can hybridize with the complementary sequence of the single-stranded portion of the probe nucleic acid to form a double-stranded section that creates a recognition restriction endonuclease cut site for a recognition restriction endonuclease. The probe nucleic acid also can be designed to contain an amplifying restriction endonuclease. Since this method includes the use of two or more different amplifying restriction endonucleases, the amplifying restriction endonuclease that is a component of the probe nucleic acid can be referred to as a first or an initial amplifying restriction endonuclease, with additional amplifying restriction endonucleases being referred to as second, third, and so on or secondary, tertiary, and so on amplifying restriction endonucleases. This initial amplifying restriction endonuclease is typically a different restriction endonuclease than the restriction endonuclease that is used as a recognition restriction endonuclease. For example, when an EcoRI restriction endonuclease is used as a recognition restriction endonuclease, a restriction endonuclease other than an EcoRI restriction endonuclease (e.g., a Hind III restriction endonuclease) is used as an initial amplifying restriction endonuclease. Thus, in general, probe nucleic acid is designed to contain an initial amplifying restriction endonuclease and to have a nucleotide sequence such that the target nucleic acid can hybridize to the probe nucleic acid and create a recognition restriction endonuclease cut site for a recognition restriction endonuclease. In some cases, the probe nucleic acid can be attached to a solid support (e.g., a well of a microtiter plate). For example, the probe nucleic acid can be attached to a solid support such that cleavage at the recognition restriction endonuclease cut site via the recognition restriction endonuclease releases a portion of the probe nucleic acid that contains the initial amplifying restriction endonuclease.

After contacting the sample that may or may not contain target nucleic acid with the probe nucleic acid that is attached to a solid support, the target nucleic acid, if present in the sample, can hybridize to the probe nucleic acid and create the recognition restriction endonuclease cut site. At this point, the recognition restriction endonuclease, whether added to the reaction or already present in the reaction, can cleave the probe nucleic acid at the recognition restriction endonuclease cut sites that are formed by the hybridization of target nucleic acid to the probe nucleic acid, thereby releasing the portion of the probe nucleic acid that contains the initial amplifying restriction endonuclease from the solid support. The number of initial amplifying restriction endonuclease-containing portions of the probe nucleic acid that are released from the solid support can be in an essentially linear relationship (e.g., essentially a one-for-one relationship) with the number of target nucleic acid molecules that hybridize with the probe nucleic acid to form the recognition restriction endonuclease cut site.

The portions of the probe nucleic acid containing the initial amplifying restriction endonuclease that were released from the solid support can be collected and placed in contact with first signal expansion nucleic acid and second signal expansion nucleic acid. The first signal expansion nucleic acid can be designed to have a double-stranded portion with a restriction endonuclease cut site for the initial amplifying restriction endonuclease of the probe nucleic acid. This restriction endonuclease cut site for the initial amplifying restriction endonuclease can be referred to as an initial amplifying restriction endonuclease cut site. The first signal expansion nucleic acid also can be designed to contain a secondary amplifying restriction endonuclease. The second signal expansion nucleic acid can be designed to have a double-stranded portion with a restriction endonuclease cut site for the secondary amplifying restriction endonuclease of the first signal expansion nucleic acid. This restriction endonuclease cut site for the secondary amplifying restriction endonuclease can be referred to as a secondary amplifying restriction endonuclease cut site. The second signal expansion nucleic acid also can be designed to contain an initial amplifying restriction endonuclease. For example, when an EcoRI restriction endonuclease is used as a recognition restriction endonuclease and a HindIII restriction endonuclease is used as an initial amplifying restriction endonuclease of the probe nucleic acid, a SmaI restriction endonuclease can be used as a secondary amplifying restriction endonuclease of the first signal expansion nucleic acid and a HindIII restriction endonuclease can be used as the initial amplifying restriction endonuclease of the second signal expansion nucleic acid.

In some cases, the first signal expansion nucleic acid and second signal expansion nucleic acid can be attached to a solid support (e.g., a well of a microtiter plate). For example, the first signal expansion nucleic acid can be attached to a solid support such that cleavage at the initial amplifying restriction endonuclease cut site via the initial amplifying restriction endonuclease releases a portion of the first signal expansion nucleic acid that contains the secondary amplifying restriction endonuclease, and the second signal expansion nucleic acid can be attached to a solid support such that cleavage at the secondary amplifying restriction endonuclease cut site via the secondary amplifying restriction endonuclease releases a portion of the second signal expansion nucleic acid that contains the initial amplifying restriction endonuclease. The first signal expansion nucleic acid can be attached to the same solid support (e.g., two different sub-compartments of a larger compartment) that contains the second signal expansion nucleic acid provided that the secondary amplifying restriction endonuclease of uncleaved first signal expansion nucleic acid is unable to cleave the second signal expansion nucleic acid and provided that the initial amplifying restriction endonuclease of uncleaved second signal expansion nucleic acid is unable to cleave the first signal expansion nucleic acid. In some cases, the first signal expansion nucleic acid can be attached to the same solid support within a joint compartment such that the first signal expansion nucleic acid is within a first compartment of the joint compartment and the second signal expansion nucleic acid is within a second compartment of the joint compartment. In such cases, the secondary amplifying restriction endonuclease of uncleaved first signal expansion nucleic acid in the first compartment is unable to cleave the second signal expansion nucleic acid located in the second compartment, while the secondary amplifying restriction endonuclease of cleaved first signal expansion nucleic acid is capable of moving (e.g., diffusing) from the first compartment to the second compartment to cleave the second signal expansion nucleic acid located in the second compartment. In addition, the initial amplifying restriction endonuclease of uncleaved second signal expansion nucleic acid in the second compartment is unable to cleave the first signal expansion nucleic acid located in the first compartment, while the initial amplifying restriction endonuclease of cleaved second signal expansion nucleic acid is capable of moving (e.g., diffusing) from the second compartment to the first compartment to cleave the first signal expansion nucleic acid located in the first compartment.

If portions of the probe nucleic acid containing the initial amplifying restriction endonuclease are present and placed in contact with the first signal expansion nucleic acid, then the first signal expansion nucleic acid can be cleaved at the initial amplifying restriction endonuclease cut site by the initial amplifying restriction endonuclease, thereby releasing a portion of the first signal expansion nucleic acid that contains the secondary amplifying restriction endonuclease from the solid support. The released portions of the first signal expansion nucleic acid containing the secondary amplifying restriction endonuclease can be free to cleave the second signal expansion nucleic acid at the secondary amplifying restriction endonuclease cut site, thereby releasing a portion of the second signal expansion nucleic acid that contains the initial amplifying restriction endonuclease from the solid support. Since the initial amplifying restriction endonucleases of the released portions of the probe nucleic acid, the initial amplifying restriction endonucleases of the released portions of the second signal expansion nucleic acid, and the secondary amplifying restriction endonucleases of the released portions of the first signal expansion nucleic acid are free to carry out repeated cleavage events, the number of released portions containing the initial amplifying restriction endonucleases is greatly increased from the number that were released by the recognition restriction endonuclease. For example, the number of cleaved first signal expansion nucleic acid molecules can greatly exceed (e.g., exponentially exceed) the number of released portions of the probe nucleic acid, and the number of cleaved second signal expansion nucleic acid molecules can greatly exceed (e.g., exponentially exceed) the number of released portions of the probe nucleic acid. Such a greatly expanded relationship (e.g., an exponential relationship) can allow very small amounts of target nucleic acid present in the sample to be readily detected.

In some cases, this method can be performed with the first signal expansion nucleic acid being attached to a solid support that is different from the solid support that contains the second signal expansion nucleic acid. For example, the first signal expansion nucleic acid can be attached to one well of a microtiter plate, while the second signal expansion nucleic acid can be attached to a different well of a microtiter plate. In this case, the resulting reaction material from the well with the first signal expansion nucleic acid can be collected and transferred to the well containing the second signal expansion nucleic acid.

The portions of the second signal expansion nucleic acid containing the initial amplifying restriction endonuclease that were released from the solid support containing the second signal expansion nucleic acid along with any other released portions in this reaction (e.g., the released portions of the probe nucleic acid containing the initial amplifying restriction endonuclease and the released portions of the first signal expansion nucleic acid containing the secondary amplifying restriction endonuclease) can be collected and placed in contact with reporter nucleic acid. For example, the released portions, if present, can be transferred from one well of a microtiter plate (e.g., a 96-well plate) that contained the second signal expansion nucleic acid to another well of a microtiter plate that contains the reporter nucleic acid. The reporter nucleic acid can be designed to have a double-stranded portion with a restriction endonuclease cut site for the initial amplifying restriction endonuclease. If released portions containing the initial amplifying restriction endonuclease are present and placed in contact with the reporter nucleic acid, then the reporter nucleic acid can be cleaved at the initial amplifying restriction endonuclease cut site by the initial amplifying restriction endonuclease. Since the initial amplifying restriction endonucleases of the released portions are free to carry out repeated cleavage events, the number of reporter nucleic acid molecules that are cleaved can greatly exceed the number of initial amplifying restriction endonucleases present in the reaction. For example, the number of cleaved reporter nucleic acid molecules can greatly exceed (e.g., exponentially exceed) the number of initial amplifying restriction endonucleases present in the reaction and therefore can greatly exceed (e.g., exponentially exceed) the number of target nucleic acid molecules that were present in the sample contacted with the probe nucleic acid. Such a greatly expanded relationship (e.g., an exponential relationship) can allow very small amounts of target nucleic acid present in the sample to be readily detected.

After the released portions containing the initial amplifying restriction endonuclease, if present, are contacted with the reporter nucleic acid, the presence or absence of cleaved reporter nucleic acid can be determined. The presence of cleaved reporter nucleic acid can indicate that the sample contained the target nucleic acid, thereby indicating that the sample contained the target genetic or epigenetic element for which the sample is being tested, while the absence of cleaved reporter nucleic acid can indicate that the sample lacked the target nucleic acid, thereby indicating that the sample lacked the target genetic or epigenetic element for which the sample is being tested.

In some cases, the amount of cleaved reporter nucleic acid can be determined. In such cases, the amount of cleaved reporter nucleic acid can indicate the amount of target nucleic acid present in the sample, which can indicated the relative amount of the genetic or epigenetic element present in the organism being tested. A standard curve using known amounts of target nucleic acid can be used to aid in the determination of the amount of target nucleic acid present within a sample. For example, genomic DNA from known heterozygous and/or homozygous (e.g., homozygous for a particular genetic element being tested for) organisms can be included in an assay to determine whether a genomic DNA sample from an organism being tested contains zero, one, or two copies of a particular target nucleic acid for which the organism is being tested based on the amount of cleaved reporter nucleic acid.

In some cases, the reporter nucleic acid can contain a label to aid in the detection of cleaved reporter nucleic acid. For example, reporter nucleic acid can contain a fluorescent label and a quencher such that cleaved reporter nucleic acid provides a fluorescent signal and uncleaved reporter nucleic acid does not provide a fluorescent signal. In some cases, the reporter nucleic acid can contain a label (e.g., a colorimetric label, fluorescent label or an enzyme such as horse radish peroxidase) and can be attached to a solid support (e.g., a well of a microtiter plate). For example, the reporter nucleic acid can be attached to a solid support such that cleavage at the initial amplifying restriction endonuclease cut site by the initial amplifying restriction endonuclease releases a portion of the reporter nucleic acid that contains the label. The resulting reaction mixture can be collected and assessed for the presence, absence, or amount of released portions of the reporter nucleic acid using the label. For example, the released portions of the reporter nucleic acid, if present, can be transferred from one well of a microtiter plate (e.g., a 96-well plate) that contained the reporter nucleic acid to another well of a microtiter plate, where the transferred material can be assessed for a signal from the label.

In some cases, the presence or absence of cleaved first signal expansion nucleic acid, cleaved second signal expansion nucleic acid, or both can be determined. The presence of such cleaved nucleic acid can indicate that the sample contained the target nucleic acid, thereby indicating that the sample contained the target genetic or epigenetic element for which the sample is being tested, while the absence of such cleaved nucleic acid can indicate that the sample lacked the target nucleic acid, thereby indicating that the sample lacked the target genetic or epigenetic element for which the sample is being tested. In some cases, the amount of cleaved first signal expansion nucleic acid, cleaved second signal expansion nucleic acid, or both can be determined. In such cases, the amount of cleaved nucleic acid can indicate the amount of target nucleic acid present in the sample, which can indicated the relative amount of the genetic or epigenetic element present in the organism being tested. In these cases, the use of cleaved first signal expansion nucleic acid, cleaved second signal expansion nucleic acid, or both to assess the sample for target nucleic acid can be in addition to the use of a separate reporter nucleic acid step or can replace the use of a separate reporter nucleic acid step. In some cases, the first signal expansion nucleic acid, the second signal expansion nucleic acid, or both can be labeled in a manner similar to that described herein for the reporter nucleic acid to aid in detection. When the presence, absence, or amount of cleaved first signal expansion nucleic acid, cleaved second signal expansion nucleic acid, or both are determined to assess the sample for target nucleic acid, the first signal expansion nucleic acid can be referred to as a first reporter nucleic acid and the second signal expansion nucleic acid can be referred to as a second reporter nucleic acid even though they include amplifying restriction endonucleases. A standard curve using known amounts of target nucleic acid can be used to aid in the determination of the amount of target nucleic acid present within a sample. For example, genomic DNA from known heterozygous and/or homozygous (e.g., homozygous for a particular genetic element being tested for) organisms can be included in an assay to determine whether a genomic DNA sample from an organism being tested contains zero, one, or two copies of a particular target nucleic acid for which the organism is being tested based on the amount of cleaved first signal expansion nucleic acid, cleaved second signal expansion nucleic acid, or both.

Figure 3:
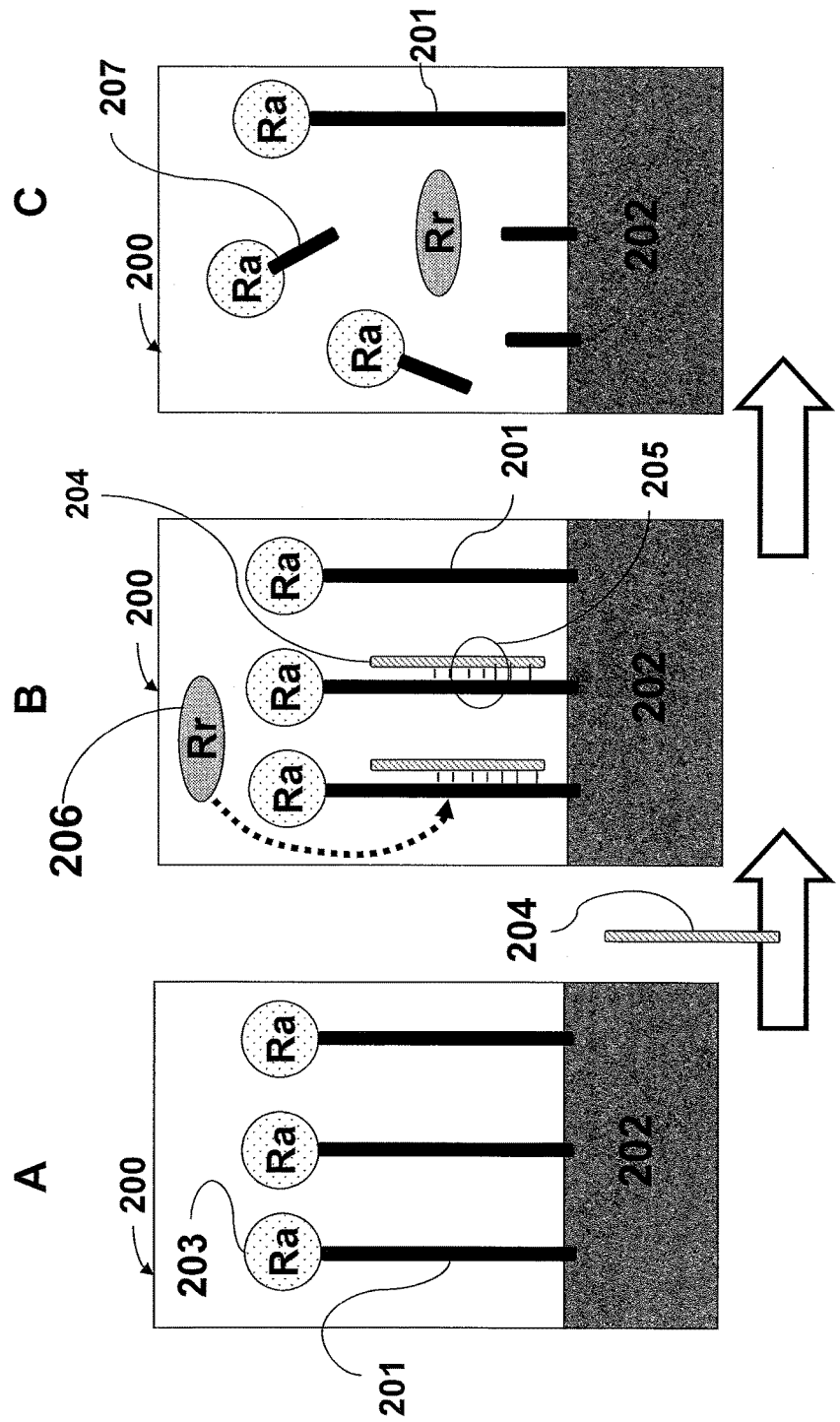
FIG. 3 is a schematic depicting an exemplary method for detecting target nucleic acid using probe nucleic acid, a recognition restriction endonuclease, first signal expansion nucleic acid, second signal expansion nucleic acid, and reporter nucleic acid.
Figure 5:
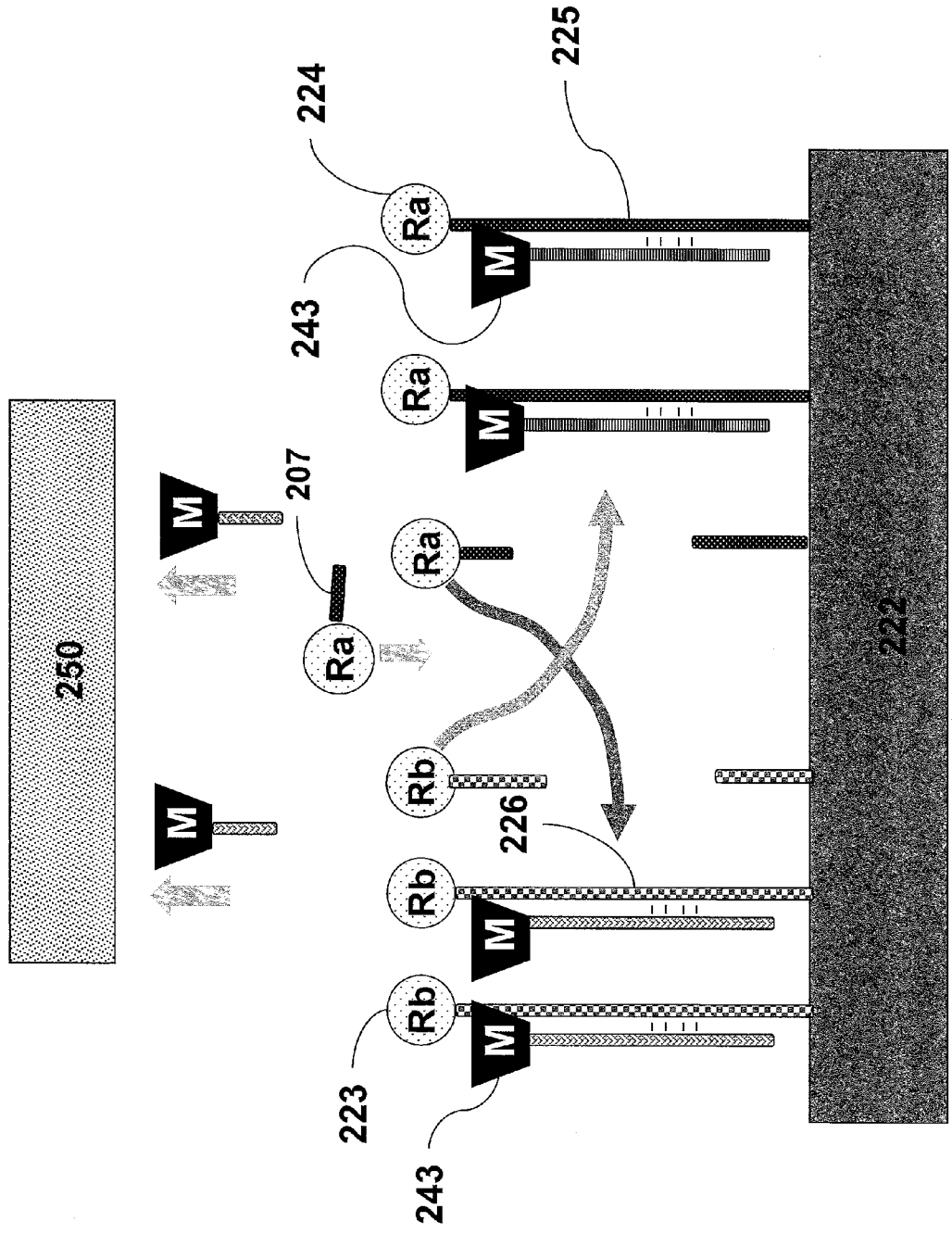
FIG. 5 is a schematic of an exemplary configuration of first signal expansion nucleic acid and second signal expansion nucleic acid that can be used with the methods and materials provided herein for detecting target nucleic acid. Such first signal expansion nucleic acid and second signal expansion nucleic acid can be used with or without reporter nucleic acid. When used without a separate reporter nucleic acid step, such signal expansion nucleic acid can be referred to as reporter nucleic acid.

Examples of a method of detecting target nucleic acid that includes using probe nucleic acid, first signal expansion nucleic acid, second signal expansion nucleic acid, and reporter nucleic acid are set forth in FIGS. 3-5. With reference to FIG. 3, first reaction chamber 200 (e.g., a microtiter plate well) can contain probe nucleic acid 201. Probe nucleic acid 201 can be attached (e.g., immobilized) to solid support 202 and can include initial amplifying restriction endonuclease 203 (Ra). Probe nucleic acid 201 can be attached to solid support 202 such that initial amplifying restriction endonuclease 203 is released from solid support 202 upon cleavage of a nucleic acid component of probe nucleic acid 201. Probe nucleic acid 201 can have a single-stranded section having a nucleotide sequence that is complementary to at least a portion of target nucleic acid 204. Probe nucleic acid 201 can be contacted with a sample that may or may not contain target nucleic acid 204. If target nucleic acid 204 is present, at least a portion of target nucleic acid 204 and probe nucleic acid 201 can hybridize to form a double-stranded section of nucleic acid. Such a double-stranded section can contain at least one recognition restriction endonuclease cut site 205. Addition of recognition restriction endonuclease 206 (Rr) to first reaction chamber 200 can result in the cleavage of probe nucleic acid 201 at recognition restriction endonuclease cut site 205 formed by one strand of probe nucleic acid and one strand of target nucleic acid, thereby releasing portion 207 of probe nucleic acid 201 from solid support 202. Portion 207 can include initial amplifying restriction endonuclease 203.

The reaction product from first reaction chamber 200 containing released portion 207, if target nucleic acid 204 was present, can be transferred (e.g., manually or automatically) to second reaction chamber 220. Second reaction chamber 220 can contain first signal expansion nucleic acid 226 and second signal expansion nucleic acid 225. First signal expansion nucleic acid 226 can have at least one double-stranded portion that contains at least one initial amplifying restriction endonuclease cut site 230. First signal expansion nucleic acid 226 can be attached (e.g., immobilized) to solid support 222 and can include secondary amplifying restriction endonuclease 223 (Rb). First signal expansion nucleic acid 226 can be attached to solid support 222 such that portion 234 containing secondary amplifying restriction endonuclease 223 is released from solid support 222 upon cleavage of first signal expansion nucleic acid 226 at initial amplifying restriction endonuclease cut site 230. For clarity, frame E of FIG. 3 omits depicting one strand from the cleaved versions of first signal expansion nucleic acid 226 and second signal expansion nucleic acid 225.

Second signal expansion nucleic acid 225 can have at least one double-stranded portion that contains at least one secondary amplifying restriction endonuclease cut site 232. Second signal expansion nucleic acid 225 can be attached (e.g., immobilized) to solid support 222 and can include initial amplifying restriction endonuclease 224. Second signal expansion nucleic acid 225 can be attached to solid support 222 such that portion 236 containing initial amplifying restriction endonuclease 224 is released from solid support 222 upon cleavage of second signal expansion nucleic acid 225 at secondary amplifying restriction endonuclease cut site 232. Initial amplifying restriction endonuclease 203 of probe nucleic acid 201 and initial amplifying restriction endonuclease 224 of second signal expansion nucleic acid 225 can be the same restriction endonuclease. For example, both can be an EcoRI restriction endonuclease.

Addition of the reaction product from first reaction chamber 200 to second reaction chamber 220 can result in the cleavage of first signal expansion nucleic acid 226 at initial amplifying restriction endonuclease cut site 230 if the reaction product contains portion 207. Such cleavage of first signal expansion nucleic acid 226 can result in the release of portion 234 from solid support 222. Portion 234, which can include secondary amplifying restriction endonuclease 223, can result in the cleavage of second signal expansion nucleic acid 225 at secondary amplifying restriction endonuclease cut site 232. Such cleavage of second signal expansion nucleic acid 225 can result in the release of portion 236 from solid support 222. Thus, this reaction can result in the accumulation of released portions 234 and 236.

The reaction product from second reaction chamber 220 containing released portion 207, released portion 234, and released portion 236, if target nucleic acid 204 was present, can be transferred (e.g., manually or automatically) to third reaction chamber 240. Third reaction chamber 240 can contain reporter nucleic acid 241. Reporter nucleic acid 241 can be attached (e.g., immobilized) to solid support 242 and can include marker (e.g., a label) 243 (M). Reporter nucleic acid 241 can be attached to solid support 242 such that marker 243 is released from solid support 242 upon cleavage of a nucleic acid component of reporter nucleic acid 241. Reporter nucleic acid 241 can have at least one double-stranded portion that contains at least one initial amplifying restriction endonuclease cut site 246. Addition of the reaction product from second reaction chamber 220 to third reaction chamber 240 can result in the cleavage of reporter nucleic acid 241 at initial amplifying restriction endonuclease cut site 246 if the reaction product contains portion 207 and portion 236. In some cases, reporter nucleic acid 241 can include at least one double-stranded portion that contains at least one cut site for secondary amplifying restriction endonuclease 223. In such cases, addition of the reaction product from second reaction chamber 220 to third reaction chamber 240 can result in the cleavage of reporter nucleic acid 241 at the cut site for secondary amplifying restriction endonuclease 223 if the reaction product contains portion 234. Cleavage of reporter nucleic acid 241 can result in the release of portion 247 from solid support 242. Portion 247 can include marker 243.

The reaction product from third reaction chamber 240 can be assessed to determine the presence, absence, or amount of portion 247. The presence of portion 247 can indicate that the sample contained target nucleic acid 204, while the absence of portion 247 can indicate that the sample lacked target nucleic acid 204. In some cases, the amount of portion 247 can be determined. In such cases, the amount of portion 247 can indicate the amount of target nucleic acid 204 present in the sample. The presence, absence, or amount of portion 247 can be determined using marker 243, and portion 247 having marker 243 can be distinguished from uncleaved reporter nucleic acid 241 having marker 243 since, in this example, portion 247 is released from solid support 242, while uncleaved reporter nucleic acid 241 remains attached to solid support 242. For example, in some cases, the reaction product from third reaction chamber 24 can be transferred to fourth reaction chamber where the presence or absence of portion 247 via marker 243 is assessed. If portion 347 is present, the amount of portion 247 present can be quantified.

In some cases and with reference to FIGS. 4 and 5, first signal expansion nucleic acid 226 can include marker (e.g., a label) 243 (M) and second signal expansion nucleic acid 225 can include marker (e.g., a label) 243 (M). In such cases, cleavage of first signal expansion nucleic acid 226 and cleavage of second signal expansion nucleic acid 225 can be assessed using marker 243 to determine the presence, absence, or amount of target nucleic acid within a sample. For example, detector 250 can be used to detect marker 243 released from solid support 222.

Probe nucleic acid 201, first signal expansion nucleic acid 226, second signal expansion nucleic acid 225, and reporter nucleic acid 241 can have various configurations. For example, with reference to FIG. 3, probe nucleic acid 201 can be designed to have a single nucleic acid strand such that the entire nucleic acid component of probe nucleic acid 201 is single-stranded prior to contact with target nucleic acid 204. In another example, probe nucleic acid 201 can be designed in a manner like probe nucleic acid 101 to have two or more strands. See, e.g., FIG. 2. For example, probe nucleic acid 201 can have a first strand and a second strand. The first strand can be attached to a solid support and can be designed to have a single-stranded section having a nucleotide sequence that is complementary to at least a portion of target nucleic acid. The second strand can include an initial amplifying restriction endonuclease and can have a single-stranded section having a nucleotide sequence that can hybridize to the first strand. In some cases, the first strand and second strand can be synthesized or obtained separately and then mixed together to form probe nucleic acid 201. For example, the first strand can be synthesized, biotinylated, and attached to a streptavidin-coated solid support. After synthesizing the nucleic acid component of the second strand and attaching an initial amplifying restriction endonuclease to the synthesized nucleic acid component, the second strand can be incubated with the first strand to form nucleic acid probe 201. In some cases, probe nucleic acid 201 can contain more than two strands. For example, probe nucleic acid can include a first strand, a second strand, and a third strand. In this case, the first strand can be attached to a solid support, the second strand can be hybridized to the first strand and can include a single-stranded section having a nucleotide sequence that is complementary to at least a portion of target nucleic acid, and the third strand can be hybridized to the second strand and can be attached to an initial amplifying restriction endonuclease. Similar one, two, three, or more strand configurations can be used to make first signal expansion nucleic acid, second signal expansion nucleic acid, or reporter nucleic acid. For example, first signal expansion nucleic acid and second signal expansion nucleic acid can be designed to have a configuration as shown in FIG. 4 or 5.

Probe nucleic acid described herein typically includes at least one single-stranded DNA section that is designed to hybridize with a desired target nucleic acid and thereby create a recognition restriction endonuclease cut site. The other portions of the probe nucleic acid can include DNA, RNA, or other molecules. For example, probe nucleic acid can include biotin such that the probe nucleic acid can be attached to a streptavidin-coated solid support. In some cases, the single-stranded section of the probe nucleic acid that is designed to hybridize with a desired target nucleic acid and create a recognition restriction endonuclease cut site can be RNA or a nucleic acid analog (e.g., a peptide nucleic acid (PNA)) provided that such a single-stranded section can (i) hybridize with the desired target nucleic acid and (ii) create a recognition restriction endonuclease cut site with the complementary target nucleic acid sequence that is capable of being cleaved by the recognition restriction endonuclease. Examples of restriction endonucleases that can be used as recognition restriction endonucleases to cleave a recognition restriction endonuclease cut site that is created between an RNA section of the probe nucleic acid and a DNA section of the target nucleic acid include, without limitation, HhaI, AluI, TaqI, HaeIII, EcoRI, HindII, SalI, and MspI restriction endonucleases.

Probe nucleic acid described herein can be any length provided that the single-stranded section of the probe nucleic acid that is designed to hybridize with a desired target nucleic acid is capable of hybridizing to the target nucleic acid and provided that the amplifying restriction endonuclease of the probe nucleic acid is capable of cleaving its amplifying restriction endonuclease cut site after the probe nucleic acid is cleaved by a recognition restriction endonuclease. In general, the single-stranded section of the probe nucleic acid that is designed to hybridize with a desired target nucleic acid can be between about 10 and about 500 or more nucleotides (e.g., between about 10 and about 400 nucleotides, between about 10 and about 300 nucleotides, between about 10 and about 200 nucleotides, between about 10 and about 100 nucleotides, between about 10 and about 50 nucleotides, between about 10 and about 25 nucleotides, between about 20 and about 500 nucleotides, between about 30 and about 500 nucleotides, between about 40 and about 500 nucleotides, between about 50 and about 500 nucleotides, between about 15 and about 50 nucleotides, between about 15 and about 25 nucleotides, between about 20 and about 50 nucleotides, between about 18 and about 25 nucleotides, between about 20 and about 60 nucleotides, between about 25 and about 55 nucleotides, between about 30 and about 50 nucleotides, between about 35 and about 45 nucleotides, or between about 38 and about 42 nucleotides) in length. The recognition restriction endonuclease cut site that will be created by the hybridization of target nucleic acid to this single-stranded section of the probe nucleic acid can be located at any position alone the single-stranded section. For example, the recognition restriction endonuclease cut site to be created can be towards the 5' end, towards the 3' end, or near the center of the single-stranded section of the probe nucleic acid. In general, the overall length of the probe nucleic acid described herein can be between about 10 and about 2500 or more nucleotides (e.g., between about 10 and about 2000 nucleotides, between about 10 and about 1000 nucleotides, between about 10 and about 500 nucleotides, between about 10 and about 400 nucleotides, between about 10 and about 300 nucleotides, between about 10 and about 200 nucleotides, between about 10 and about 100 nucleotides, between about 10 and about 50 nucleotides, between about 10 and about 25 nucleotides, between about 20 and about 500 nucleotides, between about 30 and about 500 nucleotides, between about 40 and about 500 nucleotides, between about 50 and about 500 nucleotides, between about 75 and about 500 nucleotides, between about 100 and about 500 nucleotides, between about 150 and about 500 nucleotides, between about 15 and about 50 nucleotides, between about 15 and about 25 nucleotides, between about 20 and about 50 nucleotides, between about 18 and about 25 nucleotides, between about 20 and about 60 nucleotides, between about 25 and about 55 nucleotides, between about 30 and about 50 nucleotides, between about 35 and about 45 nucleotides, or between about 38 and about 42 nucleotides) in length.

The recognition restriction endonuclease cut site to be created by hybridization of target nucleic acid to the probe nucleic acid can be a cut site of any type of restriction endonuclease. In addition, any type of restriction endonuclease can be used as a recognition restriction endonuclease to cleave probe nucleic acid upon target nucleic acid hybridization. Examples of restriction endonucleases that can be used as recognition restriction endonucleases include, without limitation, EcoRI, EcoRII, BamHI, HindIII, TaqI, NotI, HinfI, Sau3A, PovII, SmaI, HaeIII, HgaI, AluI, EcoRV, EcoP15I, KpnI, PstI, SacI, SalI, ScaI, SphI, StuI, XbaI, AarI, BanII, BseGI, BspPI, CfrI, EcoNI, Hsp92II, NlaIV, RsaI, TaiI, AasI, BbsI, BseJI, BspTI, ClaI, EcoO109I, I-PpoI, NmuCI, RsrII, TaqaI, AatII, BbuI, BseLI, BsrBI, CpoI, KasI, Acc65I, BbvCI, BseMI, BsrDI, Csp45I, Kpn2I, NruI, SacII, TasI, AccB7I, BbvI, BseMII, BsrFI, Csp6I, EheI, KpnI, NsbI, SalI, TatI, AccI, BceAI, BseNI, BsrGI, CspI, Esp3I, KspAI, NsiI, SapI, and TauI restriction endonucleases. In some cases, nucleic acid encoding a naturally-occurring restriction endonuclease can be genetically engineered to create a modified restriction endonuclease that has the ability to recognize a particular cut site. Common computer algorithms can be used to locate restriction endonuclease cut sites along the nucleotide sequence of any desired target nucleic acid. Once located, the sequence of the restriction endonuclease cut site along with additional flanking sequence (e.g., 5' flanking sequence, 3' flanking sequence, or both 5' and 3' flanking sequence) can be used to design the complementary sequence of the probe nucleic acid that is used to hybridize to the target nucleic acid and create the recognition restriction endonuclease cut site upon target nucleic acid hybridization. In some cases, a probe nucleic acid can be designed to have the restriction endonuclease cut site located in the middle or near the middle such that the restriction endonuclease cut site has both 5' and 3' flanking sequences that are complementary to the target nucleic acid.

Figure 10:
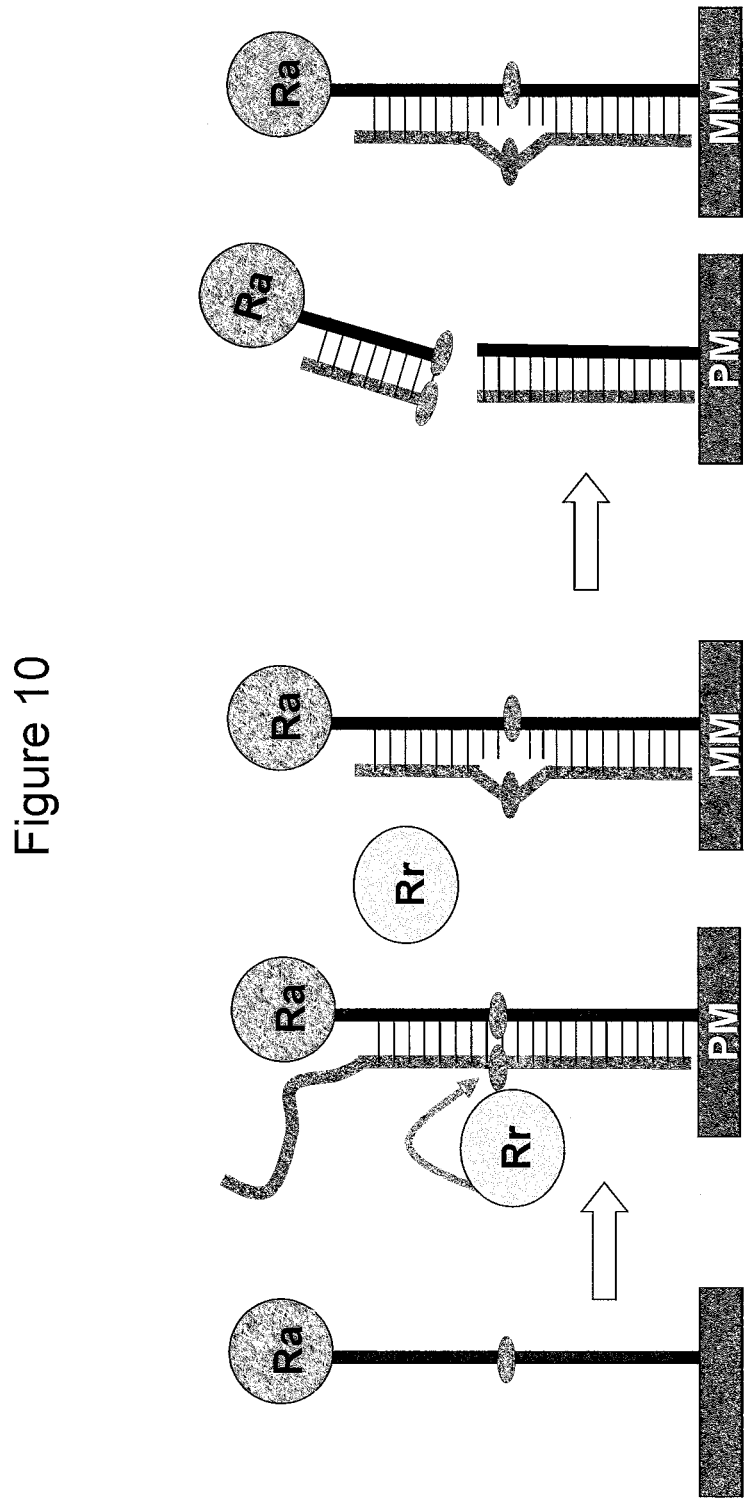
FIG. 10 is a diagram demonstrating how target nucleic acid that perfectly matches (perfect match, PM) the probe nucleic acid at the generated cut site is cleaved by the recognition restriction endonuclease, while nucleic acid lacking the perfect match (mismatch, MM) with the probe nucleic acid at the generated cut site is not cleaved by the recognition restriction endonuclease.

In some cases, the probe nucleic acid is designed to have a single-stranded section that is designed to hybridize with desired target nucleic acid and to form a recognition restriction endonuclease cut site upon target nucleic acid hybridization such that target nucleic acid containing the particular genetic or epigenetic element being tested for hybridizes to the probe nucleic acid and, together with the probe nucleic acid, is cleaved by the recognition restriction endonuclease, thereby releasing a portion of the probe nucleic acid, while nucleic acid lacking the particular genetic or epigenetic element being tested for does not result in the formation of cleaved probe nucleic acid even though such nucleic acid lacking the genetic or epigenetic element may hybridize with the probe nucleic acid. For example, a probe nucleic acid can be designed to contain a single-stranded portion that is designed to hybridize with a target nucleic acid containing a particular SNP sequence and to form a recognition restriction endonuclease cut site at the location of the particular SNP sequence upon target nucleic acid hybridization. In such cases, the target nucleic acid containing the particular SNP sequence being tested for can hybridize to the probe nucleic acid and, together with the probe nucleic acid, can be cleaved by the recognition restriction endonuclease, thereby releasing a portion of the probe nucleic acid, while nucleic acid lacking the particular SNP sequence being tested for can fail to result in the formation of cleaved probe nucleic acid even though such nucleic acid lacking the particular SNP sequence may hybridize with the probe nucleic acid (see, e.g., FIG. 10). In these cases, the recognition restriction endonuclease can be used to differentiate between target nucleic acid containing the particular genetic or epigenetic element being tested for and other nucleic acids that lack the particular genetic or epigenetic element being tested for even though such other nucleic acids may hybridize with the probe nucleic acid. In some cases, the difference between these other nucleic acids and the target nucleic acid being tested for can be a single nucleotide. For example, ApoI can be used as a recognition restriction endonuclease to differentiate between a target nucleic acid containing a 5'-AAATTC-3' sequence and other nucleic acids that simply have a 5'-AAATTA-3' sequence in place of the 5'-AAATTC-3' sequence.

In some cases, probe nucleic acid can be designed for use with a recognition restriction endonuclease that has separate recognition and cleavage sites such as an FokI restriction endonuclease (FIG. 11). FokI recognizes a specific 5-base site (5'-GGATG-3'), but it cleaves the double stranded nucleic acid at a position nine bases downstream of the recognition site provided that these nine bases form perfectly matched double-stranded sequence (FIG. 11). Other examples of such restriction endonucleases include, without limitation, AlwI, MnlI CspCI, AjuI, AloI, PpiI, PsrI, and AarI. Probe nucleic acid designed for use with a recognition restriction endonuclease that has separate recognition and cleavage sites can be used to detect any SNP of interest, including those that do not change a known restriction site with respect to, for example, corresponding wild-type sequences. In such cases, probe nucleic acid can be designed to contain a double stranded portion between 10 and 100 bp in length (e.g., 10 and 75, 10 and 50, 10 and 40, 10 and 30, 20 and 100, 30 and 100, 15 and 75, 15 and 50, 15 and 40, 20 and 50, or 20 and 40 bp in length) that has the recognition site of a recognition restriction endonuclease that has separate recognition and cleavage sites (e.g., FokI) adjacent to a single stranded portion 10 and 100 nucleotides in length (e.g., 10 and 75, 10 and 50, 10 and 40, 10 and 30, 20 and 100, 30 and 100, 15 and 75, 15 and 50, 15 and 40, 20 and 50, or 20 and 40 nucleotides in length) that is designed to have a sequence complementary to a desired target nucleic acid (e.g., a wild-type target nucleic acid or a target nucleic acid containing a SNP) such that hybridization of the desired target nucleic acid creates the cleavage site of the recognition restriction endonuclease. Probe nucleic acid containing any hybridized nucleic acid can be subjected to blunting and ligation reactions. For example, T4 DNA polymerase (or a blunting kit containing this enzyme) can be used to remove free single-stranded ends of nucleic acid hybridized to probe nucleic acid. T4 DNA polymerase can convert DNA with single-stranded 5' or 3' overhangs to 5' phosphorylated, blunt-ended DNA for efficient blunt-end ligation. A DNA ligase (e.g., *E. coli* DNA ligase) can be used subsequently (or simultaneously with T4 DNA polymerase) to ligate the blunted hybridized nucleic acid to the adjacent strand of probe nucleic acid (see, e.g., FIG. 12).

Figure 12:
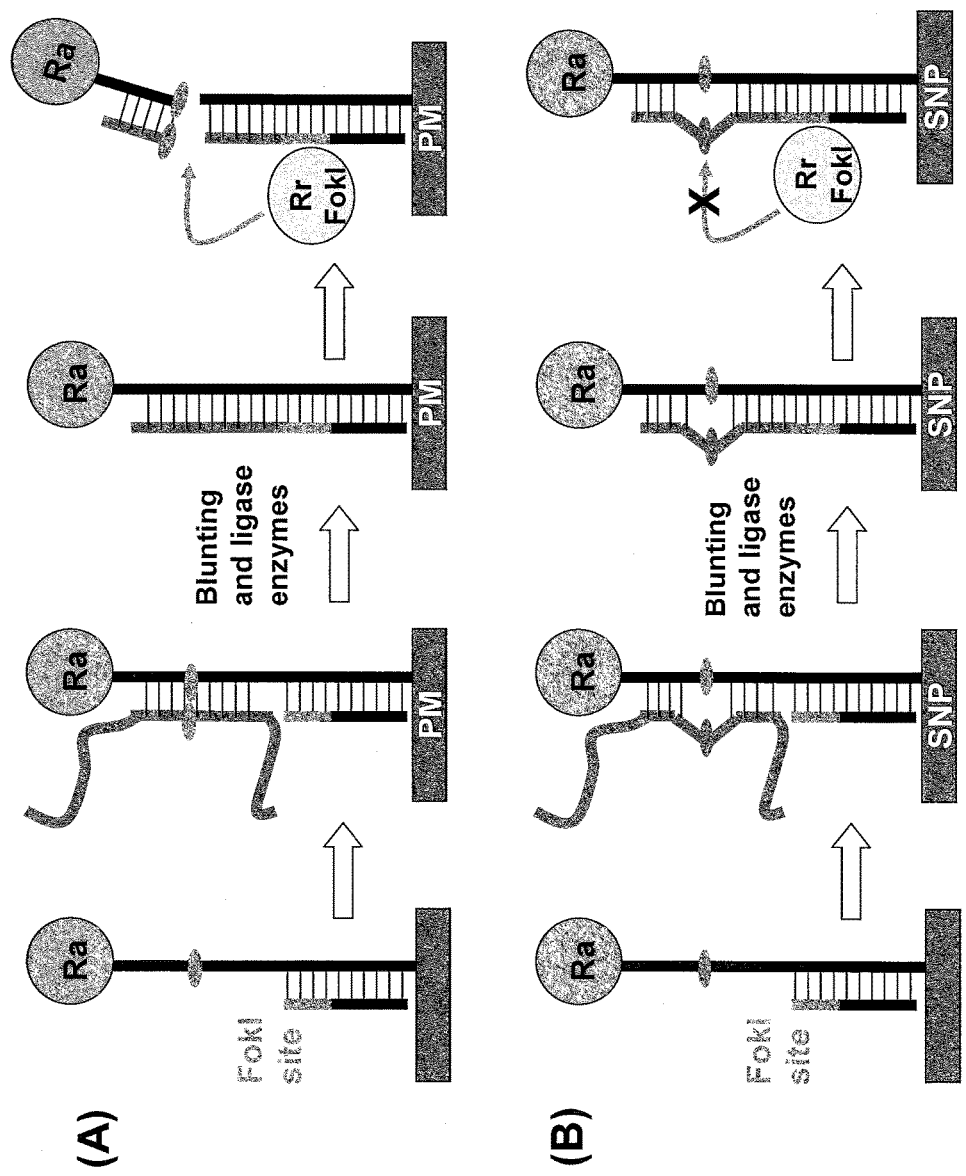
FIG. 12 is a diagram of an example of a method that can be used to differentiate between any target nucleic acid that perfectly matches a portion of probe nucleic acid and any nucleic acid that does not perfectly match that portion of probe nucleic acid. Panel A is a diagram demonstrating how target nucleic acid that perfectly matches (perfect match, PM) the probe nucleic acid generates a cut site, of a recognition restriction endonuclease that has separate recognition and cleavage sites (e.g., an FokI restriction endonuclease), and together with the probe nucleic acid is cleaved by the recognition restriction endonuclease. Panel B is a diagram demonstrating how nucleic acid lacking a perfect match (e.g., nucleic acid containing a SNP) with the probe nucleic acid does not generate a cut site, of a recognition restriction endonuclease that has separate recognition and cleavage sites (e.g., an FokI restriction endonuclease), and together with the probe nucleic acid is not cleaved by the recognition restriction endonuclease.

If the desired target nucleic acid is present in a sample being tested, hybridizes to the single stranded portion of probe nucleic acid to form the cleavage site of the recognition restriction endonuclease that has separate recognition and cleavage sites, and is ligated to the adjacent strand of probe nucleic acid, then the recognition restriction endonuclease can cleave the probe nucleic acid:target nucleic acid hybrid (see, e.g., FIG. 12). Such cleavage can be detected using the methods and materials provided herein. For example, the portion of cleaved probe nucleic acid containing the amplifying restriction endonuclease can be allowed to cleave reporter nucleic acid as described herein.

With reference to FIG. 12, probe nucleic acid can be designed to have a double-stranded DNA section between 10 and 100 bp in length (e.g., 10 and 75, 10 and 50, 10 and 40, 10 and 30, 20 and 100, 30 and 100, 15 and 75, 15 and 50, 15 and 40, 20 and 50, or 20 and 40 bp in length) carrying the FokI recognition site (GGATG) at the free end and a single-stranded DNA section 10 and 100 nucleotides in length (e.g., 10 and 75, 10 and 50, 10 and 40, 10 and 30, 20 and 100, 30 and 100, 15 and 75, 15 and 50, 15 and 40, 20 and 50, or 20 and 40 nucleotides in length) that is complementary to a target nucleic acid DNA fragment (in this example, a wild-type nucleic acid sequence of interest). The single-stranded sequence of the probe nucleic acid is designed such that a potential SNP location is positioned at the potential FokI cleavage site, which is exactly nine nucleotides away from the FokI recognition site. The probe nucleic acid is allowed to hybridize to nucleic acid present in the sample being tested, and any free single-stranded ends of hybridized nucleic acid from the sample being tested are removed using T4 DNA polymerase (or a blunting kit containing this enzyme). A DNA ligase (e.g., *E. coli* DNA ligase) is used to ligate any blunted hybridized nucleic acid from the sample being tested to the adjacent available end of a strand of the probe nucleic acid. If the desired target nucleic acid is present in the sample, a target nucleic acid:probe nucleic acid hybrid is formed such that the hybrid contains both double-stranded FokI recognition and cleavage sites. At this point, FokI can cleave the target nucleic acid:probe nucleic acid hybrid, which can be detected as described herein. If any blunted hybridized nucleic acid from the sample being tested contains a SNP such that a mismatch exists with the probe nucleic acid at the cleavage site, then such probe nucleic acid are not cleaved.

In some cases, an assay or kit provided herein can have one probe nucleic acid designed to detect target nucleic acid having an un-mutated sequence (e.g., a wild-type sequence) and another probe nucleic acid designed to detect target nucleic acid having a mutated version of the sequence (e.g., a sequence containing a SNP). Comparison of signals for mutated versus un-mutated target nucleic acids can provide information about the homozygosity and heterozygosity of the corresponding genotype in terms of the allele of interest.

In general, probe nucleic acid can be designed to have a single-stranded section that is designed to hybridize with desired target nucleic acid and to form a single recognition restriction endonuclease cut site upon target nucleic acid hybridization. In some cases, probe nucleic acid can be designed to have a single-stranded section that is designed to hybridize with desired target nucleic acid and to form more than one (e.g., two, three, four, five, six, seven, eight, nine, ten, or more) recognition restriction endonuclease cut site upon target nucleic acid hybridization. When more than one recognition restriction endonuclease cut site is used, the multiple recognition restriction endonuclease cut sites can be cut sites for the same restriction endonuclease or cut sites for different restriction endonucleases. For example, probe nucleic acid can be designed to have a single-stranded section that is designed to hybridize with desired target nucleic acid and to form one recognition restriction endonuclease cut site for an EcoRI recognition restriction endonuclease and one recognition restriction endonuclease cut site for an XbaI recognition restriction endonuclease upon target nucleic acid hybridization. In such cases, each recognition restriction endonuclease can be used individually or in combination (e.g., as a mixture) to cleave probe nucleic acid that hybridized to target nucleic acid and formed the corresponding recognition restriction endonuclease cut site via such hybridization.

Figure 8:
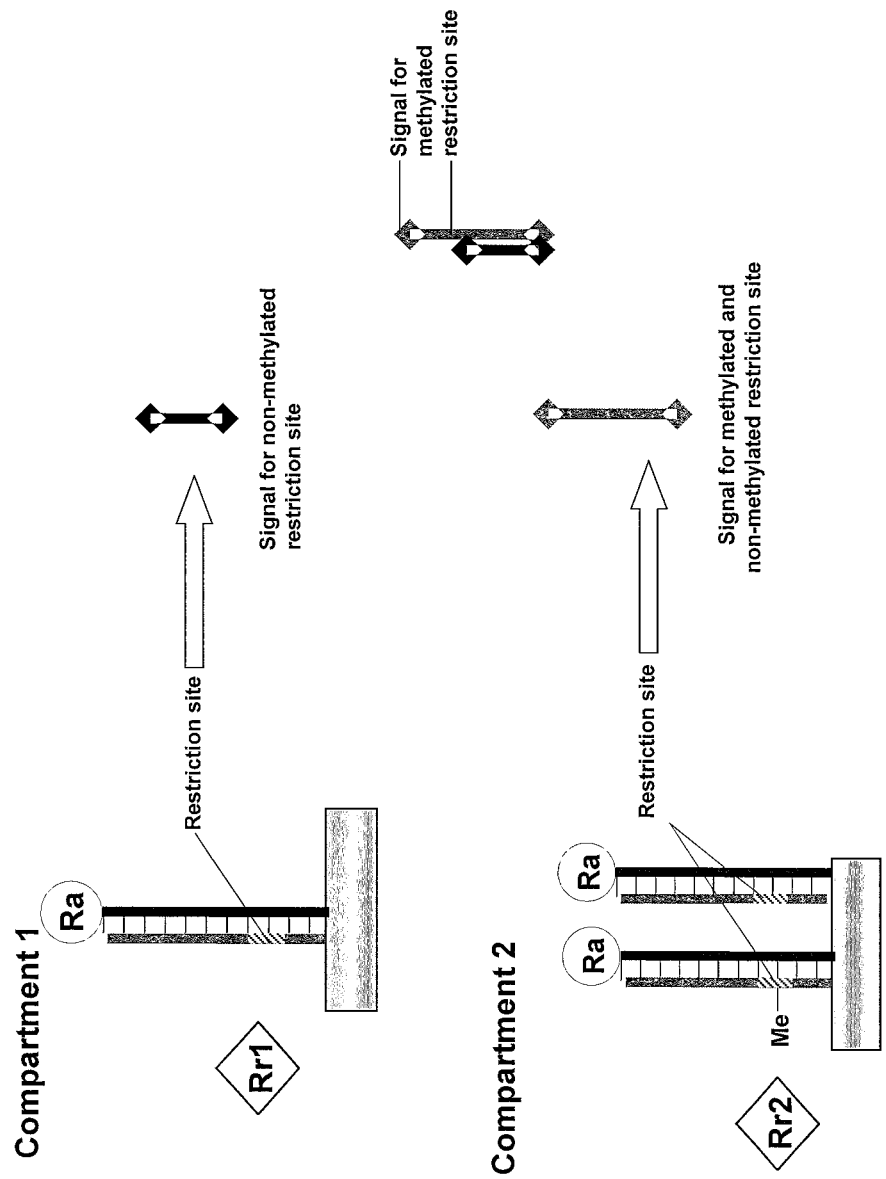
FIG. 8 is a diagram of an example of a method that can be used to detect methylated target DNA. In this example, target DNA is hybridized with the same probe in two different compartments (e.g., wells). Then, a recognition restriction endonuclease (Rr1), which is methylation-sensitive, is added to the compartment 1. Rr1 can only cleave its corresponding restriction site if it is unmodified by methylation (unmethylated C). Another recognition restriction endonuclease (Rr2), which is methylation-insensitive, is added to the compartment 2. Rr2 can cleave both methylated and unmethylated versions of the target DNA. Signal detection for both compartments is then completed as described herein. The resultant signal from compartment 1 corresponds exclusively to unmethylated target, while the resultant signal from compartment 2 corresponds to all target DNA notwithstanding its methylation state. Thus, the amount of methylated target can be calculated by subtracting the compartment 1 signal from the compartment 2 signal. This example uses a pair of methylation sensitive and methylation insensitive restriction endonucleases that recognize and cut the same site/sequence.

Probe nucleic acid can be designed such that any target nucleic acid containing a genetic or epigenetic element can be detected. Examples of target nucleic acid that can be detected using the methods and materials provided herein include, without limitation, genomic DNA, RNA, cDNA, methylated DNA, and combinations thereof. In some cases such as those involving assessing a biological sample for a genetic or epigenetic element in RNA, the target nucleic acid can be an RNA or a cDNA generated from an RNA. When detecting an RNA target nucleic acid, restriction endonucleases having the ability to cleave a recognition restriction endonuclease cut site that is created between a DNA section of the probe nucleic acid and the RNA target nucleic acid can be used as recognition restriction endonucleases. Examples of such restriction endonucleases include, without limitation, HhaI, AluI, TaqI, HaeIII, EcoRI, HindII, SalI, and MspI restriction endonucleases. When detecting methylated target nucleic acid (e.g., a methylated DNA), restriction endonucleases having the ability to cleave a recognition restriction endonuclease cut site that includes a methylated nucleotide to be assessed can be used as recognition restriction endonucleases. Examples of restriction endonucleases having the ability to recognize methylated nucleotides include, without limitation, DpnI, GlaI, HpaII, MspI, AciI, HhaI, and SssI restriction endonucleases. In such cases, a control can include detecting the same target nucleic acid without the methylated nucleotide. In some cases, a combination of methylation insensitive and methylation sensitive restriction endonucleases can be used to assess a sample for methylated target nucleic acid. For example, similar generation of cleavage products using both methylation insensitive and methylation sensitive restriction endonucleases designed for the same site can indicate that the target nucleic acid lacks methylation at that site, while an increased level of cleavage products using a methylation insensitive restriction endonuclease as compared to the level generated using a methylation sensitive restriction endonuclease designed for the same site can indicate that the target nucleic acid is methylated at that site (see, e.g., FIG. 8).

Any appropriate pair of methylation sensitive and methylation insensitive isoschizomers can be used as described herein. Examples of such recognition restriction endonuclease pairs include, without limitation, the MspI/HpaII pair that cut CCGG sites, with HpaII being sensitive to methylation of the second C (blocked by CCmGG) and the EcoRII/BstN1 pair that cut CCNGG sites, with BstN1 being methylation-sensitive. There are more than 300 methylation sensitive restriction endonucleases known that can be used as described herein, and about 30 of them have methylation insensitive isoschizomers (McClelland et al., *Nucleic Acids Res.*, 22:3640-3659 (1994)).

Figure 9:
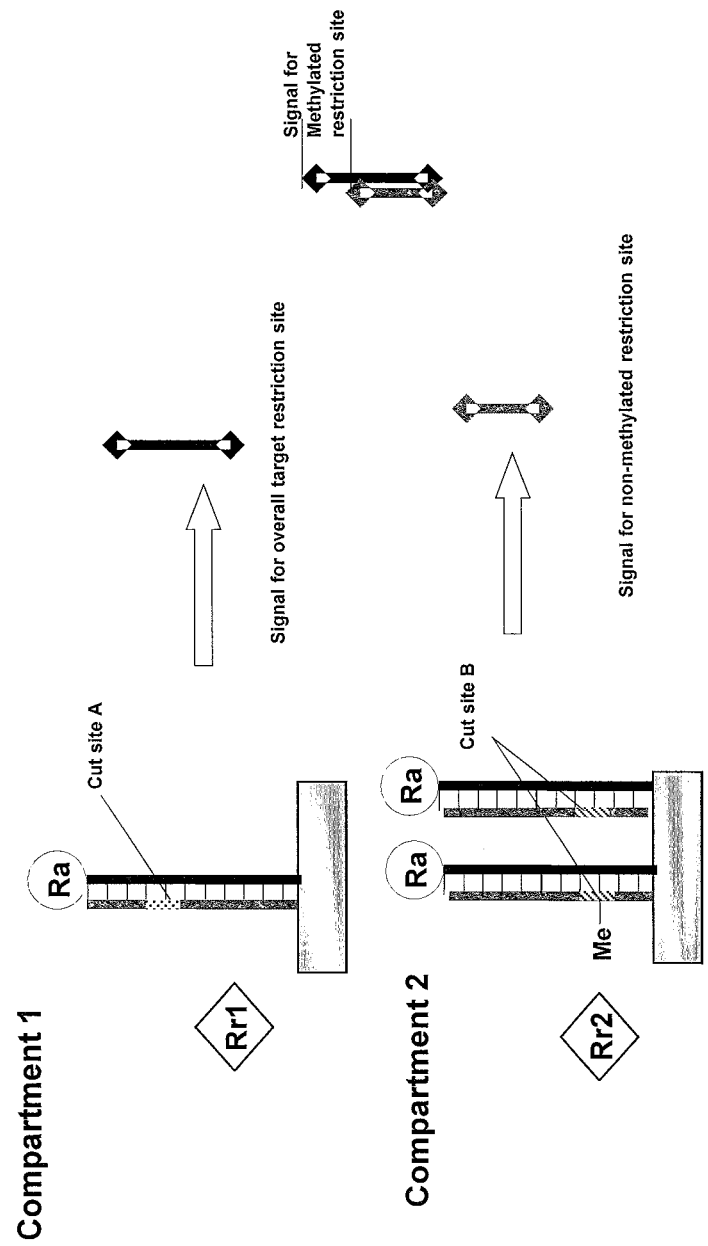
FIG. 9 is a diagram of an example of a method that can be used to detect methylated target DNA using two different methylation sensitive recognition restriction endonucleases (Rr1 and Rr1) that have different cut sites (cut site A and cut site B).

In some cases, the presence, absence, or amount of target methylated DNA can be determined using methylation sensitive recognition restriction endonucleases as opposed to a pair of methylation sensitive and methylation insensitive isoschizomers (see, e.g., FIG. 9). For example, target DNA can be contacted with the same probe nucleic acid in two different compartments or wells (e.g., compartment 1 and compartment 2). A first recognition restriction endonuclease (e.g., Rr1), which cleaves a cut site (e.g., cut site A) that does not contain any C nucleotides and thus can not be methylated, can be added to compartment 1. Upon hybridization with the target DNA, all probe-target hybrids are cleaved by Rr1, and the signal from compartment 1 corresponds to the total amount of the target DNA in the sample. A second recognition restriction endonuclease (e.g., Rr2), which is methylation-sensitive and can only cleave a different site (e.g., site B) if it is unmethylated, can be added to compartment 2. Upon hybridization with the target DNA, probe-target hybrids are cleaved by Rr2 only if site B is unmethylated, and the signal from compartment 2 corresponds only to the unmethylated target DNA within the sample. Signal detection for both compartments can be carried out as described herein. The resultant signal from compartment 1 can correspond to the total amount of target DNA, while the compartment 2 signal can correspond only to the amount of unmethylated target DNA. Thus, the amount of methylated target can be calculated by subtracting the compartment 2 signal from the compartment 1 signal.

The nucleotide sequence of target nucleic acid to be detected can be obtained from, for example, common nucleic acid sequence databases such as GenBank® (e.g., the SNP database of GenBank®). A portion of target nucleic acid sequence can be selected using a computer-based program. For example, a computer-based program can be used to detect restriction endonuclease cut sites within a portion of target nucleic acid (e.g., at the location of a genetic or epigenetic element whether the genetic or epigenetic element is a single nucleotide element or a larger nucleotide sequence element such as a 5, 10, 15, 20, 50, 100, or more nucleotide insertion). Such information can be used to design probe nucleic acid such that the single-stranded section creates at least one recognition restriction endonuclease cut site upon hybridization of the target nucleic acid. In some cases, bioinformatics computer-based programs and tools can be used to assist in the design of probe nucleic acid. For example, computer programs (e.g., BLAST® and alignment programs) and computer databases (e.g., GenBank®) can be used to identify nucleic acid sequences of a particular organism's genome (e.g., sequences from particular genes, coding sequences, promotors, enhancers, or untranslated regions). In addition, computer programs such as CLC Workbench or Vector NTI (Invitrogen) can be used to identify the location of restriction endonuclease cut sites within a particular nucleic acid sequence. In some cases, sequence analysis computer programs can be used to identify sequences with limited or an absence of repeats, a presence of high sequence complexity of a potential recognition restriction endonuclease cut site, and/or limited or an absence of hairpin structures. Identification of such sequences can help reduce the risk of probe self-hybridization and potentially unintended cutting by a recognition endonuclease.

Any appropriate method can be used to obtain the nucleic acid component of the probe nucleic acid. For example, common molecular cloning and chemical nucleic acid synthesis techniques can be used to obtain the nucleic acid component of the probe nucleic acid. In some cases, the nucleic acid component of the probe nucleic acid can be synthesized using commercially available automated oligonucleotide synthesizers such as those available from Applied Biosystems (Foster City, Calif.). In some cases, probe nucleic acids can be synthesized de novo using any of a number of procedures widely available in the art. Examples of such methods of synthesis include, without limitation, the β-cyanoethyl phosphoramidite method (Beaucage et al., *Tet. Let.*, 22:1859-1862 (1981)) and the nucleoside H-phosphonate method (Garegg et al., *Tet. Let.*, 27:4051-4054 (1986); Froehler et al., *Nucl. Acid Res.*, 14:5399-5407 (1986); Garegg et al., *Tet. Let.*, 27:4055-4058 (1986); and Gaffney et al., *Tet. Let.*, 29:2619-2622 (1988)). These methods can be performed by a variety of commercially-available automated oligonucleotide synthesizers. In some cases, recombinant nucleic acid techniques such as PCR and those that include using restriction enzyme digestion and ligation of existing nucleic acid sequences (e.g., genomic DNA or cDNA) can be used to obtain the nucleic acid component of the probe nucleic acid.

Probe nucleic acid described herein can be attached to a solid support. Examples of solid supports include, without limitation, a well of a microtiter plate (e.g., a 96-well microtiter plate or ELISA plate), beads (e.g., magnetic, glass, plastic, or gold-coated beads), slides (e.g., glass or gold-coated slides), micro- or nano-particles (e.g., carbon nanotubes), platinum solid supports, palladium solid supports, and a surface of a chamber or channel within a microfluidic device. In some cases, a solid support can be a silicon oxide-based solid support, a plastic polymer-based solid support (e.g., a nylon, nitrocellulose, or polyvinylidene fluoride-based solid support), or a biopolymer-based (e.g., a cross-linked dextran or cellulose-based solid support) solid support. Probe nucleic acid can be directly or indirectly attached to a solid support. For example, biotin can be a component of the probe nucleic acid, and the probe nucleic acid containing biotin can be indirectly attached to a solid support that is coated with streptavidin via a biotin-streptavidin interaction. In some cases, probe nucleic acid can be attached to a solid support via a covalent or non-covalent interaction. For example, probe nucleic acid can be covalently attached to magnetic beads as described elsewhere (Albretsen et al., *Anal. Biochem.*, 189(1):40-50 (1990)).

Probe nucleic acid can be designed to contain any type of restriction endonuclease as an amplifying restriction endonuclease. In general, an amplifying restriction endonuclease of the probe nucleic acid is typically a different restriction endonuclease than the restriction endonuclease that is used as a recognition restriction endonuclease. For example, when an EcoRI restriction endonuclease is used as a recognition restriction endonuclease, a restriction endonuclease other than an EcoRI restriction endonuclease (e.g., a HindIII restriction endonuclease) is used as an amplifying restriction endonuclease. Examples of restriction endonucleases that can be used as amplifying restriction endonucleases include, without limitation, EcoRI, EcoRII, BamHI, HindIII, TaqI, NotI, HinfI, Sau3A, PovII, SmaI, HaeIII, HgaI, AluI, EcoRV, EcoP15I, KpnI, PstI, SacI, SalI, ScaI, SphI, StuI, XbaI, AarI, BanII, BseGI, BspPI, CfrI, EcoNI, Hsp92II, NlaIV, RsaI, TaiI, AasI, BbsI, BseLI, BspTI, ClaI, EcoO109I, I-PpoI, NmuCI, RsrII, TaqaI, AatII, BbuI, BseLI, BsrBI, CpoI, KasI, Acc65I, BbvCI, BseMI, BsrDI, Csp45I, Kpn2I, NruI, SacII, TasI, AccB7I, BbvI, BseMII, BsrFI, Csp6I, EheI, KpnI, NsbI, SalI, TatI, AccI, BceAI, BseNI, BsrGI, CspI, Esp3I, KspAI, NsiI, SapI, and TauI restriction endonucleases. Any number of molecules of the same amplifying restriction endonuclease can be attached to one probe nucleic acid molecule. For example, a single probe nucleic acid molecule can contain one, two, three, four, five, or more EcoRI amplifying restriction endonuclease molecules. In some cases, a single probe nucleic acid molecule can contain two or more (e.g., two, three, four, five, or more) different types of amplifying restriction endonucleases. For example, a single probe nucleic acid molecule can contain three EcoRI amplifying restriction endonuclease molecules and two BanII amplifying restriction endonuclease molecules.

Any appropriate method can be used to attach an amplifying restriction endonuclease to a nucleic acid component of the probe nucleic acid. In some cases, an amplifying restriction endonuclease can be attached by an ionic or covalent attachment. For example, covalent bonds such as amide bonds, disulfide bonds, and thioether bonds, or bonds formed by crosslinking agents can be used. In some cases, a non-covalent linkage can be used. The attachment can be a direct attachment or an indirect attachment. For example, a linker can be used to attach an amplifying restriction endonuclease to a nucleic acid component of the probe nucleic acid. In some cases, nucleic acid can include a thiol modification, and a restriction endonuclease can be conjugated to the thiol-containing nucleic acid based on succinimidyl 4-[N-maleimidomethyl]cyclohexane-1-carboxylate (SMCC) using techniques similar to those described elsewhere (Dill et al., *Biosensors and Bioelectronics,* 20:736-742 (2004)). In some cases, a biotinylated nucleic acid and a streptavidin-containing restriction endonuclease can be attached to one another via a biotin-streptavidin interaction. A restriction endonuclease can be conjugated with streptavidin using, for example, sulfosuccinimidyl 6-(3'-[2-pyridyldithio]-propionamido)hexanoate. An amplifying restriction endonuclease can be attached at any location of a nucleic acid component of the probe nucleic acid. For example, an amplifying restriction endonuclease can be attached at an end (e.g., a 5' end or 3' end) of a nucleic acid component, in the middle of a nucleic acid component, or at any position along the length of a nucleic acid component.

Signal expansion nucleic acid (e.g., first signal expansion nucleic acid and second signal expansion nucleic acid) and reporter nucleic acid described herein typically include at least one double-stranded DNA section that includes an amplifying restriction endonuclease cut site (e.g., an initial amplifying restriction endonuclease cut site, a secondary amplifying restriction endonuclease cut site, or a tertiary amplifying restriction endonuclease cut site). The other portions of the signal expansion nucleic acid or reporter nucleic acid can include DNA, RNA, or other molecules. For example, reporter nucleic acid can include biotin such that the reporter nucleic acid can be attached to a streptavidin-coated solid support. In some cases, one or both strands of the double-stranded section of the signal expansion nucleic acid or the reporter nucleic acid that contains an amplifying restriction endonuclease cut site can be RNA or a nucleic acid analog (e.g., a peptide nucleic acid (PNA)) provided that such a double-stranded section is capable of being cleaved by the amplifying restriction endonuclease. Examples of restriction endonucleases that can be used as amplifying restriction endonucleases to cleave a DNA:RNA hybrid section of signal expansion nucleic acid or reporter nucleic acid include, without limitation, HhaI, AluI, TaqI, HaeIII, EcoRI, HindII, SalI, and MspI restriction endonucleases.

Signal expansion nucleic acid or reporter nucleic acid described herein can be any length provided that the double-stranded section that contains the amplifying restriction endonuclease cut site is capable of being cleaved by the amplifying restriction endonuclease. In general, the double-stranded section of signal expansion nucleic acid or reporter nucleic acid can be between about 10 and about 500 or more nucleotides (e.g., between about 10 and about 400 nucleotides, between about 10 and about 300 nucleotides, between about 10 and about 200 nucleotides, between about 10 and about 100 nucleotides, between about 10 and about 50 nucleotides, between about 10 and about 25 nucleotides, between about 20 and about 500 nucleotides, between about 30 and about 500 nucleotides, between about 40 and about 500 nucleotides, between about 50 and about 500 nucleotides, between about 15 and about 50 nucleotides, between about 15 and about 25 nucleotides, between about 20 and about 50 nucleotides, or between about 18 and about 25 nucleotides, between about 20 and about 60 nucleotides, between about 25 and about 55 nucleotides, between about 30 and about 50 nucleotides, between about 35 and about 45 nucleotides, or between about 38 and about 42 nucleotides) in length. In some cases, the double-stranded section of signal expansion nucleic acid or reporter nucleic acid can be between 5 and 50 nucleotides in length. The amplifying restriction endonuclease cut site of the signal expansion nucleic acid or the reporter nucleic acid can be located at any position alone the double-stranded section. For example, the amplifying restriction endonuclease cut site can be towards the 5' end, towards the 3' end, or near the center of the double-stranded section of the signal expansion nucleic acid or the reporter nucleic acid. In general, the overall length of signal expansion nucleic acid or reporter nucleic acid described herein can be between about 10 and about 2500 or more nucleotides (e.g., between about 10 and about 2000 nucleotides, between about 10 and about 1000 nucleotides, between about 10 and about 500 nucleotides, between about 10 and about 400 nucleotides, between about 10 and about 300 nucleotides, between about 10 and about 200 nucleotides, between about 10 and about 100 nucleotides, between about 10 and about 50 nucleotides, between about 10 and about 25 nucleotides, between about 20 and about 500 nucleotides, between about 30 and about 500 nucleotides, between about 40 and about 500 nucleotides, between about 50 and about 500 nucleotides, between about 75 and about 500 nucleotides, between about 100 and about 500 nucleotides, between about 150 and about 500 nucleotides, between about 15 and about 50 nucleotides, between about 15 and about 25 nucleotides, between about 20 and about 50 nucleotides, between about 18 and about 25 nucleotides, between about 20 and about 60 nucleotides, between about 25 and about 55 nucleotides, between about 30 and about 50 nucleotides, between about 35 and about 45 nucleotides, or between about 38 and about 42 nucleotides) in length.

The amplifying restriction endonuclease cut site of signal expansion nucleic acid or reporter nucleic acid described herein can be a cut site of any type of restriction endonuclease. In addition, any type of restriction endonuclease can be used as an amplifying restriction endonuclease to cleave signal expansion nucleic acid or reporter nucleic acid. Examples of restriction endonucleases that can be used as amplifying restriction endonucleases include, without limitation, EcoRI, EcoRII, BamHI, HindIII, TaqI, NotI, HinfI, Sau3A, PovII, SmaI, HaeIII, HgaI, AluI, EcoRV, EcoP15I, KpnI, PstI, SacI, SalI, ScaI, SphI, StuI, XbaI, AarI, BanII, BseGI, BspPI, CfrI, EcoNI, Hsp92II, NlaIV, RsaI, TaiI, AasI, BbsI, BseJI, BspTI, ClaI, EcoO109I, I-PpoI, NmuCI, RsrII, TaqaI, AatII, BbuI, BseLI, BsrBI, CpoI, KasI, Acc65I, BbvCI, BseMI, BsrDI, Csp45I, Kpn2I, NruI, SacII, TasI, AccB7I, BbvI, BseMII, BsrFI, Csp6I, EheI, KpnI, NsbI, SalI, TatI, AccI, BceAI, BseNI, BsrGI, CspI, Esp3I, KspAI, NsiI, SapI, and TauI restriction endonucleases.

In general, signal expansion nucleic acid or reporter nucleic acid can be designed to have a double-stranded section that contains a single amplifying restriction endonuclease cut site. In some cases, signal expansion nucleic acid or reporter nucleic acid provided herein can be designed to have a double-stranded section that contains more than one (e.g., two, three, four, five, six, seven, eight, nine, ten, or more) amplifying restriction endonuclease cut site. When more than one amplifying restriction endonuclease cut site is used, the multiple amplifying restriction endonuclease cut sites can be cut sites for the same restriction endonuclease or cut sites for different restriction endonucleases. For example, reporter nucleic acid can be designed to have a double-stranded section that contains one initial amplifying restriction endonuclease cut site for an EcoRI initial amplifying restriction endonuclease and one secondary amplifying restriction endonuclease cut site for an XbaI secondary amplifying restriction endonuclease.

Any appropriate method can be used to obtain the nucleic acid component of signal expansion nucleic acid or reporter nucleic acid. For example, common molecular cloning and chemical nucleic acid synthesis techniques can be used to obtain the nucleic acid component of signal expansion nucleic acid or reporter nucleic acid. In some cases, the nucleic acid component of signal expansion nucleic acid or reporter nucleic acid can be synthesized using commercially available automated oligonucleotide synthesizers such as those available from Applied Biosystems (Foster City, Calif.). In some cases, signal expansion nucleic acid or reporter nucleic acid can be synthesized de novo using any of a number of procedures widely available in the art. Examples of such methods of synthesis include, without limitation, the β-cyanoethyl phosphoramidite method (Beaucage et al., *Tet. Let.,* 22:1859-1862 (1981)) and the nucleoside H-phosphonate method (Garegg et al., *Tet. Let.,* 27:4051-4054 (1986); Froehler et al., *Nucl. Acid Res.,* 14:5399-5407 (1986); Garegg et al., *Tet. Let.,* 27:4055-4058 (1986); and Gaffney et al., *Tet. Let.,* 29:2619-2622 (1988)). These methods can be performed by a variety of commercially-available automated oligonucleotide synthesizers. In some cases, recombinant nucleic acid techniques such as PCR and those that include using restriction enzyme digestion and ligation of existing nucleic acid sequences (e.g., genomic DNA or cDNA) can be used to obtain the nucleic acid component of signal expansion nucleic acid or reporter nucleic acid.

Signal expansion nucleic acid or reporter nucleic acid described herein can be attached to a solid support. Examples of solid supports include, without limitation, a well of a microtiter plate (e.g., a 96-well microtiter plate or ELISA plate), beads (e.g., magnetic, glass, plastic, or gold-coated beads), slides (e.g., glass or gold-coated slides), micro- or nano-particles (e.g., carbon nanotubes), platinum solid supports, palladium solid supports, and a surface of a chamber or channel within a microfluidic device. In some cases, a solid support can be a silicon oxide-based solid support, a plastic polymer-based solid support (e.g., a nylon, nitrocellulose, or polyvinylidene fluoride-based solid support) or a biopolymer-based (e.g., a cross-linked dextran or cellulose-based solid support) solid support.

Signal expansion nucleic acid or reporter nucleic acid can be directly or indirectly attached to a solid support. For example, biotin can be a component of signal expansion nucleic acid or reporter nucleic acid, and the signal expansion nucleic acid or the reporter nucleic acid containing biotin can be indirectly attached to a solid support that is coated with streptavidin via a biotin-streptavidin interaction. In some cases, signal expansion nucleic acid or reporter nucleic acid can be attached to a solid support via a covalent or non-covalent interaction. For example, signal expansion nucleic acid or reporter nucleic acid can be covalently attached to magnetic beads as described elsewhere (Albretsen et al., *Anal. Biochem.,* 189(1):40-50 (1990)).

Signal expansion nucleic acid can be designed to contain any type of restriction endonuclease as an amplifying restriction endonuclease (e.g., an initial amplifying restriction endonuclease, a secondary amplifying restriction endonuclease, or a tertiary amplifying restriction endonuclease). In general, an amplifying restriction endonuclease of signal expansion nucleic acid is typically a different restriction endonuclease than the restriction endonuclease that is used as a recognition restriction endonuclease. For example, when an EcoRI restriction endonuclease is used as a recognition restriction endonuclease, a restriction endonuclease other than an EcoRI restriction endonuclease (e.g., a HeaIII restriction endonuclease) is used as an amplifying restriction endonuclease. Examples of restriction endonucleases that can be used as amplifying restriction endonucleases include, without limitation, EcoRI, EcoRII, BamHI, HindIII, TaqI, NotI, HinfI, Sau3A, PovII, SmaI, HaeIII, HgaI, AluI, EcoRV, EcoP15I, KpnI, PstI, SacI, SalI, ScaI, SphI, StuI, XbaI, AarI, BanII, BseGI, BspPI, CfrI, EcoNI, Hsp92II, NlaIV, RsaI, TaiI, AasI, BbsI, BseLI, BspTI, ClaI, EcoO109I, I-PpoI, NmuCI, RsrII, TaqaI, AatII, BbuI, BseLI, BsrBI, CpoI, KasI, Acc65I, BbvCI, BseMI, BsrDI, Csp45I, Kpn2I, NruI, SacII, TasI, AccB7I, BbvI, BseMII, BsrFI, Csp6I, EheI, KpnI, NsbI, SalI, TatI, AccI, BceAI, BseNI, BsrGI, CspI, Esp3I, KspAI, NsiI, SapI, and TauI restriction endonucleases. Any number of molecules of the same amplifying restriction endonuclease can be attached to one signal expansion nucleic acid molecule. For example, a single signal expansion nucleic acid molecule can contain one, two, three, four, five, or more EcoRI amplifying restriction endonuclease molecules. In some cases, a single signal expansion nucleic acid molecule can contain two or more (e.g., two, three, four, five, or more) different types of amplifying restriction endonucleases. For example, a single signal expansion nucleic acid molecule can contain three BanII amplifying restriction endonuclease molecules and two SacII amplifying restriction endonuclease molecules.

Reporter nucleic acid can be designed to contain a label to aid in the detection of cleaved reporter nucleic acid. In some cases, signal expansion nucleic acid can be designed to contain a label. In such cases, signal expansion nucleic acid containing a label can be used in addition to reporter nucleic acid or in place of reporter nucleic acid to detect target nucleic acid. Examples of labels that can be a component of reporter nucleic acid or signal expansion nucleic acid include, without limitation, fluorescent labels (with or without the use of quenchers), dyes, antibodies, radioactive material, enzymes (e.g., horse radish peroxidase, alkaline phosphatase, laccase, galactosidase, or luciferase), redox labels (e.g., ferrocene redox labels), metallic particles (e.g., gold nanoparticles), and green fluorescent protein-based labels. In some cases, for a redox label, such as ferrocene, the detector can be an electrode for amperometric assay of redox molecules. For example, if the redox label is present in a reduced form of ferrocene, then the electrode at high electrode potential can provide an oxidation of the reduced form of ferrocene, thereby converting it to an oxidized form of ferrocene. The generated current can be proportional to the concentration of ferrocene label in the solution.

In one embodiment, reporter nucleic acid or signal expansion nucleic acid can contain a fluorescent label and a quencher such that cleaved reporter nucleic acid provides a fluorescent signal and uncleaved reporter nucleic acid does not provide a fluorescent signal. In some cases, the reporter nucleic acid or signal expansion nucleic acid can contain a label (e.g., a fluorescent label or an enzyme such as horse radish peroxidase) and can be attached to a solid support (e.g., a well of a microtiter plate). For example, the reporter nucleic acid or signal expansion nucleic acid can be attached to a solid support such that cleavage at the amplifying restriction endonuclease cut site by the amplifying restriction endonuclease releases a portion of the reporter nucleic acid or the signal expansion nucleic acid that contains the label. The resulting reaction mixture can be collected and assessed for the presence, absence, or amount of released portions of the reporter nucleic acid or signal expansion nucleic acid using the label. For example, the released portions of the reporter nucleic acid or the signal expansion nucleic acid, if present, can be transferred from one well of a microtiter plate (e.g., a 96-well plate) that contained the reporter nucleic acid or the signal expansion nucleic acid to another well of a microtiter plate, where the transferred material can be assessed for a signal from the label. Any number of molecules of a label can be attached to one reporter nucleic acid molecule or one signal expansion nucleic acid molecule. For example, a reporter nucleic acid molecule or a single signal expansion nucleic acid molecule can contain one, two, three, four, five, or more fluorescent molecules.

Any appropriate method can be used to attach a label to a nucleic acid component of reporter nucleic acid or signal expansion nucleic acid. In some cases, a label can be attached by an ionic or covalent attachment. For example, covalent bonds such as amide bonds, disulfide bonds, and thioether bonds, or bonds formed by crosslinking agents can be used. In some cases, a non-covalent linkage can be used. The attachment can be a direct attachment or an indirect attachment. For example, a linker can be used to attach a label to a nucleic acid component of reporter nucleic acid or signal expansion nucleic acid. In some cases, nucleic acid can include a thiol modification, and a label can be conjugated to the thiol-containing nucleic acid based on succinimidyl 4-[N-maleimidomethyl]cyclo-hexane-1-carboxylate (SMCC) using techniques similar to those described elsewhere (Dill et al., *Biosensors and Bioelectronics,* 20:736-742 (2004)). In some cases, a biotinylated nucleic acid and a streptavidin-containing label can be attached to one another via a biotin-streptavidin interaction. A label can be conjugated with streptavidin using, for example, sulfosuccinimidyl 6-(3'-[2-pyridyldithio]-propionamido)hexanoate. A label can be attached at any location of a nucleic acid component of reporter nucleic acid or signal expansion nucleic acid. For example, a label can be attached at an end (e.g., a 5' end or 3' end) of a nucleic acid component, in the middle of a nucleic acid component, or at any position along the length of a nucleic acid component of reporter nucleic acid or signal expansion nucleic acid.

As described herein, the methods and materials provided herein can be used to detect target nucleic acid containing a genetic or epigenetic element in any type of sample (e.g., a biological sample). For example, a blood sample or cheek swab sample can be collected from a mammal and assessed for target nucleic acid to determine if the mammal has one or more genetic or epigenetic elements of interest. Once obtained, a sample to be assessed can be processed to obtain nucleic acid. For example, a nucleic acid extraction can be performed on a blood sample to obtain a sample that is enriched for nucleic acid. In some cases, a sample can be heated or treated with a cell lysis agent to release nucleic acid from cells present in the sample.

As described herein, a sample (e.g., a biological sample) can be assessed for the presence, absence, or amount of target nucleic acid (e.g., target nucleic acid containing a genetic or epigenetic element) using an enzymatic amplification cascade of restriction endonucleases described herein without using a nucleic acid amplification technique (e.g., a PCR-based nucleic acid technique). Assessing samples (e.g., biological samples) for the presence, absence, or amount of target nucleic acid using an enzymatic amplification cascade of restriction endonucleases described herein without using a nucleic acid amplification technique can allow patients as well as medical, laboratory, or veterinarian personnel (e.g., clinicians, physicians, physician's assistants, laboratory technicians, research scientists, and veterinarians) to test for one or more genetic or epigenetic elements without the need for potentially expensive thermal cycling devices and potentially time consuming thermal cycling techniques. In some cases, the methods and materials provided herein can be used in combination with a PCR-based nucleic acid technique. For example, a PCR-based nucleic acid technique can be performed to amplify nucleic acid (e.g., a target nucleic acid containing a genetic or epigenetic element) present within a biological sample, and the resulting amplification material can be assessed using an enzymatic amplification cascade of restriction endonucleases described herein to detect the presence, absence, or amount of a particular nucleic acid (e.g., a target nucleic acid a genetic or epigenetic element). In some cases, a limited PCR-based nucleic acid technique can be performed to amplify a target nucleic acid to a point where the amount of amplified target nucleic acid is increased only slightly over the amount of target nucleic acid originally present within the biological sample. For example, a two to twelve cycle PCR technique (e.g., a 2, 3, 4, 5, 6, 7, 8, 9, 10, 11, or 12 cycle PCR technique) can be performed to slightly increase the amount of amplified target nucleic acid as compared to the amount of unamplified target nucleic acid originally present within the biological sample. Such limited PCR-based nucleic acid techniques, when used in combination with an enzymatic amplification cascade of restriction endonucleases described herein, can allow medical, laboratory, or veterinarian personnel to test organisms with a potentially increased level of sensitivity and/or specificity without the potentially lengthy time involved in thermal cycling techniques that include a greater number of cycles. This increased level of sensitivity and/or specificity can be over the high level of sensitivity and specificity of a comparable testing procedure that includes an enzymatic amplification cascade of restriction endonucleases described herein without the limited PCR-based nucleic acid technique. In some cases, the PCR-based nucleic acid technique can be performed to amplify a target nucleic acid to a point where the amount of amplified target nucleic acid is easily detectable (e.g., visually detectable using gel electrophoresis and ethidium bromide staining). For example, a 15 or more cycle PCR technique (e.g., a 20 cycle PCR technique) can be performed to produce at least ng amounts (e.g., greater than 1 ng, 10 ng, 100 ng, 1 µg, 10 µg, or more) of amplified nucleic acid. Such PCR-based nucleic acid techniques, when used in combination with an enzymatic amplification cascade of restriction endonucleases described herein, can allow medical, laboratory, or veterinarian personnel to test organisms with a potentially increased level of sensitivity and/or specificity. This increased level of sensitivity and/or specificity can be over the high level of sensitivity and specificity of a comparable testing procedure that includes an enzymatic amplification cascade of restriction endonucleases described herein without the PCR-based nucleic acid technique.

In some cases, a sample (e.g. a biological sample) can be obtained and subjected to a culturing technique. For example, a cell sample can be obtained and cultured with medium (e.g., enrichment medium) to enrich the sample such that the number of cells present in the sample can increase. Examples of enrichment media include, without limitation, Dulbecco's Modified Eagle Medium (DMEM), Minimum Essential Medium (MEM), Iscove's Modified Dulbecco's Media (IMDM), and AIM V® Medium. In some cases, the culture medium can contain a nutrient (e.g. serum such as fetal calf serum), ingredient, or drug that prevents certain cells from dividing while allowing other cells to divide. In some cases, the culturing technique can include incubating a sample at an appropriate temperature (e.g. between 15° C. and 45° C., between 20° C. and 45° C., between 25° C. and 45° C., between 30° C. and 45° C., between 30° C. and 40° C., between 35° C. and 45° C., or between 35° C. and 40° C.) for an appropriate period of time (e.g., between about 0.5 hours and 48 hours, between about 0.5 hours and 36 hours, between about 0.5 hours and 24 hours, between about 0.5 hours and 12 hours, between about 0.5 hours and 8 hours, between about 0.5 hours and 6 hours, between about 0.5 hours and 5 hours, between about 0.5 hours and 4 hours, between about 0.5 hours and 3 hours, between about 0.5 hours and 2 hours, between about 1 hour and 4 hours, or between about 2 hours and 4 hours). For example, a sample can be obtained and cultured in tissue culture medium at 37° C. for 24-48 hours. Examples of tissue culture techniques that can be used as described herein include, without limitation, those described elsewhere (Animal Cell Culture: A Practical Approach, 3rd edition, J. Masters, ed., Oxford University Press, 2000, 336 pp).

In some cases, a sample, obtained and subjected to a culturing technique or not, can be processed, for example, to remove non-nucleic acid material, to disrupt cell membranes to release nucleic acid, and/or to collect or extract nucleic acid, such that nucleic acid of the sample, if present within the sample, is available for hybridization to probe nucleic acid. For example, a blood or cheek swab sample can be treated with a lysis buffer and subjected to nucleic acid extraction such that a major component of the sample is nucleic acid. In some cases, a sample can be homogenized and treated to disrupt cells that are present in the sample. For example, a blood sample can be subjected to high speed mechanical homogenization with glass/silica/zirconium/stainless steel beads, can be subjected to high temperature (e.g., boiling or autoclaving), can be subjected to chemical lysis with detergents and/or surfactants (e.g., sodium dodecyl sulfate, cetyltrimethylammonium bromide, or sodium lauroyl sarcosin), can be subjected to one or more freeze-thaw cycles using, e.g., liquid nitrogen or dry ice, can be subjected to sonication, or can be subjected to combinations thereof. The resulting sample can be subjected to a standard nucleic acid extraction technique such as those described elsewhere (e.g., Sambrook and Russell, (2001) Molecular Cloning: A Laboratory Manual, Third Edition, Cold Spring Harbor Press) or a nucleic acid extraction technique that includes the use of magnetic beads or selective DNA-binding membranes (see, e.g., QIAGEN DNeasy® Blood & Tissue Kit, or Mo Bio PowerFood® Microbial DNA Isolation Kit). For example, the blood sample can be contacted with magnetic beads that bind nucleic acid, the beads can be removed, and bound nucleic acid can be eluted into an appropriate buffer to form a processed sample for further analysis using the methods and materials provide herein. Such a process can be carried out using a variety of kits including, without limitation, Qiagen BioSprint 96 One-For-All Vet Kit (a rapid and economical automated purification of viral nucleic acid and/or bacterial nucleic acid from samples based on magnetic beads) and Chemicell geneMAG-PCR cleanup kit. In some cases, a sample (e.g., a blood sample or body fluid sample) can be subjected to DNA isolation using Qiagen QIAcard FTA Spots or Qiagen QIAamp UltraSens Virus Kits.

In some cases, a sample can be processed in a manner designed to fragment any nucleic acid present within the sample. For example, genomic or large pieces of nucleic acid present within a sample can be subjected to a sonication technique, nebulization technique, and/or restriction digestion with a restriction endonuclease such as DpnII or CviJI to generate nucleic acid fragments. Such fragmentation can be performed using restriction endonucleases that are different from those used as recognition or amplifying restriction endonucleases to assess the sample as described herein.

In some cases, the sample can be treated such that any double-stranded nucleic acid present within the sample is separated. For example, a biological sample can be heated and then snap-cooled or can be subjected to chemical (e.g., sodium hydroxide) denaturation. In some cases, when the sample is subjected to a PCR-based technique, certain primer or reaction modifications can be used to generate preferentially single-stranded product. For example, unidirectional DNA polymerase reactions can be performed with a single specific primer. In some cases, the strands of nucleic acid can be separated, and the strand of interest can be enrichment using specific biotinylated primers and streptavidin-conjugated magnetic beads. In some cases, selective digestion of one of the strands can be accomplished using lambda exonucleases.

As described herein, a sample (e.g., a biological sample) can be subjected to a nucleic acid amplification technique. For example, a tissue sample containing extracted nucleic acid can be subjected to a quick PCR-based amplification of one or more specific targets (e.g., 1 hour, end-point PCR) or to a whole genome amplification technique (e.g., Qiagen REPLI-g Screening Kit for high-throughput manual or automated whole genome amplification).

Once obtained, a sample to be assessed, whether subjected to a PCR-based nucleic acid technique or not, can be contacted with a probe nucleic acid as described herein. This contacting step can be carried out for any period of time and at any temperature that allows target nucleic acid to hybridize with probe nucleic acid. For example, this step can be performed between 10 seconds and 24 hours (e.g., between 30 seconds and 12 hours, between 30 seconds and 8 hours, between 30 seconds and 4 hours, between 30 seconds and 2 hours, between 30 seconds and 1 hour, between 1 minute and 24 hours, between 1 minute and 12 hours, between 1 minute and 8 hours, between 1 minute and 4 hours, between 1 minute and 2 hours, between 1 minute and 1 hour, between 5 minutes and 1 hour, between 10 minutes and 1 hour, between 15 minutes and 1 hour, or between 30 minutes and 1 hour). The initial temperature can be between 15° C. and 100° C. (e.g., between 23° C. and 98° C., between 23° C. and 90° C., between 23° C. and 85° C., between 23° C. and 75° C., between 23° C. and 65° C., between 23° C. and 55° C., between 23° C. and 45° C., between 23° C. and 35° C., between 30° C. and 95° C., between 30° C. and 85° C., between 30° C. and 75° C., between 30° C. and 65° C., between 30° C. and 55° C., between 30° C. and 45° C., between 20° C. and 40° C., between 20° C. and 30° C., and between 25° C. and 35° C.). The temperature during this contacting step can remain constant or can be increased or decreased. For example, the initial temperature can be between about 40° C. and about 85° C., and then the temperature can be allowed to decrease to room temperature over a period of about 30 seconds to about 30 minutes (e.g., between about 30 seconds and about 15 minutes, between about 30 seconds and about 10 minutes, between about 1 minute and about 30 minutes, between about 1 minute and about 15 minutes, or between about 1 minute and about 5 minutes).

Contact of the sample (e.g., a biological sample to be tested) with probe nucleic acid can occur in the presence of the recognition restriction endonucleases, or a separate step of adding the recognition restriction endonucleases to the reaction can be performed. The recognition restriction endonuclease step can be carried out for any period of time and at any temperature that allows the recognition restriction endonuclease to cleave recognition restriction endonuclease cut sites formed by the hybridization of target nucleic acid to the probe nucleic acid. For example, this step can be performed between one second and 24 hours (e.g., between one second and 30 minutes, between one second and one hour, between five seconds and one hour, between 30 seconds and 24 hours, between 30 seconds and 12 hours, between 30 seconds and 8 hours, between 30 seconds and 4 hours, between 30 seconds and 2 hours, between 30 seconds and 1 hour, between 1 minute and 24 hours, between 1 minute and 12 hours, between 1 minute and 8 hours, between 1 minute and 4 hours, between 1 minute and 2 hours, between 1 minute and 1 hour, between 5 minutes and 1 hour, between 10 minutes and 1 hour, between 15 minutes and 1 hour, or between 30 minutes and 1 hour). The temperature can be between 15° C. and 75° C. (e.g., between 15° C. and 75° C., between 15° C. and 65° C., between 15° C. and 55° C., between 15° C. and 45° C., between 15° C. and 35° C., between 15° C. and 30° C., between 23° C. and 55° C., between 23° C. and 45° C., between 30° C. and 65° C., between 30° C. and 55° C., between 30° C. and 45° C., between 30° C. and 40° C., between 35° C. and 40° C., and between 36° C. and 38° C.). Any appropriate concentration of recognition restriction endonuclease can be used. For example, between about 0.001 units and 1000 units (e.g., between about 0.001 units and 750 units, between about 0.001 units and 500 units, between about 0.001 units and 250 units, between about 0.001 units and 200 units, between about 0.001 units and 150 units, between about 0.001 units and 100 units, between about 0.001 units and 50 units, between about 0.001 units and 25 units, between about 0.001 units and 10 units, between about 0.001 units and 1 unit, between about 0.001 units and 0.1 units, between about 0.01 units and 1000 units, between about 0.1 units and 1000 units, between about 1 unit and 1000 units, between about 10 units and 1000 units, between about 50 units and 1000 units, between about 0.5 units and 100 units, or between about 1 unit and 100 units) of restriction endonuclease can be used.

Other restriction endonuclease reaction conditions such as salt conditions can be used according to the manufacturer's instructions.

When one step of a method provided herein is completed, the resulting reaction product containing cleaved nucleic acid can be used in the next step. For example, cleaved nucleic acid of a reaction product can be removed from uncleaved nucleic acid and used in the next step of the method. For example, when probe nucleic acid is attached to a solid support, the released portions of probe nucleic acid that contain an amplifying restriction endonuclease can be collected and placed in contact with reporter nucleic acid or signal expansion nucleic acid as described herein. The resulting reaction products of a particular step can be manually or automatically (e.g., robotically) transferred to a location containing nucleic acid for the next step (e.g., reporter nucleic acid or signal expansion nucleic acid), which nucleic acid can be attached or not attached to a solid support. In some cases, one reaction of a method described herein can be carried out at one location (e.g., a chamber) of a microfluidic device or blister package device, and the reaction products that are generated can be moved to another location (e.g., another chamber) that contains nucleic acid for the next step (e.g., reporter nucleic acid or signal expansion nucleic acid) via a channel. In some cases, cleaved nucleic acid of a reaction product can be used in the next step of the method by removing the uncleaved nucleic acid from the reaction product. For example, when magnetic beads are used as a solid support, a magnetic force can be used to remove the magnetic beads and any attached uncleaved nucleic acid from the reaction product. In some cases, two or more reactions of a method provided herein can be carried out at one location (e.g., a single well of a microtiter plate or a single chamber of a microfluidic device). For example, a single compartment can have one region that contains immobilized probe nucleic acid and another region that contains immobilized reporter nucleic acid provided that the amplifying restriction endonuclease of the immobilized probe nucleic acid is not capable of cleaving the amplifying restriction endonuclease cut site of the reporter nucleic acid unless target nucleic acid hybridizes to the probe nucleic acid and the recognition restriction endonuclease cleaves the probe nucleic acid, thereby releasing a portion of the probe nucleic acid that contains the amplifying restriction endonuclease so that it is capable of cleaving the reporter nucleic acid. In another example, a single compartment can have one region that contains immobilized probe nucleic acid, other regions that contain immobilized signal expansion nucleic acid (e.g., one region that contains a first signal expansion nucleic acid and another region that contains a second signal expansion nucleic acid), and another region that contains immobilized reporter nucleic acid provided that the amplifying restriction endonucleases of immobilized probe nucleic acid and signal expansion nucleic acid are not capable of cleaving their intended amplifying restriction endonuclease cut sites until they are released as described herein. Such single compartments can be made using partitions or sub-compartments within the single compartment. For example, a sample to be tested can be placed into a single well of a microtiter plate that contains probe nucleic acid, recognition restriction endonucleases, first and second signal expansion nucleic acid, and reporter nucleic acid such that cleaved reporter nucleic acid and/or signal expansion nucleic acid is produced as described herein when target nucleic acid is present in the sample being tested and little or no cleaved reporter nucleic acid and/or signal expansion nucleic acid is produced when target nucleic acid is not present in the sample being tested.

Any appropriate method can be used to detect cleaved reporter nucleic acid and/or signal expansion nucleic acid to determine the presence, absence, or amount of target nucleic acid in a sample, which can indicate the presence, absence, or amount of a target genetic or epigenetic element. For example, size separation techniques can be used to assess reaction products for cleaved reporter nucleic acid and/or signal expansion nucleic acid. Examples of such size separation techniques include, without limitation, gel electrophoresis and capillary electrophoresis techniques. In some cases, a melt curve analysis can be performed to assess reaction products for cleaved reporter nucleic acid and/or signal expansion nucleic acid. As described herein, a label can be used to aid in the detection of cleaved nucleic acid (e.g., reporter nucleic acid and/or signal expansion nucleic acid). Examples of labels that can be used include, without limitation, fluorescent labels (with or without the use of quenchers), dyes, antibodies, radioactive material, enzymes (e.g., horse radish peroxidase, alkaline phosphatase, laccase, galactosidase, or luciferase), redox labels (e.g., ferrocene redox labels), metallic particles (e.g., gold nanoparticles), and green fluorescent protein based labels. For example, the release of fluorescently labeled portions of reporter nucleic acid and/or signal expansion nucleic acid from a solid support can be assessed using common fluorescent label detectors. In some cases, cleaved reporter nucleic acid and/or signal expansion nucleic acid can be detected electrochemically. For electrochemical detection, the reporter nucleic acid and/or signal expansion nucleic acid can include a ferrocene redox label. Reporter nucleic acid and/or signal expansion nucleic acid containing ferrocene can be obtained by coupling ferrocene carboxylic acid with an amino-modified oligonucleotide using the carbodiimide reaction in the presence of an excess of ferrocene carboxylic acid. In one embodiment, for a redox label, such as ferrocene, the detector can be an electrode for amperometric assay of redox molecules. For example, if the redox label is present in a reduced form of ferrocene, then the electrode at high electrode potential can provide an oxidation of the reduced form of ferrocene, thereby converting it to an oxidized form of ferrocene. The generated current can be proportional to the concentration of ferrocene label in the solution.

The methods and materials provided herein can be used to assess one or more samples for target nucleic acid in real-time. For example, a fluorescent label/quencher system or an electrochemical redox label system can be used to detect cleavage of reporter nucleic acid and/or signal expansion nucleic acid in real time.

The methods and materials provided herein can be used to assess one or more samples (e.g., two, three, four, five, six, seven, eight, nine, ten, 20, 50, 100, 500, 1000, or more) for a single type of target nucleic acid. For example, 100s of tissue samples (e.g., tissue biopsy samples) can be assessed for target nucleic acid containing a particular genetic or epigenetic element. In some case, the methods and materials provided herein can be used in a multiplex manner to assess one or more samples for more than one (e.g., two, three, four, five, six, seven, eight, nine, ten, 20, 50, 100, 500, 1000, or more) type of target nucleic acid. For example, target nucleic acid for ten different sequences (e.g., ten different SNP sequences) can be used to design ten different probe nucleic acid molecules. In these cases, each probe nucleic acid can be used in a separate series of reactions within the same device (e.g., microtiter plate or microfluidic device), and the same label can be used for the reporter nucleic acid for each probe nucleic acid. In addition, in some cases, the same amplifying restriction endonuclease can be used for each probe nucleic acid, and the same reporter nucleic acid can be used for each reaction series. In some cases, when multiple different probe nucleic acid molecules are used in the same reaction series, a different reporter nucleic acid having different labels can be used to correspond to each probe nucleic acid such that the detected signals can indicate which of the ten target nucleic acids are being detected.

This document also provides kits for performing the methods described herein. For example, a kit provided herein can include probe nucleic acid with or without being attached to a solid support and/or reporter nucleic acid with or without being attached to a solid support. In some cases, such a kit can include a recognition restriction endonuclease, first signal expansion nucleic acid, second signal expansion nucleic acid, or a combination thereof. In some cases, a kit can be configured into a microfluidic device that allows for the movement of probe nucleic acid, first signal expansion nucleic acid, second signal expansion nucleic acid, reporter nucleic acid, or recognition restriction endonucleases (or any combination thereof) as well as a cleaved portion of any such nucleic acid in a manner that allows a detection method provided herein to be carried out with or without the nucleic acid being attached to a solid support. For example, a kit provided herein can be a microfluidic device capable of receiving a sample and contacting that sample with probe nucleic acid. The probe nucleic acid can be designed to include a length of nucleotides followed by the sequence complementary to the target nucleic acid, which can create a recognition restriction endonuclease cut site, followed by an amplifying restriction endonuclease. The distance from the recognition restriction endonuclease cut site to the amplifying restriction endonuclease can be relatively short (e.g., 100, 50, 25, 10, or less nucleotides), while the distance from the recognition restriction endonuclease cut site to the beginning of the length of nucleotides can be relatively long (e.g., 50, 100, 150, 200, 500, 1000, 2000, or more). In such cases, cleavage of the probe nucleic acid at the recognition restriction endonuclease cut site can result in a relatively small portion that contains the amplifying restriction endonuclease and is capable of travelling faster than the larger uncleaved probe nucleic acid. This difference can allow the cleaved portion containing the amplifying restriction endonuclease to reach an area of the microfluidic device containing signal expansion nucleic acid or reporter nucleic acid so that the next reaction can be carried out without the presence of uncleaved probe nucleic acid. In some cases, after the smaller portion containing the amplifying restriction endonuclease enters the area containing signal expansion nucleic acid or reporter nucleic acid, a valve can be used to prevent the larger uncleaved probe nucleic acid from entering. In some cases, a filter can be used to limit the ability of larger uncleaved probe nucleic acid from proceeding to the next reaction location. Similar approaches can be used during other steps of a method provided herein to separate cleaved nucleic acid from uncleaved nucleic acid.

In some cases, a kit provided herein can be a portable or self-contained device, packet, vessel, or container that can be used, for example, in point of care applications. For example, such a kit can be configured to allow a patient or physician's assistant to insert a sample for analysis. In some cases, a kit can be designed for use in a home setting or any other setting. Once inserted, the sample can be heated (e.g., heated to about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 75, 80, 85, 90, 95, or more ° C.) and/or cooled by a heating or cooling mechanism located within the kit. For example, an exothermic or endothermic chemical reaction can be initiated within the kit to increase, decrease, or maintain the temperature. Such exothermic or endothermic chemical reactions can be carried out within the kit without being in fluid communication with the reactions of the target nucleic acid detection method. An iron oxidation reaction is an example of an exothermic chemical reaction that can be used to heat a kit provided herein. An endothermic chemical reaction that can be used to cool a kit provided herein can be a reaction that includes the use of ammonium chloride and water, potassium chloride and water, or sodium carbonate and ethanoic acid. In general, when detecting DNA target nucleic acid, the kit can be designed to generate, if needed, enough heat to denature double stranded DNA present within the sample. The kit also can be designed to generate appropriate heating and cooling temperatures to carry out each step of a detection method provided herein. In some cases, a kit provided herein can include a temperature indicator (e.g., color indicator or thermometer) to allows a user to assess temperature.

In some cases, a kit can be designed to provide a user with a "yes" or "no" indication about the presence of target nucleic acid within a tested sample. For example, a label having the ability to generate a change in pH can be used, and a visual indicator (e.g., a pH-based color indicator) can be used to inform the user of the presence of target nucleic acid based on a change in pH.

In some cases, a point of care or home use device can be designed to carry out the reactions described herein. For example, point of care or home use device can be designed to include a series of adjacent chambers. In a relatively simple configuration, for example, a first "sample" chamber can be configured for sample insertion, and can contain reagents (e.g., in dry or liquid form) to effect generation of single stranded nucleic acid fragments. A second "recognition" chamber can be configured to receive single stranded nucleic acid fragments from the first chamber, and can contain probe nucleic acid and recognition restriction endonuclease (e.g., in dry or liquid form). A third "amplification" chamber can be configured to receive cleaved portions of probe nucleic acid from the second chamber, and can contain reporter nucleic acid (e.g., in dry or liquid form). A fourth "detection" chamber can be configured to receive cleaved portions of marker nucleic acid from the third chamber, and can contain a reagent (e.g., in dry or liquid form) that serves as an indicator of whether or not target nucleic acid was present in the sample. It is noted that one or more additional "signal expansion" chambers can be present between the "recognition" chamber and the "amplification" chamber.

In some cases, a point of care or home use device can be configured such the chambers are separated from each other by membranes that can provide controlled passage of reaction materials. For example, chambers can be separated by membranes that are subject to degradation by particular reagents or solutions. In such cases, a reaction can be confined to a particular chamber until the membrane separating it from the adjacent chamber degrades, permitting passage of reaction components there between.

In some cases, a point of care or home use device can be adapted for automatic transfer of the reaction mixture between chambers. For example, insertion of a sample into the first chamber can trigger a reaction or provide a reagent that gradually degrades the membrane separating the first chamber from the second chamber. Movement of all or a portion of the reaction mixture into the second chamber can in turn provide a reagent or trigger a reaction that gradually degrades the membrane separating the second chamber from the third chamber. For example, if the sample reaction mixture in the first chamber is an aqueous solution, the reagents in the second chamber are dry, and the membrane in the second chamber is degraded by water, movement of the aqueous reaction mixture into the second chamber can trigger degradation of the membrane therein.

In some cases, a point of care or home use device can be adapted for automatic controlled flow transfer of reaction mixture between chambers. For example, insertion of a sample into the first chamber can trigger a reaction or provide a reagent that allows controlled flow movement of the sample through absorption media. Movement of all or a portion of the reaction mixture into the second chamber can in turn provide a reagent or trigger a reaction that allows controlled flow movement of the sample through absorption media to a third chamber. In such cases, a reaction can be confined to a particular chamber until the media separating it from the adjacent chamber absorbs and permits passage of reaction components there between.

In some cases, a point of care or home use device can be adapted for automatic controlled flow transfer of reaction mixture between chambers. For example, insertion of a sample into the first chamber can trigger a reaction or provide a reagent that allows controlled capillary flow movement of the sample through micro-fluidic channels. Movement of all or a portion of the reaction mixture into the second chamber can in turn provide a reagent or trigger a reaction that allows controlled flow movement of the sample through micro-fluidic channels to a third chamber. In such cases, a reaction can be confined to a particular chamber until the microfluidic channel permits passage of reaction components there between.

In some cases, a point of care or home use device can be adapted for automatic controlled flow transfer of reaction mixture without chambers. For example, insertion of a sample into the device can trigger a reaction or provide a reagent that allows controlled capillary flow movement of the sample through microfluidic channels. Movement of all or a portion of the reaction mixture in the microfluidic channel can trigger a reaction that allows reagents to enter the reaction mixture in a continuous flow-through manner with no specific chamber for a reaction. In such cases, a reaction does not need to be confined to a particular section of the microfluidic channel.

Figure 7:
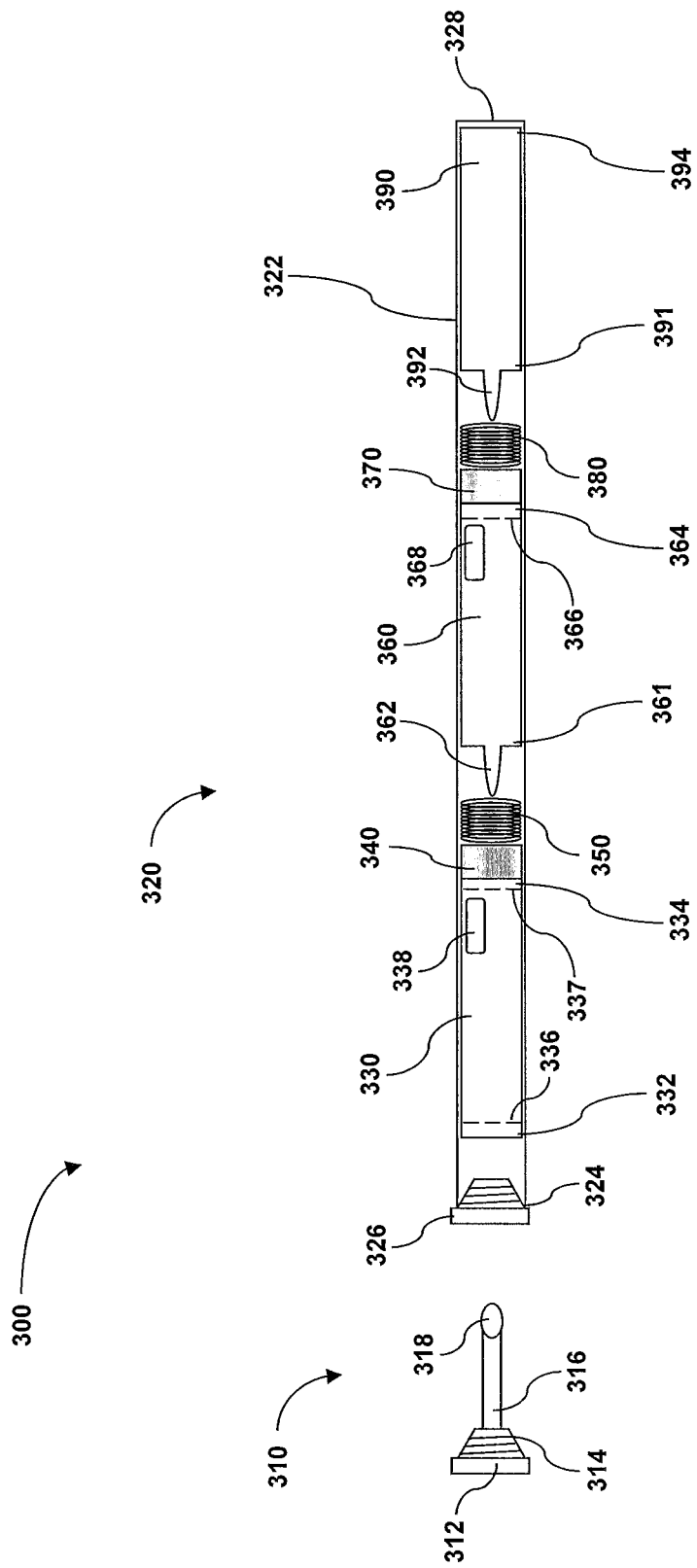
FIG. 7 is a schematic of an exemplary configuration for a single-use, pen-style point of care device.

In some cases, transfer of a reaction mixture from one chamber to the next can be controlled by a user. An exemplary user-controlled, pen-style point of care or home use device is depicted in FIG. 7. Device 300 can include sample collector 310 and reaction unit 320. Sample collector 310 can have cap 312 with screw threads 314, shaft 316, and swabber 318. Swabber 318 can be smooth or rough, and in some cases can have bristles (e.g., smooth or rough bristles) or a matted texture to facilitate sample collection from, for example, the inside cheek, throat, or skin of an individual to be tested.

Reaction unit 320 can include tube 322, open end 324 reversibly closed by safety cap 326, and closed end 328. Open end 324 can have internal screw threads, and cap 326 can have external screw threads 329. Screw threads 329 of safety cap 326, as well as screw threads 314 of sample collector cap 312, can be adapted to mate with the internal screw threads at open end 324, such that either safety cap 326 or sample collector 310 can be screwed into open end 324.

Tube 322 can contain several chambers, such as lysing and isolation chamber 330, recognition and amplification chamber 360, and detection chamber 390. As described herein, the chambers can be separated from one another to prevent premature mixing of reaction components. Tube 322 and the chambers contained therein can be made from, for example, clear plastic (e.g., polycarbonate, acrylic, nylon, or PVC). Tube 322 also can contain first and second safety bands 340 and 370, and first and second spring returns 350 and 380.

Lysing and isolation chamber 330 can be positioned proximal to open end 324. Lysing and isolation chamber 330 can have proximal end 332, distal end 334, proximal membrane 336, distal membrane 337, and reaction completion indicator 338. Proximal membrane 336 can be located adjacent to proximal end 332, and distal membrane 337 can be located adjacent to distal end 334. Membranes 336 and 337 can be made from, for example, synthetic rubber, natural latex rubber, or silicone. Chamber 330 can contain reagents for lysing cells as well as reagents for cleaving and denaturing cellular nucleic acids. Reaction completion indicator 338 can be, for example, a built in timer or stop watch, a built in pH indicator, a built in color change reagent, or a conductivity probe, and can indicate when cell lysis and nucleic acid sample generation are sufficient to proceed to the next step.

First safety band 340 can be positioned distal to lysing and isolation chamber 330 within tube 322, and first spring return 350 can be positioned distal to first safety band 340. First safety band 340 can be, for example, connected to a tab or strap, and can be moved or removed from reaction unit 320 by pulling on the tab or strap. First spring return 350 can be made from a shape memory material that can be compressed and then automatically return to or toward its original configuration.

The safety band 340 can be attached to the tube as a secured ring that can be, for example, over molded as a soft rubber component or inserted as a spring like split ring component. The safety band 340 can lock the position of the lysing and isolation tube chamber 340, preventing linear sliding of the lysing and isolation chamber 330 to that of the recognition and amplification chamber 360. Upon removal of safety band 340, the user can actuate linear movement of the entire device 300 by holding the proximal end firm and pressing the distal closed end 328 such that both distal chambers recognition and amplification 360 and detection chamber 390 are moved toward the lysing and isolation chamber 330. The needle and sample collector 362 can pierce membrane 337 and enter the lysing and isolation chamber 330. The user can release a firm hold on the assembly and spring return 350 can draw the sample into recognition and amplification chamber 360. After completion of the reaction, the user can remove safety band 370, and the user can actuate linear movement of the assembly by holding the recognition and amplification chamber 360 firm and pressing the distal closed end 328 such that the detection chamber 390 moves toward the recognition and amplification chamber 360. The needle and sample collector 392 can pierce membrane 366. The user can release the firm hold on the assembly, and spring return 380 can draw the sample into detection chamber 390.

Recognition and amplification chamber 360 can be positioned distal to first spring return 350. Chamber 360 can have proximal end 361, which in turn can have piercing needle and sample collector 362, distal end 364, membrane 366, and reaction completion indicator 368. Recognition and amplification chamber 360 can contain, for example, probe nucleic acid and reporter nucleic acid and restriction endonucleases for use in enzymatic amplification cascades as described herein. Piercing needle and sample collector 362 can have a pointed, beveled, or barbed tip. In addition, the interior of piercing needle and sample collector 362 can be in fluid communication with the interior of recognition and amplification chamber 360, such that a nucleic acid test sample can be collected from lysing and isolation chamber 330 and transferred to recognition and amplification chamber 360 via collector 362. Membrane 364 can be located adjacent to distal end 364, and can be made from, for example, synthetic rubber, natural latex rubber, or silicone. Reaction completion indicator 368 can be, for example, a built in timer or stop watch, a built in pH indicator, a built in color change reagent, or a conductivity probe, and can indicate when cell lysis and nucleic acid sample generation are sufficient to proceed to the next step.

Second safety band 370 can be positioned distal to recognition and amplification chamber 360 within tube 322, and second spring return 380 can be positioned distal to second safety band 370. Second safety band 370 can be, for example, connected to a tab or strap, and can be moved or removed from reaction unit 320 by pulling on the tab or strap. Second spring return 380 can be made from a shape memory material (e.g., spring steel, plastic, or rubber) that can be compressed and then automatically return to or toward its original configuration.

Detection chamber 390 can be positioned distal to second spring return 380, adjacent to closed end 328 of tube 322. Detection chamber 390 can have proximal end 391, which in turn can have piercing needle and sample collector 392, and distal end 394. Piercing needle and sample collector 392 can have a pointed, beveled, or barbed tip. In addition, the interior of piercing needle and sample collector 392 can be in fluid communication with the interior of detection chamber 390, such that a reaction sample can be collected from recognition and amplification chamber 360 and transferred to detection chamber 390 via collector 392. Detection chamber 390 can contain a substrate for an enzyme marker such as a substrate for horseradish peroxidase (HRP) (e.g., ABTS, TMB, OPD) or alkaline phosphatase (AP) (e.g., PNNP).

Sample collector 310 and reaction unit 320 can be packaged together and sold as a kit. In use, the sample collector 310 can be removed from the package, and a swab can be obtained from, for example, a subject's body. Cap 326 can be removed from open end 324 of tube 322, and sample collector 310 can be screwed into open end 324 such that all or a portion of swabber 318 extends through proximal membrane 336 and into the interior of lysing and isolation chamber 330. The sample can be mixed (e.g., by shaking), and the lysing and nucleic acid preparation can proceed for a particular length of time, or until reaction completion indicator 338 indicates that the user can proceed to the next reaction step.

When the nucleic acid sample is ready, the user can remove first safety band 350 from reaction unit 320, and can actuate reaction unit 320 such that piercing needle and sample collector 362 moves proximally to penetrate distal membrane 337 of lysing and isolation chamber 330, collects a sample from chamber 330, and, by virtue of first spring return 350, moves distally to its original position. The sample can again be mixed, and the recognition and amplification steps can proceed for a particular length of time, or until reaction completion indicator 368 indicates that the user can proceed to the next reaction step.

When the reaction sample is ready, the user can remove second safety band 380 from reaction unit 320, and can actuate reaction unit 320 such that piercing needle and sample collector 392 moves proximally to penetrate membrane 366 of recognition and amplification chamber 360, collects a sample from chamber 360, and, by virtue of second spring return 380, moves distally to its original position. The sample can again be mixed, and marker released during the amplification step can be detected (e.g., colorimetrically or fluorescently). In some cases, the outer surface of tube 322 can have a color code printed thereon, so a user can compare the color of detection chamber 390 with the color code to determine whether or not the tested sample contains target nucleic acid.

Device 300 can have any suitable dimensions. For example, the size of device 300 can approximate that of a pen or a marker, which can make it particularly convenient to transport. In some cases, device 300 can have a diameter at its widest point of about 0.25 to about 2 cm (e.g., 0.25, 0.3, 0.4, 0.5, 0.6, 0.75, 0.8, 0.9, 1, 1.1, 1.2, 1.3, 1.4, 1.5, 1.6, 1.7, 1.8, 1.9, or 2 cm), and a length of about 5 cm to about 200 cm (e.g., 5, 10, 15, 20, 25, 30, 40, 50, 60, 70, 80, 90, 100, 110, 120, 130, 140, 150, 160, 170, 180, 190, or 200 cm).

The invention will be further described in the following examples, which do not limit the scope of the invention described in the claims.

EXAMPLES

Example 1—Formation and Cleavage of Target-Probe Hybrids

An oligonucleotide probe (5'-thiol-GGT AGT GCG AAA TGC CAT TGC TAG TTG TTT-biotin-3'; SEQ ID NO:2) that was modified with a thiol group at the 5' end and a biotin molecule at the 3' end was conjugated to horseradish peroxidase (HRP). Conjugation was performed using the SMCC reagent according to a technique modified from Dill et al. (*Biosensors and Bioelectronics*, 20:736-742 (2004)). The HRP conjugate solution was incubated with a streptavidin-coated ELISA plate to immobilize the HRP-oligonucleotide probe to the surface via a biotin-streptavidin interaction. The ELISA plate was then incubated with different concentrations of a target oligonucleotide (5'-AAA CAA CTA GCA ATG GCA TTT-3'; SEQ ID NO:3). The target oligonucleotide sequence was reverse-complementary to the probe sequence to form a double-stranded hybrid molecule. After washing, the plate was incubated in a solution containing the restriction endonuclease BfaI. BfaI specifically recognizes the sequence 5'-CTAG-3' and cleaves the double-stranded, target-probe hybrids to release the HRP-oligonucleotide into the reaction solution. After a two-hour incubation at 37° C., the reaction solution was transferred to a new ELISA plate. The cleaved HRP-oligonucleotide was contacted to 3,3',5,5'-tetramethyl benzidine (TMB) to form a colored reaction product.

Figure 6:
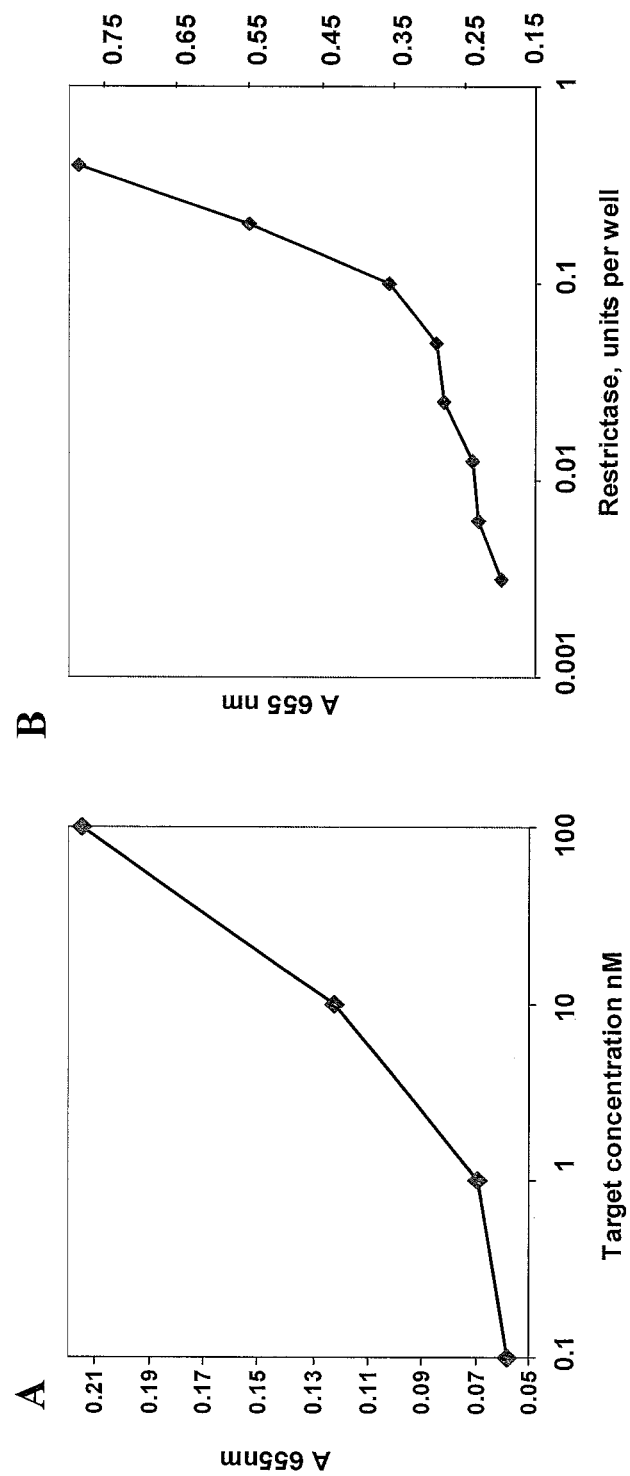
FIG. 6 contains line graphs demonstrating the effect of target oligonucleotide concentration (A) and recognition restriction endonuclease concentration (B) on the cleavage of HRP-labeled nucleic acid as detected by the formation of colored reaction product.

When the restriction endonuclease BfaI was added in excess to the reaction mixture, a clear direct dependence between the amount of released HRP-probe and the concentration of oligonucleotide target was observed (FIG. 6A). The detectable target concentration was approximately 1 nM. This detection limit was obtained by direct measurement without any secondary signal amplification. The addition of a restriction endonuclease signal amplification cascade as described herein can further improve the detection limit by several orders of magnitude.

When the HRP-oligonucleotide probes were pre-incubated with an excess of target oligonucleotide (500 nM), the amount of cleaved HRP-oligonucleotide probe was limited by the amount of recognition restriction endonuclease BfaI (FIG. 6B). Taken together, these data demonstrate that recognition restriction endonucleases can be used to initiate the restriction endonuclease cascades described herein.

Example 2—Detecting Target Nucleic Acid Using Probe Nucleic Acid and Reporter Nucleic Acid A target nucleic acid is selected. Once selected, target nucleic acid is analyzed using a common genetic database such as GenBank® and/or a computer-based sequence analysis program to identify a portion of the target nucleic acid that contains a cut site for a restriction endonuclease. Probe nucleic acid is designed to be complementary to at least a portion of target nucleic acid that contains a cut site. Once designed and obtained by standard oligonucleotide synthesis methods, probe nucleic acid is conjugated to an amplifying restriction endonuclease and immobilized to the surface of a first well of a microtiter plate. A sample to be tested is incubated in the first well. If target nucleic acid is present in the sample, at least a portion of the target nucleic acid hybridizes to the probe nucleic acid, and thereby forms a recognition restriction endonuclease cut site. The recognition restriction endonuclease is added to the first well having the sample and probe nucleic acid. The microtiter plate is incubated at 37° C. for an appropriate length of time for the cleavage reaction to proceed.

Upon cleavage of probe nucleic acid by the recognition restriction endonuclease, the reaction solution containing the released portion of the probe nucleic acid is transferred into a second well. The second well contains reporter nucleic acid that is immobilized to the surface and contains at least one double-stranded portion having an amplifying restriction endonuclease cut site. Reporter nucleic acid also has a fluorescent label. Upon transfer to the second chamber, the amplifying restriction endonuclease bound to the released portion of the probe nucleic acid contacts the reporter nucleic acid. The amplifying restriction endonuclease cleaves reporter nucleic acid at the double-stranded amplifying restriction endonuclease cut site to form at least two portions. The liberated portion of the reporter nucleic acid having the fluorescent label is moved to a third microtiter plate well, and a standard fluorescent reader is used to measure any fluorescent signal.

A standard curve of known amounts of target nucleic acid is used to quantify the amount of target nucleic acid in the tested sample.

Example 3—Detecting Target Nucleic Acid Using Probe Nucleic Acid, First Signal Expansion Nucleic Acid, Second Signal Expansion Nucleic Acid, and Reporter Nucleic Acid Once selected, target nucleic acid is analyzed using a common genetic database such as GenBank® and/or a computer-based sequence analysis program to identify a portion of target nucleic acid that contains a cut site for a restriction endonuclease. Probe nucleic acid is designed based on the desired target nucleic acid as described herein. Standard oligonucleotide synthesis methods are used to make the probe nucleic acid, which is then conjugated to an initial amplifying restriction endonuclease and immobilized to the surface of a first well of a microtiter plate. A sample to be tested for the target nucleic acid is incubated in the first well. If target nucleic acid is present in the sample, at least a portion of target nucleic acid hybridizes to probe nucleic acid and thereby forms a recognition restriction endonuclease cut site. Recognition restriction endonuclease is added to the first well having the sample and probe nucleic acid. The microtiter plate is incubated at 37° C. for an appropriate length of time for the cleavage reaction to proceed.

After cleavage of the probe nucleic acid:target nucleic acid hybrid by the recognition restriction endonuclease, the reaction solution containing the free portion of probe nucleic acid is transferred to another well that includes first signal expansion nucleic acid and second signal expansion nucleic acid. The first signal expansion nucleic acid and second signal expansion nucleic acid creates a positive feedback loop that causes an exponential acceleration of release of initial amplifying restriction enzymes. The reaction product from this well is transferred to another well containing reporter nucleic acid, and cleavage of the reporter nucleic acid is used to determine the presence, absence, or amount of target nucleic acid in the sample. A standard curve of known amounts of target nucleic acid is used to quantify the amount of target nucleic acid in the tested sample.

Example 4—Detecting Methylated Cyclin D2 Promoter in Circulating Blood of Breast Cancer Patients The presence or absence methylated cyclin D2 promoter in circulating blood of breast cancer patients can be indicative of breast cancer lesions (Rykova et al., Ann. N.Y. Acad. Sci., 1137:232-235 (2008)). The presence or absence of methylated cyclin D2 promoter is determined in total circulating DNA (cirDNA) from the blood that can include cell-free and cell-surface-bound DNA fractions isolated as described elsewhere (e.g., Sunami et al., Methods Mol. Biol., 507:349-356 (2009)). The presence or absence methylated cyclin D2 promoter is detected using an enzymatic amplification cascade. The gene for cyclin D2 (CCDN2, G1/S-specific cyclin-D2; Ensembl ID: ENSG00000118971) is located in the forward strand of human Chromosome 12 at position 4,382,902-4,414,521. Its promoter is composed of at least 7 fragments, and the longest 700 bp fragment (sequence ID ENSR00000172023; chromosome 12 positions 4386022-4386721) was analyzed using the Ensembl ("http" colon, slash, slash "uswest" dot "ensemble" dot "org" slash "index" dot "html") genetic database and CLC DNA Workbench software to identify a portion of target sequence with a cut site for the MspI/HpaII restriction endonucleases, which cleave at the 4 bp nucleotide sequence 5'-CCGG-3'. A 40 nt probe nucleic acid (5'-GTTTAT-TGGGGTGCTTTACCCCGGCTGTACACAGAAAGCC-3' (SEQ ID NO:4)) was designed to be complementary to nucleotides 520 to 559 of the selected target nucleic acid (chromosome 12 positions 4386542-4386581).

Once designed and obtained by standard oligonucleotide synthesis methods, probe nucleic acid is conjugated to an amplifying restriction endonuclease and immobilized to the surface of two wells of a microtiter plate. A sample of circulating DNA to be tested is obtained from patient blood or body fluids, and added to the two wells. If the cyclin D2 promoter sequence is present in circulating DNA, it will bind to the probe in both wells thereby forming a CCGG restriction site for the MspI recognition restriction endonuclease, which is methylation insensitive, and the HpaII recognition restriction endonuclease, which is methylation sensitive. MspI and HpaII are either added or present in the first and second wells, respectively, and they are allowed to cleave any formed recognition restriction endonuclease cut sites by incubating the microtiter plate at 37° C. for an appropriate length of time (e.g., 1 minute to 2 hours) for the cleavage reaction to proceed.

After cleavage of the probe nucleic acid:target nucleic acid hybrid by MspI and HpaII, the reaction solutions in the first and second wells are transferred to third and fourth wells, respectively, both containing reporter nucleic acid that is immobilized to the surface and that has at least one double-stranded portion having an amplifying restriction endonuclease NcoI cut site. The reporter nucleic acid can be a double-stranded nucleic acid having a first strand (e.g., 5'-CATTGCTAGTTGTTT CCATGGGGTAGTGCGAAATGC-3' (SEQ ID NO:5)) and a second strand (e.g., 5'-GCATTTCGCACTACCCCATG-GAAACAACTAGCAATG-3' (SEQ ID NO:6)). The reporter nucleic acid also has a fluorescent label. In some cases, first signal expansion nucleic acid and second signal expansion nucleic acid are used prior to the reporter nucleic acid step to increase the level of target nucleic acid detection. The first signal expansion nucleic acid and second signal expansion nucleic acid can include labels, in which case they can be used together with reporter nucleic acid or in place of reporter nucleic acid.

After transferring the reaction mixture to the third and fourth wells, the amplifying restriction endonucleases of the released portions of probe nucleic acid contact reporter nucleic acid, and the microtiter plate is incubated at an appropriate temperature (e.g., at 37° C.) for an appropriate length of time (e.g., 1 minute to 2 hours) for the cleavage reaction to proceed. The amplifying restriction endonucleases cleave reporter nucleic acid at the double-stranded amplifying restriction endonuclease cut site to form at least two portions. The reaction solutions of the third and fourth wells are transferred to fifth and six wells, respectively, for fluorescence detection using a fluorescent microtiter plate reader. The fluorescent signal in the fifth well (corresponding to the MspI recognition restriction endonuclease-treated well) is indicative of total amount of the cyclin D1 promoter in the circulating blood. The fluorescent signal in the sixth well (corresponding to the HpaII recognition restriction endonuclease-treated well) is indicative of the amount of unmethylated cyclin D1 promoter in the circulating blood. If the latter signal is smaller than the former signal then at least a part of the corresponding cyclin D2 promoter DNA is methylated. The proportion of methylated promoter can be calculated as a difference between the signal in the fifth well minus the signal in the sixth well.

Example 5—Detecting Methylated RASSF1A Promoter in Circulating Blood of Hepatocellular Carcinoma and Lung Cancer Patients The presence or absence methylated RASSF1A promoter in circulating blood of hepatocellular carcinoma and lung cancer patients is indicative of tumor growth and disease progression (Di Gioia et al., BMC Cancer, 6:89 (2006); Fischer et al., Lung Cancer, 56:115-123 (2007); and Allen Chan et al., Clin. Chem., 10:1373 (2008)). The presence or absence of methylated RASSF1A promoter is determined in total circulating DNA (cirDNA) from the blood that can include cell-free and cell-surface-bound DNA fractions isolated as described elsewhere (e.g., Sunami et al., Methods Mol. Biol., 507:349-356 (2009)).

The presence or absence methylated RASSF1A promoter is detected using an enzymatic amplification cascade. The gene for RASSF1A (Ras association domain-containing protein 1; Ensembl ID: ENSG00000068028) is located in the reverse strand of Chromosome 3 at positions 50,367,217-50,378,411. Its promoter is composed of at least three fragments, and the longest 1,702 bp fragment (sequence ID ENSR00000059407, Chromosome 3:50369843-50371544) was analyzed using the Ensembl (http://uswest.ensembl.org/index.html) genetic database and CLC DNA Workbench software to identify a portion of target sequence with cut sites for two restriction endonucleases, PstI and SmaI. PstI cleaves at the 6 bp nucleotide sequence 5'-CTGCAG-3', and a 40 nt probe nucleic acid (5'-AGTCCGAGTCCTCTTG-GCTGC-AGTAGCCACTGCTCGTCGT-3' (SEQ ID NO:7)) was designed to be complementary to nucleotides 503 to 542 of the selected target nucleic acid (Chromosome 3:50370346-50370385). SmaI cleaves at the 6 bp nucleotide sequence 5'-CCCGGG-3', and a 40 nt probe nucleic acid (5'-GTGTCAGTGTGCGCGTGCGCCCGGGCCAGAGC-CGCGCCGC-3' (SEQ ID NO:8)) was designed to be complementary to nucleotides 746 to 785 of the selected target nucleic acid (Chromosome 3:50370589-50370628). The PstI cut site is not methylated, and the SmaI cut site is a CpG island that can be methylated in cancer cells, and its methylation blocks cleavage by SmaI.

Once designed and obtained by standard oligonucleotide synthesis methods, probe nucleic acids are conjugated to an amplifying restriction endonuclease and immobilized to the surface of two wells of a microtiter plate. A sample of circulating DNA to be tested is obtained from patient blood or body fluids, and added to the two wells. If the RASSF1A promoter sequence is present in circulating DNA, it will bind to the probe nucleic acid in both wells thereby forming restriction sites for PstI and for SmaI in the first and second wells, respectively. PstI and SmaI are either added or present in the first and second wells, respectively, and they are allowed to cleave any formed recognition restriction endonuclease cut sites by incubating the microtiter plate at 37° C. for an appropriate length of time (e.g., 1 minute to 2 hours) for the cleavage reaction to proceed.

After cleavage of the probe nucleic acid:target nucleic acid hybrids by PstI or SmaI, the reaction solutions in the first and second wells are transferred to third and fourth wells, respectively, both containing reporter nucleic acid that is immobilized to the surface and that has at least one double-stranded portion having an amplifying restriction endonuclease NcoI cut site. The reporter nucleic acid can be a double-stranded nucleic acid having a first strand (e.g., 5'-CATTGCTAGTTGTTT CCATGGGGTAGTGCGAAATGC-3' (SEQ ID NO:5)) and a second strand (e.g., 5'-GCATTTCGCACTACCCCATG-GAAACAACTAGCAATG-3' (SEQ ID NO:6)). The reporter nucleic acid also has a fluorescent label. In some cases, first signal expansion nucleic acid and second signal expansion nucleic acid are used prior to the reporter nucleic acid step to increase the level of target nucleic acid detection. The first signal expansion nucleic acid and second signal expansion nucleic acid can include labels, in which case they can be used together with reporter nucleic acid or in place of reporter nucleic acid.

After transferring the reaction mixture to the third and fourth chambers, the amplifying restriction endonucleases of the released portions of probe nucleic acid contact reporter nucleic acid, and the microtiter plate is incubated at an appropriate temperature (e.g., at 37° C.) for an appropriate length of time (e.g., 1 minute to 2 hours) for the cleavage reaction to proceed. The amplifying restriction endonucleases cleave reporter nucleic acid at the double-stranded amplifying restriction endonuclease cut site to form at least two portions. The reaction solutions of the third and fourth wells are transferred to fifth and six wells, respectively, for fluorescence detection using a fluorescent microtiter plate reader. The fluorescent signal in the fifth well (corresponding to the PstI recognition restriction endonuclease-treated well) is indicative of total amount of the RASSF1A promoter in the circulating blood. The fluorescent signal in the sixth well (corresponding to the SmaI recognition restriction endonuclease-treated well) is indicative of the amount of unmethylated RASSF1A promoter in the circulating blood. If the latter signal is smaller than the former signal then at least a part of the corresponding RASSF1A promoter DNA is methylated. The proportion of methylated promoter can be calculated as the difference between the signal in the fifth well minus the signal in the sixth well.

Example 6—Assessing Alleles of the Thiopurine S-Methyltransferase Gene Based on a Sequence that Creates/Destroys a Restriction Endonuclease Site Thiopurine S-methyltransferase (EC 2.1.1.67) enzyme (TPMT) is a drug-metabolizing enzyme that catalyzes the S-methylation of thiopurine drugs such as 6-mecaptopurine and azathioprine that are used to treat childhood leukemia, autoimmune diseases, and transplant recipients (Wang et al., Proc. Natl. Acad. Sci. USA, 102(26):9394-9399 (2005)). These drugs can have potentially life-threatening drug-induced toxicity, depending on the levels of the TPMT enzyme in patient's tissues. Large individual variations in levels of TPMT activity are regulated primarily by common genetic polymorphisms with several most common alleles. Some of these alleles can result in a virtual lack of TPMT enzyme activity, and correspondingly, patients homozygous for these alleles can suffer severe, life-threatening toxicity when treated with standard doses of thiopurines.

The known SNP variants of the TPMT gene (Ensemble gene ID ENSG00000137364; positioned on Chromosome 6: 18,128,542-18,155,305 reverse strand) were analyzed using the Ensembl ("http" colon, slash, slash, "uswest" dot "ensemble" dot "org" slash "index" dot "html") genetic database and CLC DNA Workbench to determine whether these SNPs create or destroy restriction sites. One of these SNPs (Ensembl ID rs72552739; chromosome 6 position 18143901, C to A substitution causing premature stop codon and truncated 98-amino acid truncated polypeptide) was selected since this C/A substitution destroyed an ApoI restriction site 5'-AAATTC-3' present in un-mutated DNA (chromosome 6 positions 18143896-18143901). Another restriction site for BfuI, 5'-GTATCC-3' was found to be present in both mutated and un-mutated target DNA (chromosome 6 positions 18143904-18143909). Two probes (P1 and P2) were designed to be complementary to nucleotides 18143882-18143922 of the selected target nucleic acid (5'-TTCTGCTCTGTAAAAAATTcTTGTATCCCAAGT-TCACTGAT-3' (P1; SEQ ID NO:9) and 5'-TTCTGCTCT-GTAAAAAATTaTTGTATCCCAAGTTCACTGAT-3' (P2; SEQ ID NO:10)), one corresponding to the un-mutated (P1), and another to mutated DNA (P2), respectively (the SNP positions are shown with lowercase letters).

Once designed and obtained by standard oligonucleotide synthesis methods, probe nucleic acid P1 is conjugated to an amplifying restriction endonuclease (NcoI) and immobilized to the surface of two wells of a microtiter plate. A sample of genomic DNA to be tested is obtained from a patient's blood (with or without PCR amplification and single-stranded target preparation), and added to the two wells. If the target nucleic acid for P1 is present in the genomic DNA, it will bind to P1 in both wells thereby forming restriction sites for recognition restrictases ApoI and BfuI. ApoI is added to the first well, and BfuI is added to the second well, and they are allowed to cleave any formed recognition restriction endonuclease cut sites by incubating the microtiter plate at 37° C. for an appropriate length of time (e.g., 1 minute to 2 hours) for the cleavage reaction to proceed.

After cleavage of the P1:target nucleic acid hybrids by ApoI or BfuI, the reaction solutions in the first and second wells are transferred to third and fourth wells, respectively, both containing reporter nucleic acid that is immobilized to the surface and that has at least one double-stranded portion having an amplifying restriction endonuclease NcoI cut site. The reporter nucleic acid can be a double-stranded nucleic acid having a first strand (e.g., 5'-CATTGCTAGTTGTTTC-CATGGGGTAGTGCGAAATGC-3' (SEQ ID NO:5)) and a second strand (e.g., 5'-GCATTTCGCACTACCCCATG-GAAACAACTAGCAATG-3' (SEQ ID NO:6)). The reporter nucleic acid also has a fluorescent label. In some cases, first signal expansion nucleic acid and second signal expansion nucleic acid are used prior to the reporter nucleic acid step to increase the level of target nucleic acid detection. The first signal expansion nucleic acid and second signal expansion nucleic acid can include labels, in which case they can be used together with reporter nucleic acid or in place of reporter nucleic acid.

After transferring the reaction mixture to the third and fourth chambers, the amplifying restriction endonucleases of the released portions of P1 contact reporter nucleic acid, and the microtiter plate is incubated at an appropriate temperature (e.g., at 37° C.) for an appropriate length of time (e.g., 1 minute to 2 hours) for the cleavage reaction to proceed. The amplifying restriction endonucleases cleave reporter nucleic acid at the double-stranded amplifying restriction endonuclease cut site to form at least two portions. The reaction solutions of the third and fourth wells are transferred to fifth and six wells, respectively, for fluorescence detection using a fluorescent microtiter plate reader. The fluorescent signal in the fifth well is indicative of the amount of un-mutated ApoI cleaved TPMT allelic variant in the sample. The TPMT allelic variant containing the C/A SNP, if present, is not cleaved and doesn't contribute to the signal in the fifth well. The fluorescent signal in the sixth wells is indicative of total amount of the target TPMT nucleic acid in the sample, both mutated and un-mutated. Thus, the allelic composition of the patient's genotype in terms of the corresponding SNP can be evaluated from the ratio of un-mutated TPMT allele to total amount of the TPMT nucleic acid (signal in the fifth well versus signal in the sixth well). A ratio of approximately 0.5 is indicative of heterozygosity. A ratio of approximately 1 is indicative of homozygosity of the un-mutated allele, and a ratio close to zero is indicative of homozygosity of the mutated allele.

Figure 13:
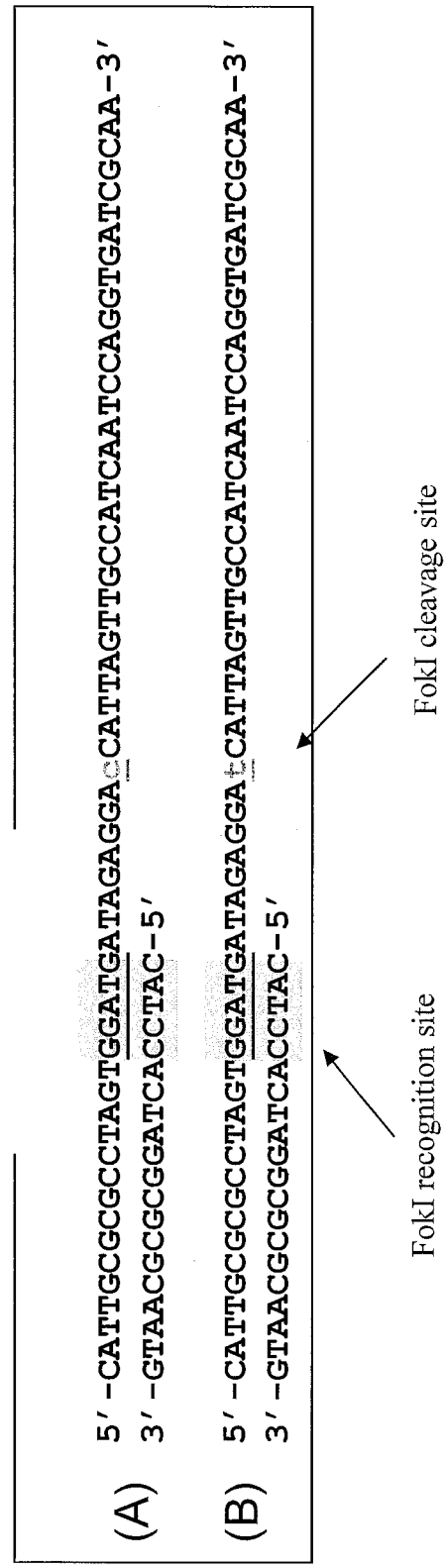
FIG. 13 depicts two probe nucleic acids, one designed to detect target nucleic acid of an un-mutated version of an thiopurine S-methyltransferase (TPMT; EC 2.1.1.67) enzyme (A; SEQ ID NO:13 linked to SEQ ID NO:11), and one designed to detect target nucleic acid of a mutated version of TPMT carrying a SNP in the codon 154 (B; SEQ ID NO:13 linked to SEQ ID NO:12).

Example 7—Assessing Alleles of the Thiopurine S-Methyltransferase Gene Based on a Sequence that does not Appear to Create/Destroy a Restriction Endonuclease Site An allele of the TPMT gene (Ensemble gene ID ENSG00000137364; positioned on Chromosome 6: 18,128, 542-18,155,305 reverse strand) was selected to design an enzymatic amplification cascade of restriction endonucleases using a recognition restriction endonuclease that has separate recognition and cleavage sites (FokI) since the SNP of this allele does not appear to create or destroy a restriction site. The SNP (Ensembl ID rs1800460; chromosome 6 position 18139228, C to T substitution causing non-synonymous substitution in the codon 154) is one of the most common variant alleles (Wang et al., *Proc. Natl. Acad. Sci. USA*, 102(26):9394-9399 (2005)). The corresponding nucleic acid sequence was analyzed using the Ensembl ("http" colon, slash, slash, "uswest" dot "ensemble" dot "org" slash "index" dot "html") genetic database and CLC DNA Workbench to select the SNP site (position 18139228) and flanking sequences, 8 nucleotides upstream (5' direction, 18139220-18139227), and 31 nucleotides downstream (3' direction, 18139229-18139259). These sequences are used to design the single stranded parts of two probe nucleic acids (P1 and P2), one corresponding to the non-mutated genetic element (P1, 5'-ATAGAGGAcCATTAGTTGCCAT-CAATCCAGGTGAT-CGCAA-3'; (SEQ ID NO:11)), and one corresponding to the mutated genetic element (P2, 5'-ATAGAGGAtCATTAGTTGCCATCAATCCAGGT-GATCGCAA-3' (SEQ ID NO:12)). The common double-stranded part of the P1 and P2 probe nucleic acids contained a 15-bp spacer followed by the FokI recognition site: 5'-CATTGCGCGCCTAGTGGATG-3' (SEQ ID NO:13) as shown in FIG. 13.

Once designed and obtained by standard oligonucleotide synthesis methods, the probe nucleic acids are conjugated to an amplifying restriction endonuclease (NcoI) and immobilized to the surface of two wells of a microtiter plate. The first and second wells thus contain P1 for the un-mutated DNA and P2 for the mutated DNA, respectively. A sample of genomic DNA to be tested is obtained from a patient's blood (with or without PCR amplification and single-stranded target preparation), and added to the two wells. If the target nucleic acid is present in the genomic DNA, it can hybridize to the probe nucleic acid in the wells and create a FokI cleavage site with its corresponding probe nucleic acid. The protruding ends of target nucleic acid are removed using blunting by adding T4 DNA polymerase, and then the blunted nucleic acid is ligated to the adjacent available strand of the probe nucleic acid using *E. coli* DNA ligase by incubating the microtiter plate at 20 to 37° C. for an appropriate length of time (e.g., 1 minute to 2 hours) for the enzymatic reactions to proceed. FokI is added to both first and second wells, and is allowed to cleave any formed cleavage sites by incubating the microtiter plate at 37° C. for an appropriate length of time (e.g., 1 minute to 2 hours) for the cleavage reaction to proceed. FokI is only able to cleave the perfect match between the probe nucleic acid and target nucleic acid, and not a single nucleotide mismatch at the cleavage site. After cleavage of the probe nucleic acid:target nucleic acid hybrids by FokI, the reaction solutions in the first and second wells are transferred to third and fourth wells, respectively, both containing reporter nucleic acid that is immobilized to the surface and that has at least one double-stranded portion having an amplifying restriction endonuclease NcoI cut site. The reporter nucleic acid can be a double-stranded nucleic acid having a first strand (e.g., 5'-CATTGCTAGTTGTTTCCATGGGGTA-GTGC-GAAATGC-3' (SEQ ID NO:5)) and a second strand (e.g., 5'-GCATTTCGCAC-TACCCCATGGAAACAACTAG-CAATG-3' (SEQ ID NO:6)). The reporter nucleic acid also has a fluorescent label. In some cases, first signal expansion nucleic acid and second signal expansion nucleic acid are used prior to the reporter nucleic acid step to increase the level of target nucleic acid detection. The first signal expansion nucleic acid and second signal expansion nucleic acid can include labels, in which case they can be used together with reporter nucleic acid or in place of reporter nucleic acid.

After transferring the reaction mixture to the third and fourth chambers, the amplifying restriction endonucleases of the released portions of probe nucleic acid contact reporter nucleic acid, and the microtiter plate is incubated at an appropriate temperature (e.g., at 37° C.) for an appropriate length of time (e.g., 1 minute to 2 hours) for the cleavage reaction to proceed. The amplifying restriction endonucleases cleave reporter nucleic acid at the double-stranded amplifying restriction endonuclease cut site to form at least two portions. The reaction solutions of the third and fourth wells are transferred to fifth and six wells, respectively, for fluorescence detection using a fluorescent microtiter plate reader. The fluorescent signal in the fifth wells is indicative of the amount of the un-mutated TPMT target nucleic acid in the sample. The fluorescent signal in the sixth well is indicative of the amount of mutated TPMT target nucleic acid in the sample. Thus, the allelic composition of the patient's genotype in terms of the corresponding SNP can be evaluated from the ratio of un-mutated TPMT allele to mutated TPMT allele (signal in the fifth well versus signal in the sixth well). The ratio of approximately 1 is indicative of heterozygosity. If the signal in the fifth well greatly exceeding the one in the sixth well, then the results are indicative of homozygosity for the un-mutated allele, and the opposite is indicative of homozygosity for the mutated allele.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A kit for assessing an organism for a genetic or epigenetic element, wherein said kit comprises:
   (a) a probe nucleic acid coupled to a first restriction endonuclease and comprising a nucleotide sequence complementary to a sequence of a target nucleic acid containing said genetic or epigenetic element, wherein at least a portion of said target nucleic acid is capable of hybridizing to at least a portion of said probe nucleic acid to form a double-stranded portion of nucleic acid comprising a restriction endonuclease cut site,
   (b) a signal expansion nucleic acid (i) coupled to a second restriction endonuclease and (ii) comprising a double-stranded portion of nucleic acid comprising a cut site of said first restriction endonuclease of said probe nucleic acid, and
   (c) a reporter nucleic acid (i) coupled to a label and (ii) comprising a double-stranded portion of nucleic acid comprising a cut site of said first restriction endonuclease of said probe nucleic acid or a cut site of said second restriction endonuclease of said signal expansion nucleic acid.

2. The kit of claim 1, wherein said target nucleic acid comprises said genetic element.

3. The kit of claim 2, wherein said genetic element is a single nucleotide polymorphism.

4. The kit of claim 1, wherein said target nucleic acid comprises said epigenetic element.

5. The kit of claim 4, wherein said epigenetic element is a methylated DNA sequence.

6. The kit of claim 1, wherein said kit comprises a solid support, and wherein said probe nucleic acid is attached to said solid support.

7. The kit of claim 6, wherein a portion of said probe nucleic acid comprising said first restriction endonuclease is releasable from said solid support via cleavage with a recognition restriction endonuclease having the ability to cleave at said restriction endonuclease cut site formed by said target nucleic acid and said portion of said probe nucleic acid.

8. The kit of claim 1, wherein said probe nucleic acid is lyophilized.

9. The kit of claim 1, wherein all the ingredients of said kit are lyophilized or dry.

10. The kit of claim 1, wherein said kit comprises a solid support, and wherein said signal expansion nucleic acid is attached to said solid support.

11. The kit of claim 10, wherein said signal expansion nucleic acid is directly attached to said solid support.

12. The kit of claim 1, wherein said label is a fluorescent label, a radioactive label, an enzyme label, or a redox label.

13. The kit of claim 1, wherein said kit is a microfluidic device.

14. The kit of claim 1, wherein said kit further comprises a heating mechanism configured to initiate an exothermic chemical reaction within said kit.

15. The kit of claim 1, wherein said kit further comprises a cooling mechanism configured to initiate an endothermic chemical reaction within said kit.

16. The kit of claim 1, wherein said kit further comprises a temperature indicator.

17. The kit of claim 1, wherein said kit further comprises a recognition restriction endonuclease having the ability to cleave at said restriction endonuclease cut site formed by said target nucleic acid and said portion of said probe nucleic acid.

18. The kit of claim 1, wherein said first restriction endonuclease of said probe nucleic acid is an EcoRI endonuclease, and wherein said second restriction endonuclease of said signal expansion nucleic acid is an EcoRI endonuclease.

19. The kit of claim 1, wherein said first restriction endonuclease of said probe nucleic acid is a BamHI endonuclease, and wherein said second restriction endonuclease of said signal expansion nucleic acid is a BamHI endonuclease.

20. The kit of claim 1, wherein said restriction endonuclease cut site of said first restriction endonuclease of said probe nucleic acid is an EcoRI endonuclease cut site or a BamHI endonuclease cut site.

* * * * *

SEQUENCE LISTING

```
<160> NUMBER OF SEQ ID NOS: 13

<210> SEQ ID NO 1
<211> LENGTH: 40
<212> TYPE: DNA
<213> ORGANISM: Artificial Sequence
<220> FEATURE:
<223> OTHER INFORMATION: nucleic acid containing cleavage site
<220> FEATURE:
<221> NAME/KEY: misc_feature
<222> LOCATION: 6-20 and 26-40
<223> OTHER INFORMATION: n = any nucleic acid

<400> SEQUENCE: 1
ggatgnnnnn nnnnnnnnnn cctacnnnnn nnnnnnnnnn                              40

<210> SEQ ID NO 2
<211> LENGTH: 30
<212> TYPE: DNA
<213> ORGANISM: Artificial Sequence
<220> FEATURE:
<223> OTHER INFORMATION: thiol and biotin containing nucleic acid

<400> SEQUENCE: 2
ggtagtgcga aatgccattg ctagttgttt                                         30

<210> SEQ ID NO 3
<211> LENGTH: 21
<212> TYPE: DNA
<213> ORGANISM: Artificial Sequence
<220> FEATURE:
<223> OTHER INFORMATION: partial complement of SEQ ID NO:2

<400> SEQUENCE: 3
aaacaactag caatggcatt t                                                  21

<210> SEQ ID NO 4
<211> LENGTH: 40
<212> TYPE: DNA
<213> ORGANISM: Homo sapiens

<400> SEQUENCE: 4
gtttattggg gtgctttacc ccggctgtac acagaaagcc                              40

<210> SEQ ID NO 5
<211> LENGTH: 36
<212> TYPE: DNA
```

```
<213> ORGANISM: Artificial Sequence
<220> FEATURE:
<223> OTHER INFORMATION: nucleic acid containing cleavage site

<400> SEQUENCE: 5
cattgctagt tgtttccatg gggtagtgcg aaatgc                              36

<210> SEQ ID NO 6
<211> LENGTH: 36
<212> TYPE: DNA
<213> ORGANISM: Artificial Sequence
<220> FEATURE:
<223> OTHER INFORMATION: partial complement of SEQ ID NO:5

<400> SEQUENCE: 6
gcatttcgca ctaccccatg gaaacaacta gcaatg                              36

<210> SEQ ID NO 7
<211> LENGTH: 40
<212> TYPE: DNA
<213> ORGANISM: Homo sapiens

<400> SEQUENCE: 7
agtccgagtc ctcttggctg cagtagccac tgctcgtcgt                          40

<210> SEQ ID NO 8
<211> LENGTH: 40
<212> TYPE: DNA
<213> ORGANISM: Homo sapiens

<400> SEQUENCE: 8
gtgtcagtgt gcgcgtgcgc ccgggccaga gccgcgccgc                          40

<210> SEQ ID NO 9
<211> LENGTH: 41
<212> TYPE: DNA
<213> ORGANISM: Homo sapiens

<400> SEQUENCE: 9
ttctgctctg taaaaaattc ttgtatccca agttcactga t                        41

<210> SEQ ID NO 10
<211> LENGTH: 41
<212> TYPE: DNA
<213> ORGANISM: Homo sapiens

<400> SEQUENCE: 10
ttctgctctg taaaaaatta ttgtatccca agttcactga t                        41

<210> SEQ ID NO 11
<211> LENGTH: 40
<212> TYPE: DNA
<213> ORGANISM: Homo sapiens

<400> SEQUENCE: 11
atagaggacc attagttgcc atcaatccag gtgatcgcaa                          40

<210> SEQ ID NO 12
<211> LENGTH: 40
<212> TYPE: DNA
<213> ORGANISM: Homo sapiens

<400> SEQUENCE: 12
atagaggatc attagttgcc atcaatccag gtgatcgcaa                          40
```

```
<210> SEQ ID NO 13
<211> LENGTH: 20
<212> TYPE: DNA
<213> ORGANISM: Artificial Sequence
<220> FEATURE:
<223> OTHER INFORMATION: spacer containing FokI restriction site

<400> SEQUENCE: 13
cattgcgcgc ctagtggatg                                              20
```